United States Patent
Shay et al.

(10) Patent No.: US 12,097,213 B2
(45) Date of Patent: Sep. 24, 2024

(54) SEQUENTIAL TREATMENT OF CANCERS USING 6-THIO-dG, CHECKPOINT INHIBITORS AND RADIATION THERAPY

(71) Applicant: The Board of Regents of the University of Texas System, Austin, TX (US)

(72) Inventors: Jerry Shay, Dallas, TX (US); Yang-Xin Fu, Dallas, TX (US); Ilgen Mender, Dallas, TX (US); Anli Zhang, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 132 days.

(21) Appl. No.: 17/200,539

(22) Filed: Mar. 12, 2021

(65) Prior Publication Data

US 2021/0290652 A1 Sep. 23, 2021

Related U.S. Application Data

(60) Provisional application No. 62/989,041, filed on Mar. 13, 2020.

(51) Int. Cl.
| | |
|---|---|
| *A61K 31/7076* | (2006.01) |
| *A61N 5/00* | (2006.01) |
| *A61P 35/00* | (2006.01) |
| *C07K 16/28* | (2006.01) |

(52) U.S. Cl.
CPC ............ *A61K 31/7076* (2013.01); *A61N 5/00* (2013.01); *A61P 35/00* (2018.01); *C07K 16/2818* (2013.01); *C07K 16/2827* (2013.01)

(58) Field of Classification Search
None
See application file for complete search history.

(56) References Cited

U.S. PATENT DOCUMENTS

| | | |
|---|---|---|
| 2013/0210009 A1 | 8/2013 | Budow et al. |
| 2014/0303239 A1 | 10/2014 | Shay et al. |
| 2018/0036331 A1 | 2/2018 | Shay et al. |
| 2019/0298751 A1 | 10/2019 | Shay et al. |
| 2021/0023107 A1 | 1/2021 | Shay et al. |
| 2021/0113602 A1 | 4/2021 | Shay et al. |

FOREIGN PATENT DOCUMENTS

| | | | | |
|---|---|---|---|---|
| CN | 109789206 | | 5/2019 | |
| WO | WO-2017165675 A1 | * | 9/2017 | ......... A61K 31/7076 |
| WO | WO-2017205756 A1 | * | 11/2017 | ........... A61K 31/506 |
| WO | WO 2018-049474 | | 3/2018 | |
| WO | WO 2018/156494 | | 8/2018 | |
| WO | WO 2019/152574 | | 8/2019 | |
| WO | WO 2019/183482 | | 9/2019 | |

OTHER PUBLICATIONS

Office Action issued in Chinese Application No. 202180028952.2, mailed Aug. 25, 2023, and English translation thereof.
Gryaznov et al., "Oligonucleotide conjugate GRN163L targeting human telomerase as potential anticancer and antimetastatic agent," *Nucleosides Nucleotides Nucleic Acids*, 26, 1577-1579, 2007.
Mender et al., "A novel telomerase substrate precursor rapidly induces telomere dysfunction in telomerase positive cancer cells but not telomerase silent normal cells," *Oncoscience*, 2, 693-695, 2015.
Mender et al., "Induction of telomere dysfunction mediated by the telomerase substrate precursor 6-thio-2'-deoxyguanosine," *Cancer Discov*, 5, 82-95, 2015.
Mender et al., "Telomerase-Mediated Strategy for Overcoming Non-Small Cell Lung Cancer Targeted Therapy and Chemotherapy Resistance," *Neoplasia*, 20, 826-837, 2018.
Mender et al., "Telomere Stress Potentiates STING-Dependent Anti-tumor Immunity," Cancer Cell, 38(3):400-411, 2020.
PCT International Preliminary Report on Patentability issued in International Application No. PCT/US2021/022090, mailed Sep. 22, 2022.
PCT International Search Report issued in International Application No. PCT/US2021/022090, mailed Jun. 9, 2021.
Sengupta et al., "Induced Telomere Damage to Treat Telomerase Expressing Therapy-Resistant Pediatric Brain Tumors," Mol Cancer Ther, 17(7):1504-1514, 2018.
Zhang et al., "Induction of Telomere Dysfunction Prolongs Disease Control of Therapy-Resistant Melanoma," *Clin Cancer Res*, 24, 4771-4784, 2018.
Extended European Search Report issued in European Application No. 21767125.4, mailed Oct. 12, 2023.
Mender, "The in vitro and in vivo effects of telomerase substrate 6-Thio-2'-deoxyguanosine," Republic of Turkey, Hacettepe University, Institute of Health Sciences, PhD Thesis, 2014.

\* cited by examiner

*Primary Examiner* — Traviss C McIntosh, III
(74) *Attorney, Agent, or Firm* — Parker Highlander PLLC

(57) ABSTRACT

Disclosed herein are methods of treatments with a telomerase-mediated telomere-targeting drug, 6-thio-2'-deoxyguanosine (6-thio-dG), checkpoint inhibitors and/or radiation therapy for treating cancers. Leads to tumor regression in innate and adaptive immune-dependent manners in syngeneic and humanized mouse cancer models.

16 Claims, 41 Drawing Sheets
Specification includes a Sequence Listing.

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: Synthetic oligo

<400> SEQUENCE: 1
cacctagcct cgcacgaact                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic oligo
```

```
<400> SEQUENCE: 2
cgcaaagggg ggctcgatcg                                            20

<210> SEQ ID NO 3
<211> LENGTH: 20
<212> TYPE: DNA
<213> ORGANISM: Artificial sequence
<220> FEATURE:
<223> OTHER INFORMATION: Synthetic oligo

<400> SEQUENCE: 3
cgccacactc cacggaagca                                            20

<210> SEQ ID NO 4
<211> LENGTH: 20
<212> TYPE: DNA
<213> ORGANISM: Artificial sequence
<220> FEATURE:
<223> OTHER INFORMATION: Synthetic oligo

<400> SEQUENCE: 4
cggggcattc cggataggcc                                            20

<210> SEQ ID NO 5
<211> LENGTH: 22
<212> TYPE: DNA
<213> ORGANISM: Artificial sequence
<220> FEATURE:
<223> OTHER INFORMATION: Synthetic oligo

<400> SEQUENCE: 5
accgattgga tggtttagtg ag                                         22

<210> SEQ ID NO 6
<211> LENGTH: 22
<212> TYPE: DNA
<213> ORGANISM: Artificial sequence
<220> FEATURE:
<223> OTHER INFORMATION: Synthetic oligo

<400> SEQUENCE: 6
cctacggaaa ccttgttacg ac                                         22

<210> SEQ ID NO 7
<211> LENGTH: 19
<212> TYPE: DNA
<213> ORGANISM: Artificial sequence
<220> FEATURE:
<223> OTHER INFORMATION: Synthetic oligo

<400> SEQUENCE: 7
atgagtggtg gttgcaggc                                             19

<210> SEQ ID NO 8
<211> LENGTH: 25
<212> TYPE: DNA
<213> ORGANISM: Artificial sequence
<220> FEATURE:
<223> OTHER INFORMATION: Synthetic oligo

<400> SEQUENCE: 8
tgacctttca aatgcagtag attca                                      25

<210> SEQ ID NO 9
<211> LENGTH: 20
```

```
<212> TYPE: DNA
<213> ORGANISM: Artificial sequence
<220> FEATURE:
<223> OTHER INFORMATION: Synthetic oligo

<400> SEQUENCE: 9
catcaagaag gtggtgaagc                                            20

<210> SEQ ID NO 10
<211> LENGTH: 20
<212> TYPE: DNA
<213> ORGANISM: Artificial sequence
<220> FEATURE:
<223> OTHER INFORMATION: Synthetic oligo

<400> SEQUENCE: 10
cctgttgctg tagccgtatt                                            20
```

SEQUENTIAL TREATMENT OF CANCERS USING 6-THIO-dG, CHECKPOINT INHIBITORS AND RADIATION THERAPY

PRIORITY CLAIM

This application claims benefit of priority to U.S. Provisional Application Ser. No. 62/989,041, filed Mar. 13, 2020, the entire contents of which are hereby incorporated by reference.

FEDERAL GRANT SUPPORT STATEMENT

This invention was made with government support under grant no. 2P50CA070907-21A1 awarded by the National Cancer Institute. The government has certain rights in the invention.

FIELD OF THE DISCLOSURE

The present disclosure relates to the fields of medicine, pharmacology, molecular biology and oncology. More particular, the disclosure relates to methods and compositions for treating cancers using a sequential therapy of 6-thio-dG, a checkpoint inhibitor and/or radiation therapy.

BACKGROUND OF THE DISCLOSURE

Immunotherapies have revolutionized the treatment of many cancers in the immuno-oncology field (Brahmer et al., 2012; Hodi et al., 2010; Ribas and Wolchok, 2018; Topalian et al., 2012). The most commonly used immunotherapies are PD-L1/PD-1 checkpoint blockades that have been approved by the FDA for advanced cancers such as melanoma, non-small cell lung cancer, breast cancer, cervical cancer, colon cancer, head and neck cancer, Hodgkin lymphoma, liver, cancer, lung cancer, renal cell cancer, stomach cancer, rectal cancer, and any solid tumor that is not able to repair errors in its DNA that occur during replication (Garon et al., 2015; Ribas et al., 2016; Rizvi et al., 2015b; Socinski et al., 2018; National Cancer Institute). Despite the success of immunotherapies, many patients do not respond well to these therapies due to the immune suppressive tumor microenvironment, tumor immunogenicity and the emergence of primary and adaptive resistance (Chen and Han, 2015; Gide et al., 2018). Although recent studies show that the abundance of tumor mutations and neoantigens partially dictate cancer patient responses to checkpoint blockade, there are still considerable numbers of patients with high mutations and neoantigens that do not respond well (Le et al., 2017; Mandal et al., 2019; Rizvi et al., 2015a), suggesting neoantigens are not sufficient for provoking anti-tumor immune responses. Therefore, there is an urgent need to identify other factors for better immune responses and to develop new approaches to improve patient overall survival.

The generation of effective anti-tumor adaptive immune responses require tumor antigen presentation by antigen presenting cells, whose activation heavily rely on adequate innate sensing. Innate sensing is often provided by danger signals such as high mobility group box 1 protein, extracellular ATP and tumor DNAs released from stressed tumor cells (Kroemer et al., 2013; Pitt et al., 2017). Recent studies highlight the importance of cytosolic DNA sensing in radiation and DNA damaging therapies (Deng et al., 2014; Sen et al., 2019). The presence of DNA in the cytoplasm, for example, in the form of micronuclei (small DNA containing organelles) that lose nuclear envelop membranes can trigger immune responses. Micronuclei are the products of chromosome damage as a result of genotoxic stress and chromosome mis-segregation during cell division (Fenech et al., 2011). The cytosolic DNA sensor cGAS recognizes micronuclei and converts GTP (guanosine triphosphate) and ATP (adenosine triphosphate) into second messenger cGAMP (cyclic GMP-AMP) (Wu et al., 2013). Then the adaptor protein Stimulator of IFN Gene (STING) binds to cGAMP (Ablasser et al., 2013; Diner et al., 2013; Gao et al., 2013; Zhang et al., 2013). This complex process activates TANK-binding kinase 1 (TBK1) and IFN regulatory factor 3 (IRF3) (Liu et al., 2015; Tanaka and Chen, 2012) and further activates the downstream transcription of type I IFNs and other cytokines (reviewed in (Li and Chen, 2018)), which ultimately increases innate sensing.

Eukaryotic linear chromosomes are capped by special structures called telomeres (TTAGGG), which are essential to maintain chromosomal stability (reviewed in (Blackburn, 1991)). Telomeres constitute the final ~10 kb of all human chromosomes and the final 12-80 kb of all mouse chromosomes (Lansdorp et al., 1996; Zijlmans et al., 1997). In all somatic human cells, telomeres shorten with each cell division due to the end replication problem and the absence of a telomere maintenance mechanism (reviewed in (Greider, 1996)). However, unicellular eukaryotes, germline cells and immortal cancer cells maintain their telomeres at a constant length almost always by activating the enzyme telomerase (Greider and Blackburn, 1985; McEachern and Blackburn, 1996; Morin, 1989; Nakamura et al., 1997; Singer and Gottschling, 1994; Yu et al., 1990). Telomerase is a reverse transcriptase enzyme that elongates telomeres by adding TTAGGG repeats to the ends of chromosomes and is expressed in ~90% of human tumors, but not in most normal cells (Shay and Bacchetti, 1997). Therefore, telomerase is an attractive target to develop anti-cancer therapies.

The nucleoside analogue, 6-thio-2'-deoxyguanosine (6-thio-dG), is a new and an effective therapeutic approach in the cancer field. Its incorporation into de novo synthesized telomeres by telomerase is known to induce damage on telomeric DNA (Mender et al., 2015a). This results in rapid tumor shrinkage or growth arrest in many tumor-derived xenograft models with minimal side effects (Mender et al., 2018; Sengupta et al., 2018; Zhang et al., 2018). The most important advantage of this telomere-targeted therapy over direct telomerase inhibitors is that 6-thio-dG does not have a long lag period for tumor killing effects. Additionally, it does not directly inhibit telomerase but is preferentially recognized by telomerase over other polymerases and incorporated into the telomeres resulting in an immediate DNA chain termination. Importantly, its effect is independent of initial telomere length by hijacking tumor telomerase to make unstable telomeres (Mender et al., 2015b).

SUMMARY OF THE DISCLOSURE

Thus, in one aspect of the disclosure, there is provided methods of treating cancer in a subject involving administering to said subject an effective amount of 6-thio-2'-deoxyguanosine (6-thio-dG) followed by treatment with an immune checkpoint inhibitor per treatment cycle. In some embodiments, the cancer is selected from one or more of pancreatic, lung, mesothelioma, stomach, esophagus, liver, biliary tract, bladder, head & neck, oral, nasopharyngeal, adult brain, colon, rectum, colorectal, prostate, ovarian, cervical, uterine, testicular, lymphoma, leukemia, skin, breast, kidney, neuroblastoma, Merkel cell carcinoma, myelodysplastic syndrome, myelofibrosis, and multiple myeloma.

In some embodiments, the immune checkpoint inhibitor is a PD-1 inhibitor, PD-L1 inhibitor, or CTLA-4 inhibitor. In one embodiment, the immune checkpoint inhibitor is a combination of one or more CTLA-4 inhibitors, one or more of PD-1 inhibitors, or one or more PD-L1 inhibitors.

In some embodiments, the PD-1 inhibitor is selected from one or more of pembrolizumab, nivolumab, cemiplimab, JTx-4014, sasanlimab, budigalimab, BI 754091, spartalizumab, camrelizumab, sintilimab, tislelizumab, zimberlimab, toripalimab, dostarlimab, INCMGA00012, AMP-224, REGN2810, BMS-936558, SHR1210, IBI308, PDR001, BGB-A317, BCD-100, JS001 and AMP-515.

In some embodiments, the PD-L1 inhibitor is selected from one or more of atezolizumab, avelumab, cosibelimab, bintrafusp alfa, durvalumab, MGD013, KN035, KN046, AUNP12, CA-170, and BMS-9986189.

In some embodiments, the CTLA-4 inhibitor is selected from one or more of ipilimumab, and tremelimumab.

In some embodiments of the methods disclosed herein, the 6-thio-dG is administered for about 1 to about 5 days per therapeutic cycle. In some embodiments, the checkpoint inhibitor is administered for about 1 to about 3 days per therapeutic cycle.

As used herein the term therapeutic cycle means about 1 to about 12 weeks between administration of therapies.

In one embodiment of the methods disclosed herein, the 6-thio-dG and the checkpoint inhibitor are administered in combination with a chemotherapeutic agent, a hormonal therapy, a toxin therapy or surgery.

In another embodiment, disclosed herein are methods of treating a cancer, in a subject needing treatment, comprising administering to said subject 6-thio-dG followed by treatment with cemiplimab (Libtayo®), wherein the cancer is selected from one or more of the group consisting of pancreatic, lung, mesothelioma, stomach, esophagus, liver, biliary tract, bladder, head & neck, oral, nasopharyngeal, adult brain, colon, rectum, colorectal, prostate, ovarian, cervical, uterine, testicular, lymphoma, leukemia, skin, breast, kidney, neuroblastoma, Merkel cell carcinoma, myelodysplastic syndrome, myelofibrosis, and multiple myeloma. In some embodiments of this method the 6-thio-dG is administered for about 1 to about 5 days per therapeutic cycle. In some embodiments of the method, cemiplimab is administered for about 1 to about 3 days per therapeutic cycle. In one embodiment of the method, the 6-thio-dG and cemiplimab are administered in combination with a chemotherapeutic agent, a hormonal therapy, a toxin therapy or surgery.

In one embodiment, disclosed herein are methods of treating a cancer, in a subject comprising administering to said subject 6-thio-dG followed by treatment with atezolizumab, wherein the cancer is selected from one or more of the group consisting of pancreatic, lung, mesothelioma, stomach, esophagus, liver, biliary tract, bladder, head & neck, oral, nasopharyngeal, adult brain, colon, rectum, colorectal, prostate, ovarian, cervical, uterine, testicular, lymphoma, leukemia, skin, breast, kidney, neuroblastoma, Merkel cell carcinoma, myelodysplastic syndrome, myelofibrosis, and multiple myeloma. In some embodiments of this method, the 6-thio-dG is administered for about 1 to about 5 days per therapeutic cycle. In some embodiments of the method, atezolizumab is administered for about 1 to about 3 days per therapeutic cycle. In one embodiment of the method, the 6-thio-dG and atezolizumab are administered in combination with a chemotherapeutic agent, a hormonal therapy, a toxin therapy or surgery.

In another aspect of the disclosure, disclosed herein are methods of treating cancer in a subject comprising administering to said subject 6-thio-dG followed by treatment with an immune checkpoint inhibitor administered in combination with radiotherapy. In some embodiments the checkpoint inhibitor is a PD-L1, PD-1, or CTAL-4 inhibitor. In some embodiments the PD-L1 inhibitor is selected from one or more of atezolizumab, avelumab, cosibelimab, bintrafusp alfa, durvalumab, MGD013, KN035, KN046, AUNP12, CA-170, and BMS-9986189. In some embodiments, the PD-L1 inhibitor is atezolizumab. In some embodiments the PD-1 inhibitor is selected from one or more of pembrolizumab, nivolumab, cemiplimab, JTx-4014, sasanlimab, budigalimab, BI 754091, spartalizumab, camrelizumab, sintilimab, tislelizumab, zimberlimab, toripalimab, dostarlimab, INCMGA00012, AMP-224, REGN2810, BMS-936558, SHR1210, IB1I308, PDR001, BGB-A317, BCD-100, JS001 and AMP-515. In some embodiments the PD-1 inhibitor is cemiplimab. In some embodiments, the CTLA-4 inhibitor is ipilimumab or tremelimumab. In some embodiments, the cancer treated is selected from one or more of the group consisting of pancreatic, lung, mesothelioma, stomach, esophagus, liver, biliary tract, bladder, head & neck, oral, nasopharyngeal, adult brain, colon, rectum, colorectal, prostate, ovarian, cervical, uterine, testicular, lymphoma, leukemia, skin, breast, kidney, neuroblastoma, Merkel cell carcinoma, myelodysplastic syndrome, myelofibrosis, and multiple myeloma. In some embodiments, the cancer treated is pancreatic cancer, lung cancer, stomach cancer, liver cancer, bladder cancer, head & neck cancer, oral cancer, nasopharyngeal cancer, brain cancer, colon cancer, prostate cancer, ovarian cancer, cervical cancer, testicular cancer, lymphoma, leukemia, skin cancer, or breast cancer. In some embodiments, the brain cancer is adult brain cancer. In some embodiments, the radiation therapy is administered first followed by one or more check point inhibitors. In some embodiments, the radiation therapy is administered after the administration one or more check point inhibitors.

In some embodiments of the disclosed methods, the cancer treated is lung, colorectal, liver, melanoma, pancreatic, ovarian, or brain (adult).

In some embodiments of the disclosed methods, the cancer treated is pancreatic cancer, lung cancer, stomach cancer, liver cancer, bladder cancer, head & neck cancer, oral cancer, nasopharyngeal cancer, brain cancer, colon cancer, prostate cancer, ovarian cancer, cervical cancer, testicular cancer, lymphoma, leukemia, skin cancer, or breast cancer In other embodiments of the disclosed methods, the total dosage of 6-thio-dG administered over about 1-5 days of therapy is about 10-2000 mg or about 15-2000 mg or about 20-2000 mg or about 10-4800 mg per therapeutic cycle.

In one embodiment of the disclosed methods, the cancer treated is metastatic.

In some embodiments of the disclosed methods, the cancer treated is recurrent or relapsed.

In some embodiments of the disclosed methods, the cancer treated is therapy resistant. In one embodiment, the therapy resistant cancer is checkpoint inhibitor therapy resistant. In another embodiment, the therapy resistant cancer is resistant to one or more of PD-1, PD-L1, and/or CTLA-4 inhibitors. In some embodiments, the cancer is resistant to a tyrosine kinase inhibitor such as, without limitation, erlotinib.

In some embodiments of the methods disclosed herein, the subject treated was previously treated with a checkpoint inhibitor therapy. In one embodiment, the subject was previously treated with one or more of a PD-1, PD-L1, or CTLA-4. In another embodiment, the subject was previously treated with a tyrosine kinase inhibitor therapy.

In some embodiments of the methods disclosed herein, the administration of 6-thio-dG followed by treatment with the checkpoint inhibitor is repeated at least once.

In some embodiments of the methods disclosed herein, the 6-thio-dG and the checkpoint inhibitor are administered systemically. In other embodiments, the 6-thio-dG and the checkpoint inhibitor are administered locally or regionally to a tumor site. In one embodiment, the 6-thio-dG is administered locally or regionally to a tumor site and the checkpoint inhibitor is administered systemically.

In some embodiments of the methods disclosed herein, administration of 6-thio-dG and the checkpoint inhibitor results in inhibition of tumor growth.

In some embodiments of the methods disclosed herein, administration of 6-thio-dG and the checkpoint inhibitor results in remission of the cancer treated.

In some embodiments of the methods disclosed herein, administration of 6-thio-dG and one or more checkpoint inhibitors results in reduction in tumor burden.

In some embodiments of the methods disclosed herein administration of 6-thio-dG and one or more checkpoint inhibitors results in inhibition of cancer cell metastasis.

In some embodiments of the methods disclosed herein, the administration of 6-thio-dG and one or more checkpoint inhibitors results in tumor eradication.

In another aspect, disclosed herein are methods of treating a cancer in a subject comprising administering to said subject a therapeutically effective dose of 6-thio-dG followed by treatment with radiation therapy. In some embodiments, the cancer is selected from the group consisting of pancreatic, lung, mesothelioma, stomach, esophagus, liver, biliary tract, bladder, head & neck, oral, nasopharyngeal, adult brain, colon, rectum, colorectal, prostate, ovarian, cervical, uterine, testicular, lymphoma, leukemia, skin, breast, kidney, neuroblastoma, Merkel cell carcinoma, myelodysplastic syndrome, myelofibrosis, and multiple myeloma. In some embodiments, the cancer treated is pancreatic cancer, lung cancer, stomach cancer, liver cancer, bladder cancer, head & neck cancer, oral cancer, nasopharyngeal cancer, brain cancer, colon cancer, prostate cancer, ovarian cancer, cervical cancer, testicular cancer, lymphoma, leukemia, skin cancer, or breast cancer. In some embodiments, the brain cancer is adult brain cancer.

In another aspect, disclosed herein are methods of treating a cancer in a subject comprising administering to said subject a therapeutically effective dose of 6-thio-dG preceded by treatment with radiation therapy. In some embodiments the cancer is selected from the group consisting of pancreatic, lung, mesothelioma, stomach, esophagus, liver, biliary tract, bladder, head & neck, oral, nasopharyngeal, brain (adult), colon, rectum, colorectal, prostate, ovarian, cervical, uterine, testicular, lymphoma, leukemia, skin, breast, kidney, neuroblastoma, Merkel cell carcinoma, myelodysplastic syndrome, myelofibrosis, and multiple myeloma. In some embodiments, the cancer treated is pancreatic cancer, lung cancer, stomach cancer, liver cancer, bladder cancer, head & neck cancer, oral cancer, nasopharyngeal cancer, brain cancer, colon cancer, prostate cancer, ovarian cancer, cervical cancer, testicular cancer, lymphoma, leukemia, skin cancer, or breast cancer. In some embodiments, the cancer is adult brain cancer.

In one embodiment of the methods disclosed herein, the administration of 6-thio-dG and radiation therapy is repeated at least once.

The cancer may exhibit telomerase activity. The 6-thio-dG and PD-1, PD-L1 and CTLA-4 inhibitor such as atezolizumab, avelumab, cosibelimab, bintrafusp alfa, durvalumab, MGD013, KN035, KN046, AUNP12, CA-170, BMS-9986189 pembrolizumab, nivolumab, cemiplimab, JTx-4014, sasanlimab, budigalimab, BI 754091, spartalizumab, camrelizumab, sintilimab, tislelizumab, zimberlimab, toripalimab, dostarlimab, INCMGA00012, AMP-224, REGN2810, BMS-936558, SHR1210, IB1I308, PDR001, BGB-A317, BCD-100, JS001 AMP-515, ipilmumab, and tremelimumab may be administered in combination with a chemotherapeutic agent, a radiotherapy, a hormonal therapy, a toxin therapy or surgery. The daily dosage of 6-thio-dG administered may be about 0.15 mg/kg to about 70 mg/kg. The gap between 6-thio-dG administration and PD-L1, PD-1 and/or CTLA-4 inhibitor administration may be about 1-14 days, such as about 1-4 days, or about 2-4 days, or about 2-5 days, or about 2-6 days, or about 2-7 days, or about 2-8 days, or about 2-9 days, or about 2-10 days or about 2-11 days or about 2-12 days or about 2-13 days. The method may further comprise the step of assessing telomerase activity in an adult brain cancer cell from said subject. The administration of 6-thio-dG and PD-1, PD-L1 and/or CTLA-4 inhibitor may result in inhibition of tumor growth, remission of said cancer, reduction in tumor burden, inhibition of cancer cell metastasis, or in tumor eradication.

The cancer may be pancreatic cancer, lung cancer, stomach cancer, liver cancer, bladder cancer, head & neck cancer, oral cancer, nasopharyngeal cancer, brain cancer, colon cancer, prostate cancer, ovarian cancer, cervical cancer, testicular cancer, lymphoma, leukemia, or skin cancer. The cancer may be metastatic and/or recurrent and/or therapy resistant. The therapy resistant cancer may be checkpoint inhibitor therapy resistant, such as PD-L1, PD-1 and/or CTLA-4 resistant. The subject may have been previously treated with a checkpoint inhibitor therapy, such as a PD-L1, PD-1 and/or CTLA-4 therapy. The administration of 6-thio-dG followed by treatment with a PD-1, PD-L1 and/or CTLA4 inhibitor is repeated at least once. The 6-thio-dG and PD-1, PD-L1 and/or CTLA4 inhibitor may be administered systemically or administered local or regional to a tumor site. 6-thio-dG may be administered in the same or a different route than the PD-i, PD-L1 and/or CTLA4 inhibitor.

Other objects, features and advantages of the present disclosure will become apparent from the following detailed description. It should be understood, however, that the detailed description and the specific examples, while indicating particular embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Cell viability (IC$_{50}$) of 6-thiodG in MC38 cells. Cells were treated with 6-thio-dG for 5 days. (FIG. 1B and FIG. 1C) Colony formation assay of 6-thio-dG in MC38 cells at indicated doses for 13 days. Cells were treated with 6-thio-dG every 3 days, then fixed and stained with crystal violet.

Representative image of three biological replicates were shown in FIG. 1B and the quantification data was shown in FIG. 1C. (FIG. 1D and FIG. 1E) WT (FIG. 1D) or Rag1−/− (FIG. 1E) C57BL/6 mice (n=5) were inoculated with $5 \times 10^5$ MC38 tumor cells and treated with 6-thio-dG (3 mg/kg, days 7, 8, 9). (FIG. 1F and FIG. 1G) C57BL/6 mice (n=5) were inoculated with $5 \times 10^5$ MC38 tumor cells and treated with 6-thio-dG (3 mg/kg, days 7, 8, 9). 200 μg of anti-CD4 (FIG. 1F) or anti-CD8 (FIG. 1G) was administrated one day before treatment initiation and then twice a week for 3 weeks. Tumor growth was measured every 3 days. Data were shown as mean±SEM from two to three independent experiments. P value was determined by two-tailed unpaired t test (FIG. 1C) or two-way ANOVA (FIGS. 1D-G). See also FIGS. 9A-D.

(FIG. 2A and FIG. 2B) C57BL/6 mice (n=4-5) were inoculated with $5 \times 10^5$ MC38 tumor cells and treated with 6-thio-dG (3 mg/kg, days 7, 8, 9). Six days after last treatment, tumor infiltrating T cells were analyzed for the frequency of total T cells (FIG. 2A) and Ki67+CD8+ T cells (FIG. 2B). (FIG. 2C) C57BL/6 mice (n=5) bearing MC38-OVA tumor were treated with 6-thio-dG (3 mg/kg, days 7, 8, 9). Three days after last treatment, tumor infiltrating T cells were analyzed for OVA specific CD8+ T cells with $H-2K^b$-$OVA_{257-264}$ tetramer. (FIG. 2D and FIG. 2E) Same experiment scheme as in (A), splenocytes were collected and re-stimulated with irradiated MC38 tumor cells for 48 hrs. IFN-γ producing cells were determined by ELISPOT assay. Representative spots were shown in FIG. 2D and the quantification data (n=5) was shown in FIG. 2E. (FIG. 2F) IFN-γ reporter mice (n=3) were inoculated with $5 \times 10^5$ MC38 tumor cells and treated with 6-thio-dG (3 mg/kg, days 7, 8, 9). Eleven days after the last treatment, tumors were minced and digested for flow cytometric detecting of YFP+ T cells. P value was determined by two-tailed unpaired t test (FIGS. 2A-C, FIG. 2E and FIG. 2F). See also FIGS. 102A-F.

(FIG. 3A) C57BL/6 mice (n=5) were inoculated with $5 \times 10^5$ MC38 tumor cells and treated with 6-thio-dG (3 mg/kg, days 7, 8, 9). 200 μg anti-CSF1R was administrated one day before treatment initiation and then twice a week for 3 weeks. (FIG. 3B) Batf3−/− mice (n=5) were inoculated with $5 \times 10^5$ MC38 tumor cells and treated with 6-thio-dG (3 mg/kg, days 7, 8, 9). Tumor growth was measured every 3 days. (FIG. 3C) Percentage of tumor free mice in WT and Batf3−/− mice (n=5) after 6-thio-dG treatment. (FIG. 3D) BMDCs were cultured with MC38 tumor cells that were pretreated with 200 nM 6-thio-dG or vehicle for overnight, and then DCs were purified and co-cultured with naïve OT-1 T cells. 48 hrs later, supernatant was collected and tested for IFN-γ production by cytometric bead array (CBA). (FIG. 3E) BMDC were cultured with MC38 tumor cells that were pretreated with 200 nM 6-thio-dG or vehicle for 18 hrs, supernatant was collected for IFN-β ELISA. (F) Ifnar1−/− mice (n=5) were inoculated with $5 \times 10^5$ MC38 tumor cells and treated with 6-thio-dG (3 mg/kg, days 7, 8, 9). Tumor growth was measured every 3 days. Data were shown as mean±SEM from two to three independent experiments. P value was determined by two-way ANOVA (FIG. 3A, FIG. 3B and FIG. 3F) or two-tailed unpaired t test (FIGS. 3C-E).

(FIG. 4A and FIG. 4B) Myd88−/− (FIG. 4A) or Tmem173−/− (FIG. 4B) mice (n=5) were inoculated with $5 \times 10^5$ MC38 tumor cells and treated with 6-thio-dG (3 mg/kg, days 7, 8, 9). Tumor growth was measured every 3 days. (FIG. 4C and FIG. 4D) C57BL/6 mice (n=5) were inoculated with $5 \times 10^5$ Tmem173 KO (FIG. 4C) or Mb21d1 KO (FIG. 4D) MC38 tumor cells and treated with 6-thio-dG (3 mg/kg, days 7, 8, 9). Tumor growth was measured every 3 days. (FIG. 4E and FIG. 4F) MC38 tumor cells were treated with 1 μM 6-thio-dG for 24 hrs. TIF (Telomere dysfunction Induced Foci) assay confirms induction of TIFs with 6-thio-dG treatment in MC38 cells. n=100 (control), n=100 (6-thio-dG). (FIG. 4G) BMDCs were cultured with HCT116 human colon cancer cells that were pretreated with 500 nM 6-thio-dG or vehicle for 4 hrs, then DCs were purified and cytosolic DNAs were extracted. Relative abundance of MT-CO1 and human 18S in the cytosol of DC were detected by qPCR. Data were shown as mean±SEM from two to three independent experiments. P value was determined by two-way ANOVA (A-D) or two-tailed unpaired t test (FIG. 4F and FIG. 4G). See also FIGS. 11A-H.

(FIG. 5A) C57BL/6 mice bearing MC38 tumor (n=4-5) were treated with 6-thio-dG (3 mg/kg, days 7, 8, 9). 7 days after first treatment, PD-1+ CD8+ T cell frequency (left) and PD-1 MFI (right) were tested. (FIG. 5B and FIG. 5C) C57BL/6 mice (n=5) were inoculated with $5 \times 10^5$ MC38 tumor cells and treated with 6-thio-dG (3 mg/kg, days 10, 11). 50 μg anti-PD-L1 antibody was administrated on days 13 and 17. Tumor growth (FIG. 5B) and survival capacity (FIG. 5C) were shown. (FIG. 5D) C57BL/6 mice (n=5) bearing MC38 tumor were treated with 6-thio-dG (3 mg/kg, days 10, 11) or anti-PD-L1 (2.5 kg/mg, day 10) or combination treatment of both. 7 days after first treatment, draining lymphoid was harvested and stimulated with irradiated MC38 tumor cells or LLC tumor cells for IFN-γ ELISPOT. (FIG. 5E and FIG. 5F) C57BL/6 mice (n=5) were inoculated with $1 \times 10^6$ LLC murine lung tumor cells and treated with 6-thio-dG (3 mg/kg, days 4, 5, 6 and 10, 11). 200 μg anti-PD-L1 antibody was administrated on day 8 and day 13. Tumor growth was measured every 3-4 days (FIG. 5E). Six weeks later, tumor free mice (n=4) in sequential treatment group and control mice were re-challenged with $5 \times 10^6$ LLC (right flank) and $5 \times 10^6$ MC38 (left flank) tumor cells. Tumor growth was measured every 3-4 days (FIG. 5F). Data were shown as mean±SEM from two independent experiments. P value was determined by two-tailed unpaired t test (FIG. 5A, FIG. 5D) or two-way ANOVA (FIG. 5B, FIG. 5E and FIG. 5F) or Log-rank test (FIG. 5C). See also FIG. 12.

(FIG. 6A) Overall survival in high and low TERT (Telomerase reverse transcriptase, the catalytic subunit of the telomerase) expression colorectal adenocarcinoma patients from TCGA database. (FIG. 6B) Cell viability ($IC_{50}$) of 6-thio-dG in HCT116 human colon cancer cells. Cells were treated with 6-thio-dG for 5 days. (FIG. 6C) The schema for humanized mouse tumor model. (FIG. 6D and FIG. 6E) NSG-SGM3 mice (n=5) (FIG. 6D) or humanized NSG-SGM3 mice (n=4) (FIG. 6E) were inoculated with $1 \times 10^6$ HCT116 tumor cells and treated with 6-thio-dG (3 mg/kg, days 8, 9, 10). Tumor growth was measured every 3 days. Data were shown as mean±SEM from two independent experiments. P value was determined by Log-rank test (FIG. 6A) or two-way ANOVA (FIG. 6D and FIG. 6E). See also FIGS. 13A-F.

(FIG. 9A) Cell viability ($IC_{50}$) of 6-thio-dG in LLC murine lung cancer cells. Cells were treated with 6-thio-dG for 4 days. (FIG. 9B) C57BL/6 mice (n=5) were inoculated with $1\times10^6$ LLC tumor cells and treated with 6-thio-dG (3 mg/kg, days 4, 5, 6). Tumor growth was measured every 3 days. (FIG. 9C) $IC_{50}$ of 6-thio-dG in CT26 murine colon cancer cells. (FIG. 9D) BALB/C mice (n=5) were inoculated with $5\times10^5$ CT26 tumor cells and treated with 6-thio-dG (3 mg/kg, days 5, 6, 7). Tumor growth was measured every 3 days. Data were shown as mean±SEM from two independent experiments. P value was determined by two-way ANOVA.

(FIGS. 10A-D) C57BL/6 mice (n=4-5) were inoculated with $5\times10^5$ MC38 tumor cells and treated with 6-thio-dG (3 mg/kg, days 7, 8, 9). 7 days after first treatment, tumors were analyzed for CD8+ T cells among CD45+ cells (FIG. 10A) and among total tumor cells (FIG. 10B), tumor infiltrating T cells were analyzed for the frequency of $CD4^+$ $Foxp3^+$ Treg cells (FIG. 10C) and NK cells (FIG. 11D). (FIG. 10E) C57BL/6 mice (n=5) were inoculated with $5\times10^5$ MC38 tumor cells and treated with 6-thio-dG (3 mg/kg, days 7, 8, 9). 200 µg anti-NK1.1 was administrated one day before treatment initiation and then twice a week for 3 weeks. (FIG. 10F) IFN-γ reporter mice (n=3) were inoculated with $5\times10^5$ MC38 tumor cells and treated with 6-thio-dG (3 mg/kg, days 7, 8, 9). Eleven days after the last treatment, tumors were minced and digested for flow cytometric detection of YFP+ T cells. Representative flow cytometry gating was shown. Data were shown as mean±SEM from two independent experiments. P value was determined by two-tailed unpaired t test in (FIGS. 10A-D) or two-way ANOVA (FIG. 10E).

(FIG. 11A) BMDCs were cultured with MC38 tumor cells that were pretreated with 0.2 µM or 1 µM 6-thio-dG for 6 hrs, and then DCs were purified with magnetic beads and subjected to western blot. (FIG. 11B) BMDCs from wild-type (WT) or Tmem173KO mice were cultured with MC38 tumor cells that were pretreated with 200 nM 6-thio-dG for overnight, and then DCs were purified with magnetic beads and qPCR was performed to test the relative abundance of IFN-β. (FIGS. 11C and 11D) C57BL/6 mice (n=3) were inoculated with $5\times10^5$ MC38 tumor cells and treated with 6-thio-dG (3 mg/kg, days 10, 11 and 12). 3 days after last injection, mice were sacrificed; tumors were collected and fixed for TIF (Telomere dysfunction Induced Foci) staining. Images were obtained by fluorescein microscope (100×). Red dots show DNA damage (γ-H2AX), green dots show telomeres and yellow dots show TIF (DNA damage on telomeres). Scale bars, 10 µM. (FIGS. 11E and 11F) 6-thio-dG treatment induced micronuclei in MC38 cells. (FIG. 11E) Representative picture of two daughter cells in late telophase contain telomere signals and coated and uncoated micronuclei in MC38 cells. Green dots represent telomeric signals and red color represents lamin A/C (nuclear envelop biomarker). (FIG. 11F) Quantification of 1 µM 6-thio-dG treatment induced micronuclei after 48 hrs. (FIGS. 11G and 11H) 100,000 MC38 cells were seeded in 6-well plate and cells were labeled with 25 µM EdU. 2 days later, cells were washed out and incubated with 1 µM 6-thio-dG in fresh media O/N. Cells were then washed out and co-cultured with DCs O/N. The next day, DCs were purified with magnetic beads. Purified DCs were then fixed and cytospun for immuno-FISH. Telomeric probe: green, EdU: red, DAPI: blue. Images were captured at 63× magnification with an Axio Imager Z2 equipped with an automatic capture system and analyzed with ISIS software (camera: coolcube 1-metasystems). Representative imaging (FIG. 11G) and quantification data (FIG. 11H) were shown, n=100. Data were shown as mean±SEM from two to three independent experiments. P value was determined by two-tailed unpaired t test (B, F and H).

(FIGS. 13A-C) 12 weeks after humanized mouse reconstitution, human CD45+ cells and CD3+ T cells in mouse peripheral blood were tested by flow cytometry. Representative flow cytometric plot was shown in FIG. 13A. CD45 and CD3 frequency in control and 6-thio-dG groups before treatment were shown in FIGS. 13B and 13C, n=5. (FIG. 13D) Cell viability ($IC_{50}$) of 6-thio-dG in A375 human melanoma cancer cells. Cells were treated with 6-thio-dG for 4 days. (FIG. 13E) NSG-SGM3 mice (n=5) were inoculated with $2\times10^6$ A375 tumor cells and treated with 6-thio-dG (3 mg/kg, day 7 and day 8) or anti-PD-L1 plus anti-CTLA-4 (200 µg i.p., day 10 and day 13) or the combination of 6-thio-dG plus anti-PD-L1 and anti-CTLA-4. Tumor growth was measured every 3 days. (FIG. 13F) Humanized NSG-SGM3 mice (n=5-7) were inoculated with $2\times10^6$ A375 tumor cells and treated with 6-thio-dG (3 mg/kg, day 13 and day 14) or anti-PD-L1 plus anti-CTLA-4 (200 µg i.p., day 16 and day 19) or the combination of 6-thio-dG plus anti-PD-L1 and anti-CTLA-4. Tumor growth was measured every 3 days. Data were shown as mean±SEM. P value was determined by two-tailed unpaired t test (FIGS. 13B and 13C, n.s. p>0.05) or two-way ANOVA (FIG. 13F).

TABLE A

| | | | Dosing Schedule | | | | | |
|---|---|---|---|---|---|---|---|---|
| Mice # | | Group name | Jan. 13, 2021 Day 13 | Jan. 14, 2021 Day 14 | Jan. 15, 2021 Day 15 | Jan. 17, 2021 Day 17 | Jan. 19, 2021 Day 19 | Jan. 20, 2021 Day 20 |
| 5 | Group 1 | Control | | | | | | |
| 5 | Group 2 | THIO | THIO | THIO | THIO | | THIO | THIO |
| 5 | Group 7 | THIO + LIBTAYO | THIO | THIO | THIO | LIBTAYO | THIO | THIO |

TABLE A-continued

| | | \<td colspan="5">Dosing Schedule</td> |
|---|---|---|

| Mice # | Group name | Jan. 21, 2021 Day 21 | Jan. 23, 2021 Day 23 | Jan. 26, 2021 Day 26 | Jan. 29, 2021 Day 29 | Feb. 2, 2021 Day 33 |
|---|---|---|---|---|---|---|
| 5 | Group 1 Control | | | | | |
| 5 | Group 2 THIO | THIO | | | | |
| 5 | Group 7 THIO + LIBTAYO | THIO | LIBTAYO | LIBTAYO | LIBTAYO | LIBTAYO |

| | | | | | Dosing Schedule | | | | |
|---|---|---|---|---|---|---|---|---|---|
| Mice # | | Jan. 11, 2021 Day 11 | Jan. 12, 2021 Day 12 | Jan. 14, 2021 Day 14 | Jan. 15, 2021 Day 15 | Jan. 16, 2021 Day 16 | Jan. 17, 2021 Day 17 | Jan. 19, 2021 Day 19 | Jan. 21, 2021 Day 21 |
| 5 | Group 3 THIO | THIO | THIO | | | THIO | THIO | | THIO |
| 5 | Group 4 LIBTAYO | LIBTAYO | | | LIBTAYO | | | LIBTAYO | |
| 5 | Group 5 THIO/LIBTAYO | THIO | THIO/LIBTAYO | | | THIO | THIO/LIBTAYO | | THIO |
| 5 | Group 6 THIO + LIBTAYO | THIO | THIO | LIBTAYO | | THIO | THIO | LIBTAYO | THIO |

| | | | | | Dosing Schedule | | | |
|---|---|---|---|---|---|---|---|---|
| Mice # | | Jan. 22, 2021 Day 22 | Jan. 24, 2021 Day 24 | Jan. 25, 2021 Day 25 | Jan. 27, 2021 Day 27 | Jan. 29, 2021 Day 29 | Jan. 30, 2021 Day 30 | Feb. 2, 2021 Day 33 |
| 5 | Group 3 THIO | THIO | | | | | | |
| 5 | Group 4 LIBTAYO | LIBTAYO | | LIBTAYO | | | | |
| 5 | Group 5 THIO/LIBTAYO | THIO/LIBTAYO | | | LIBTAYO | | LIBTAYO | |
| 5 | Group 6 THIO + LIBTAYO | THIO | LIBTAYO | | | LIBTAYO | | LIBTAYO |

Figure 15:
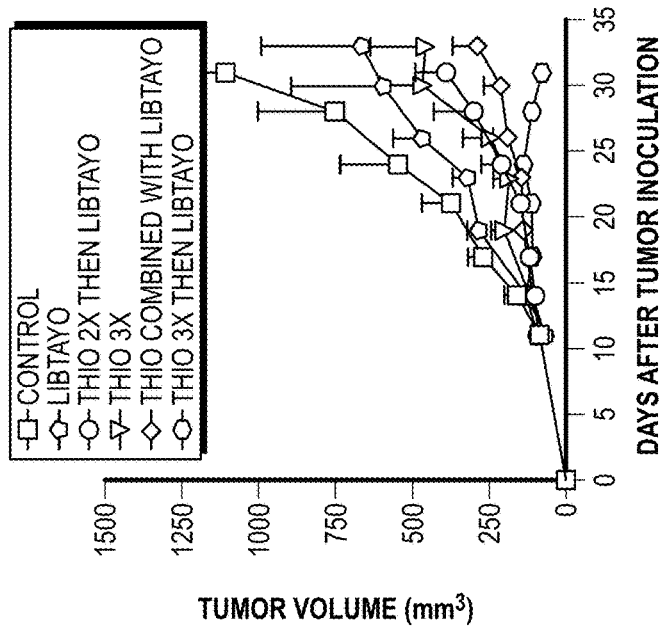

FIG. 15 shows the effects of 6-thio-dG with anti-PD-1 agent cemiplimab (Libtayo®) on tumor volume in mice carrying LLC cells-derived tumors (NSCLC). Dosing was 6-thio-dG 3 mg/kg (i.p) and cemiplimab-10 mg/kg (i.p). The different groups were dosed as shown in the table above. Day 1 (12/31/2020): 1000K LLC cells were inoculated to 35 B6 mice. Day 11-13: Experiment started. 3 mg/kg 6-thio-dG and 10 mg/kg Libtayo were used in this study.

Figure 16:
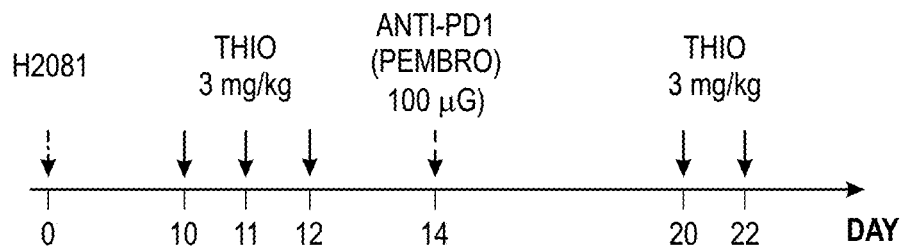
Figure 16:
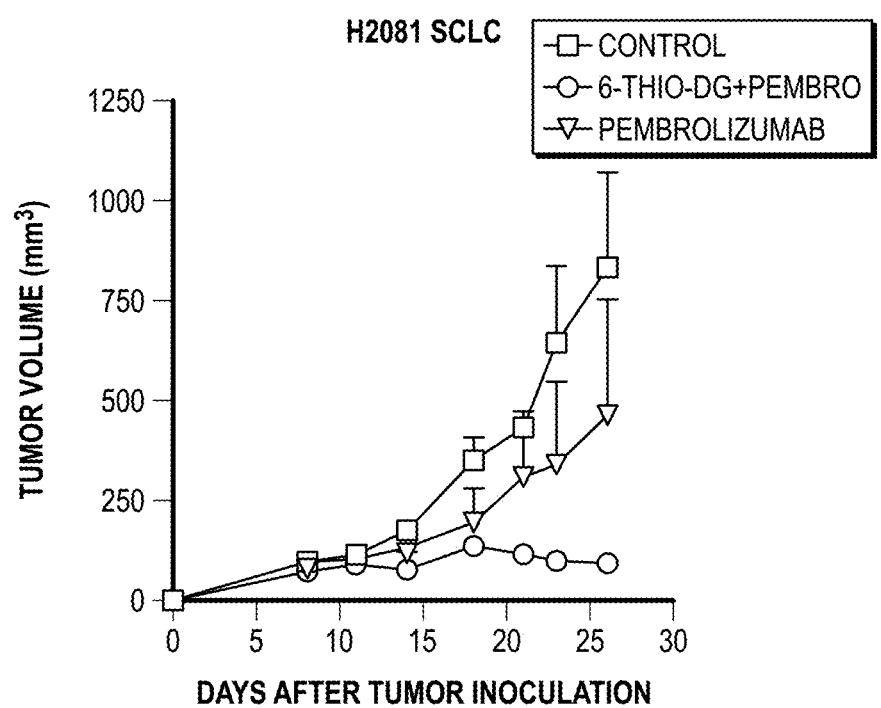

FIG. 16 shows the effect of 6-thio-dG in combination with a PD-1 agent pembrolizumab in small cell lung cancer (SCLC) humanized mouse model.

Figure 17:
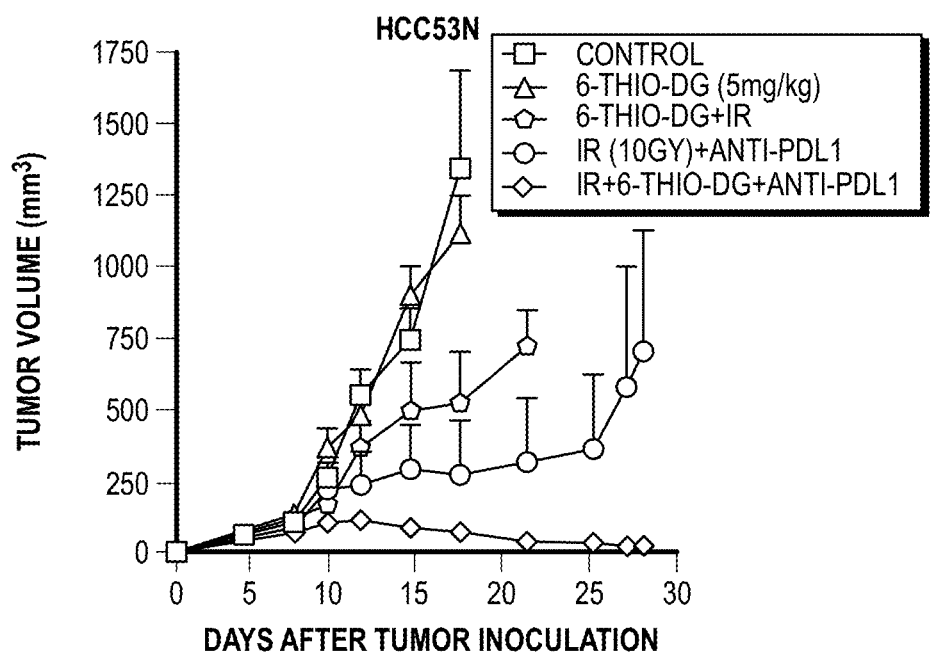

FIG. 17 shows 6-thio-dG in combination with PD-L1 inhibitor and radiation in an HCC Mouse Model.

Figure 18A:
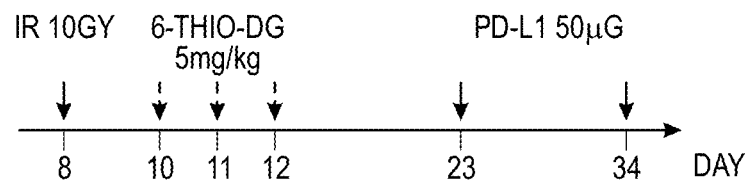
Figure 18B:
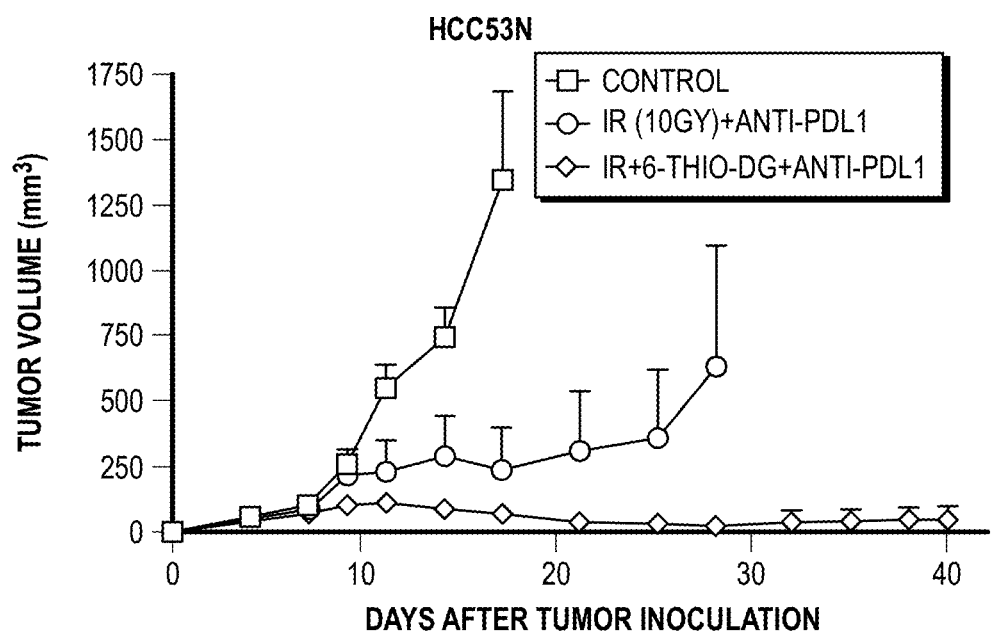
Figure 18C:
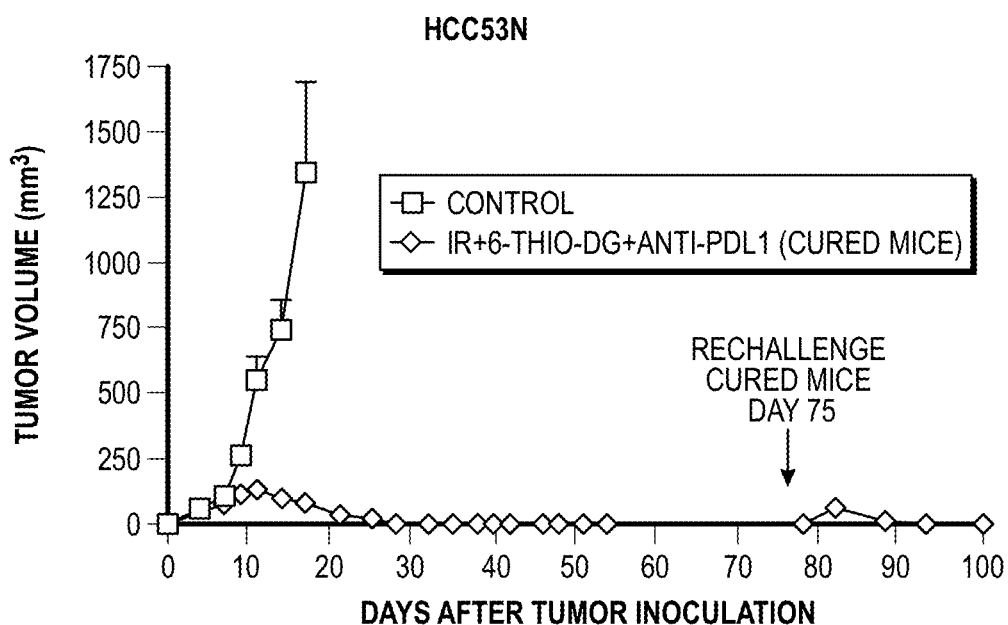
Figure 18D:
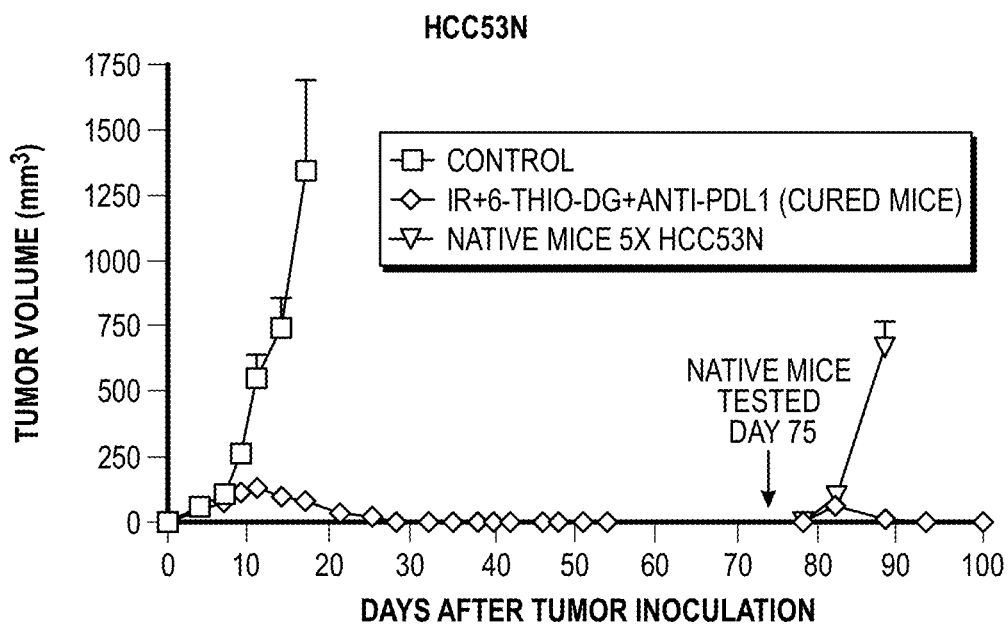

FIGS. 18A-18D show 6-thio-dG in Combination with a PD-L1 and Radiation in HCC Mouse Model. FIG. 18A dosing schedule. FIG. 18B HCC53N liver cancer cells (p53 and NRAS knockout) treated in vivo initially with focal IR followed by 3 doses with 6-thio-dG followed by 2 treatments with anti-PD-L1 antibody resulted in complete tumor remissions. FIG. 18C re-challenged with 10 times more HCC53N cells no tumors regrew suggesting immunological memory; and FIG. 18D when naive mice were tested tumors grew rapidly.

DETAILED DESCRIPTION

Telomerase is almost universally expressed in tumor cells. The telomerase-mediated telomere-targeted drug, 6-thio-dG, reduces the lag time between the initial treatment and response to therapy by directly inducing telomere damage in telomerase-positive cancer cells but not in normal telomerase silent cells. In this study, the inventors aimed to explore whether 6-thio-dG that induces telomere stress in telomerase-positive cancer cells could initiate rapid DNA damage for innate sensing. They used syngeneic wild-type and genetic deficient mice to evaluate how 6-thio-dG triggers innate sensing and how it contributes to host anti-tumor immunity. Importantly, they demonstrate that 6-thio-dG overcomes PD-L1 blockade resistance in advanced tumors. Unexpectedly, 6-thio-dG induced DNA mediated innate sensing and activation of immune responses in a host STING-dependent manner, leading to improved anti-tumor efficacy. Moreover, 6-thio-dG sequentially followed by anti-PD-L1 therapy can completely eliminate advanced tumors. Thus, 6-thio-dG is a tumor-targeting and immune-stimulating drug that can benefit telomerase-positive and PD-L1 resistant cancer patients in the clinic.

These and other aspects of the disclosure are described in detail below.

I. TELOMERES, TELOMERASE AND TELOMERE DYSFUNCTION

During mitosis, cells make copies of their genetic material. Half of the genetic material goes to each new daughter cell. To make sure that information is successfully passed from one generation to the next, each chromosome has a special protective cap called a telomere located at the end of its "arms." Telomeres are controlled by the presence of the enzyme telomerase.

A telomere is a repeating DNA sequence (for example, TTAGGG) at the end of the body's chromosomes. The telomere can reach a length of 15,000 base pairs. Telomeres function by preventing chromosomes from losing base pair sequences at their ends. They also stop chromosomes from fusing to each other. However, each time a cell divides, some of the telomere is lost (usually 25-200 base pairs per division). When the telomere becomes too short, the chromosome reaches a "critical length" and can no longer replicate. This means that a cell becomes old and dies by a process called apoptosis or undergoes senescence. Telomere activity is controlled by two mechanisms: erosion and addition. Erosion, as mentioned, occurs each time a cell divides due to the failure of lagging strand DNA synthesis to be completed all the way to the end. Addition is determined by the activity of telomerase.

Telomerase, also called telomere terminal transferase, is an enzyme made of protein and RNA subunits that elongates chromosomes by adding TTAGGG sequences to the end of existing chromosomes. Telomerase is found in fetal tissues, adult germ cells, and also tumor cells. Telomerase activity is regulated during development and has a very low, almost undetectable activity in somatic (body) cells. Because these somatic cells do not regularly use telomerase, they age. The result of aging cells is an aging body. If telomerase is activated in a cell, the cell will continue to grow and divide. This "immortal cell" theory is important in two areas of research: aging and cancer.

Cellular aging, or senescence, is the process by which a cell becomes old and stops growing or dies. It is due to the shortening of chromosomal telomeres to the point that the chromosome reaches a critical length. Cellular aging is analogous to a wind-up clock. If the clock stays wound, a cell becomes immortal and constantly produces new cells. If the clock winds down, the cell stops producing new cells and undergoes what is termed replicative senescence or dies. Cells are constantly aging. Being able to make the body's cells extend their replication ability certainly creates some exciting possibilities especially for disease associated with genetic inheritance of short telomeres (termed telomeropathies or telomere spectrum disorders). Telomerase research could therefore yield important discoveries related to the aging process.

Cancer cells have escaped the normal short telomere aging phenomenon and become malignant cells. The malignant cells multiply until they form a tumor that grows uncontrollably and spreads to distant tissue throughout the human body. Telomerase has been detected in almost all human cancer cells. This provides a selective growth advantage to many types of tumors. If telomerase activity was to be turned off, then telomeres in cancer cells would progressively shorten, just like they do in normal body cells. This would prevent the cancer cells from dividing uncontrollably in their early stages of development. In the event that a tumor has already thoroughly developed, it may be removed and anti-telomerase therapy could be administered to prevent relapse. In essence, preventing telomerase from performing its function would change cancer cells from immortal to mortal. However, direct telomerase inhibitors require a lag period from initiation of treatment until tumor shrinkage occurs and have not progressed well in clinical development due to increased toxicities. Thus, the present invention provides methods to reduce the lag period but require telomerase activity to be effective and potentially reduce side effects.

II. TREATING CANCER

A. Therapeutic Agents for Sequential Therapy

1. In some embodiments the PD-L1 inhibitor is selected from one or more of atezolizumab, avelumab, cosibelimab, bintrafusp alfa, durvalumab, MGD013, KN035, KN046, AUNP12, CA-170, and BMS-9986189. In some embodiments, the PD-L1 inhibitor is atezolizumab.

Atezolizumab (trade name Tecentriq®) is a fully humanized, engineered monoclonal antibody of IgG1 isotype against the protein programmed cell death-ligand 1 (PD-L1). In 2015, it was in clinical trials as an immunotherapy for several types of solid tumors. In May 2016, it was approved by the FDA for bladder cancer treatment, but in May 2017, it failed phase III trial for second line bladder cancer. In October 2016, FDA approved Atezolizumab for urothelial carcinoma and the treatment of patients with metastatic non-small cell lung cancer (NSCLC) whose disease progressed during or following platinum-containing chemotherapy. Patients with EGFR or ALK genomic tumor aberrations should have disease progression on FDA-approved therapy for these aberrations prior to receiving Atezolizumab. In September 2018, it was announced that Atezolizumab prolongs survival in extensive stage small cell lung cancer treatment, according to study results presented at the 19th World Conference on Lung Cancer (WCLC) in Toronto, Canada. In October 2018, a combined clinical trial of the drug with nab-paclitaxel on patients with advanced triple negative breast cancer concluded. In March 2019, it was approved in the United States, in combination with paclitaxel protein-bound, for adult patients with unresectable locally advanced or metastatic triple-negative breast cancer (TNBC) whose tumors express PD-L1 (PD-L1 stained tumor-infiltrating immune cells of any intensity covering ≥1% of the tumor area), as determined by an FDA-approved test. In March 2019, it was approved in the United States, in combination with carboplatin and etoposide, for the first-line treatment of adult patients with extensive-stage small cell lung cancer (ES-SCLC). The most common adverse effects in studies were fatigue, decreased appetite, nausea, and infections. Urinary tract infection was the most common severe adverse effect.

Atezolizumab blocks the interaction of PD-L1 with programmed cell death protein 1 (PD-1) and CD80 receptors (B7-1Rs). PD-L1 can be highly expressed on certain tumors, which is thought to lead to reduced activation of immune cells (cytotoxic T-cells in particular) that might otherwise recognize and attack the cancer. Inhibition of PD-L1 by Atezolizumab can remove this inhibitor effect and thereby engender an anti-tumor response. It is one of several ways to block inhibitory signals related to T-cell activation, a more general strategy known as immune checkpoint inhibition. For some cancers (notably bladder) the probability of benefit is related to PD-L1 expression, but most cancers with PD-L1 expression still do not respond, and some (about 15%) without PD-L1 expression do respond.

Avelumab (Bavencio®) is a fully human IgG1 antibody developed by Merck Serono and Pfizer. Avelumab is FDA approved for the treatment of metastatic Merkel-cell carcinoma. It failed phase III clinical trials for gastric cancer.

Durvalumab (Imfinzi®) is a fully human IgG1 antibody developed by AstraZeneca.

Durvalumab is FDA approved for the treatment of urothelial carcinoma and unresectable non-small cell lung cancer after chemoradiation.

KN035 is the only PD-L1 antibody with subcutaneous formulation currently under clinical evaluations in the US, China, and Japan.

AUNP12 is a 29-mer peptide as the first peptic PD-i/PD-L1 inhibitor developed by Aurigene and Laboratoires Pierre Fabre that is being evaluated in clinical trials for treating cancer.

CA-170, discovered by Aurigene/Curis as a PD-L1 and VISTA antagonist is currently under phase I clinical trial for treatment of mesothelioma.

2. PD-1 inhibitors such as cemiplimab, pembrolizumab, nivolumab, JTx-4014, sasanlimab, budigalimab, BI 754091, spartalizumab, camrelizumab, sintilimab, tislelizumab, zimberlimab, toripalimab, dostarlimab, INCMGA00012, AMP-224, REGN2810, BMS-936558, SHR1210, IB1308, PDR001, BGB-A317, BCD-100, JS001 and AMP-515. In some embodiments the PD-1 inhibitor is cemiplimab or pembrolizumab.

Cemiplimab, sold under the brand name Libtayo®, is a monoclonal antibody medication for the treatment of squamous cell skin cancer, basal cell carcinoma skin cancer, and Non-small Cell Lung Cancer. Cemiplimab belongs to a class of drugs that binds to the programmed death receptor-1 (PD-1), blocking the PD-l/PD-L1 pathway. In September 2018, it was approved by the U.S. Food and Drug Administration (FDA) for treating people with metastatic cutaneous squamous cell carcinoma (CSCC) or locally advanced CSCC who are not candidates for curative surgery or curative radiation. Cemiplimab is being investigated for the treatment of melanoma cervical cancer, brain cancer, head and neck cancer, renal cell carcinoma, and Hodgkin's lymphoma.

Pembrolizumab (formerly lambrolizumab, sold under the brand name Keytruda®) is a humanized antibody used in cancer immunotherapy. Pembrolizumab was approved for medical use in the United States in 2014. In 2017, the US Food and Drug Administration (FDA) approved it for any unresectable or metastatic solid tumor with certain genetic anomalies (mismatch repair deficiency or microsatellite instability). Approved indication for Keytruda® presently include metastatic melanoma, NSCLC, head and neck cancer, Hodgkin's lymphoma, and metastatic esophageal squamous cell carcinoma among other indications. Pembrolizumab is administered by slow injection into a vein.

3. Thiopurines, such as 6-thioguanine and 6-mercaptopurine, are currently used as anti-inflammatory, antileukemic, and immunosuppressive agents in clinical practice. In activation reactions, 6-thioguanine is converted to 6-thioguanosine monophosphate by the hypoxanthine guanine phosphoribosyltransferase (HPRT) enzyme. Then, 6-thioguanosine monophosphate is further metabolized to 6-thio-2'-deoxyguanosine 5'-triphosphate by kinases and RNA reductases, which may eventually be incorporated into DNA strands during DNA replication. DNA-incorporated 6-thioguanine may also generate reactive oxygen species, which may cause additional damage to DNA, proteins, and other cellular macromolecules, and thus block cellular replication. Although the thiopurines are in clinical use for the treatment of some types of leukemia, their utility for solid tumor treatment has been limited, in part, due to increased toxicities and the development of other therapies.

One particular thiopurine is 6-thio-dG. This compound is a nucleoside analog and has proven to be a telomerase-mediated telomere disrupting compound. As such, cancer cells are very sensitive to 6-thio-dG with observed $IC_{50}$ values ranging from 0.7-2.9 µM, depending on cell type, even including therapy resistant cancers (Mender et al., 2018). The structure is shown below:

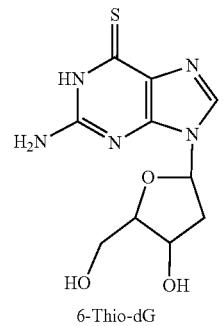 [SMILES: Nc1nc2c(ncn2C2CC(O)C(CO)O2)c(=S)[nH]1]

6-Thio-dG

B. Treatment Regimens

The present disclosure provides for sequential treatment of cancers using 6-thio-dG treatment followed by PD-L1, PD-1 and/or CTLA-4 therapy. The periods for each treatment may vary and it is contemplated that short gap between treatments will be advantageous. For example, the 6-thio-dG treatment may be as little as 2 days but may be 3, 4 or more days, including 2-4 days. The gap prior to PD-L1, PD-1 and/or CTLA-4 treatment should be at least one day and may be up 14 days, such as 2-4 days. An overlap between 6-thio-dG and PD-L1, PD-1 and/or CTLA-4 should be avoided due to potentially detrimental effects of 6-thio-dG on activated effector T cells.

The daily dosage of 6-thio-dG will be between 0.5 mg/kg and 10 mg/kg, preferably intravenous or oral. The dose of PD-L1, PD-1 and/or CTLA-4 will be between be consistent with approved current dosing schedules.

C. Telomerase-Positive Cancers

Telomerase-positive cancers are far more susceptible to the methods of the present disclosure than are telomerase-negative cancers. Therefore, testing a biopsy to determine whether the cancer is or is not telomerase-positive is highly useful, though not required.

The most common methods for detecting telomerase activity are telomeric repeat amplification protocols (TRAPs), which allow one to perform semi-quantitative and quantitative analyses, using some of their modifications (called ddTRAP for droplet digital TRAP). Among these modifications are the scintillation proximity assay, hybridization protection assay, transcription amplification assay, and the magnetic bead-based extraction assay.

The telomeric repeat amplification protocol can be subdivided into three main stages: primer elongation, amplification of telomerase-synthesized DNA, and finally its detection. At the elongation stage, telomeric repeats are added to the telomere-imitating oligonucleotide by telomerase present in the cell extract. PCR-amplification of telomerase-synthesized DNA is carried out with telomere-imitating and reverse primers. Different labels can be incorporated into the telomerase-synthesized DNA. This stage is then followed by detection (e.g., electrophoretic separation and imaging of PCR products).

Still other methods involve the quantitative isolation of telomerase, and the subsequent measurement of the overall activity of the telomerase from a given cell quantity, which can be compared to appropriate standards. A wide variety of labeling and detection methodologies can be employed once telomerase has been isolated and tested in vitro.

D. Drug Resistant Cancers

Antineoplastic resistance, often used interchangeably with chemotherapy resistance, is the resistance of neoplastic (cancerous) cells, or the ability of cancer cells to survive and grow despite anti-cancer therapies. In some cases, cancers can evolve resistance to multiple drugs, called multiple drug resistance.

There are two general causes of antineoplastic therapy failure: Inherent genetic characteristics, giving cancer cells their resistance and acquired resistance after drug exposure, which is rooted in the concept of cancer cell heterogeneity. Characteristics of resistant cells include altered membrane transport, enhanced DNA repair, apoptotic pathway defects, alteration of target molecules, protein and pathway mechanisms, such as enzymatic deactivation. Since cancer is a genetic disease, two genomic events underlie acquired drug resistance: Genome alterations (e.g., gene amplification and deletion) and epigenetic modifications. Cancer cells are constantly using a variety of tools, involving genes, proteins, and altered pathways, to ensure their survival against antineoplastic drugs.

Antineoplastic resistance, synonymous with chemotherapy resistance, is the ability of cancer cells to survive and grow despite different anti-cancer therapies, i.e., their multiple drug resistance. There are two general causes of antineoplastic therapy failure: (i) inherent resistance, such as genetic characteristics, giving cancer cells their resistance from the beginning, which is rooted in the concept of cancer cell heterogeneity; and (ii) acquired resistance after drug exposure.

Since cancer is a genetic disease, two genomic events underlie these mechanisms of acquired drug resistance: Genome alterations (e.g., gene amplification and deletion) and epigenetic modifications.

Chromosomal rearrangement due to genome instability can cause gene amplification and deletion. Gene amplification is the increase in copy number of a region of a chromosome. which occur frequently in solid tumors and can contribute to tumor evolution through altered gene expression.

Hamster cell research in 1993 showed that amplifications in the DHFR gene involved in DNA synthesis began with chromosome break in below the gene, and subsequent cycles of bridge-breakage-fusion formations result in large intrachromosomal repeats. The over amplification of oncogenes can occur in response to chemotherapy, thought to be the underlying mechanism in several classes of resistance. For example, DHFR amplification occurs in response to methotrexate, TYMS (involved in DNA synthesis) amplification occurs in response to 5-fluorouracil, and BCR-ABL amplification occurs in response to imatinib mesylate. Determining areas of gene amplification in cells from cancer patients has huge clinical implications. Gene deletion is the opposite of gene amplification, where a region of a chromosome is lost and drug resistance occurs by losing tumor suppressor genes such as TP53.

Genomic instability can occur when the replication fork is disturbed or stalled in its migration. This can occur with replication fork barriers, proteins such as PTIP, CHD4 and PARP1, which are normally cleared by the cell's DNA damage sensors, surveyors, and responders BRCA1 and BRCA2.

Epigenetic modifications in antineoplastic drug resistance play a major role in cancer development and drug resistance as they contribute to the regulation of gene expression. Two main types of epigenetic control are DNA methylation and histone methylation/acetylation. DNA methylation is the process of adding methyl groups to DNA, usually in the upstream promoter regions, which stops DNA transcription at the region and effectively silences individual genes. Histone modifications, such as deacetylation, alters chromatin formation and silence large chromosomal regions. In cancer cells, where normal regulation of gene expression breaks down, the oncogenes are activated via hypomethylation and tumor suppressors are silenced via hypermethylation. Similarly, in drug resistance development, it has been suggested that epigenetic modifications can result in the activation and overexpression of pro-drug resistance genes.

Studies on cancer cell lines have shown that hypomethylation (loss of methylation) of the MDR1 gene promoter caused overexpression and the multidrug resistance.

In a methotrexate resistant breast cancer cell lines without drug uptake and folate carrier expression, giving DAC, a DNA methylation inhibitor, improved drug uptake and folate carrier expression.

Acquired resistance to the alkylating drug fotemustine in melanoma cell showed high MGMT activity related to the hypermethylation of the MGMT gene exons.

In Imatinib (Gleevec®) resistant cell lines, silencing of the SOCS-3 gene via methylation has been shown to cause STAT3 protein activation, which caused uncontrolled proliferation.

Cancer cells can become resistant to multiple drugs by altered membrane transport, enhanced DNA repair, apoptotic pathway defects, alteration of target molecules, protein and pathway mechanisms, such as enzymatic deactivation.

Many classes of antineoplastic drugs act on intracellular components and pathways, like DNA, nuclear components, meaning that they need to enter the cancer cells. The p-glycoprotein (P-gp), or the multiple drug resistance protein, is a phosphorylated and glycosylated membrane transporter that can shuttle drugs out of the cell, thereby decreasing or ablating drug efficacy. This transporter protein is encoded by the MDR1 gene and is also called the ATP-binding cassette (ABC) protein. MDR1 has promiscuous substrate specificity, allowing it to transport many structurally diverse compounds across the cell membrane, mainly hydrophobic compounds. Studies have found that the MDR1 gene can be activated and overexpressed in response to pharmaceutical drugs, thus forming the basis for resistance to many drugs. Overexpression of the MDR1 gene in cancer cells is used to keep intracellular levels of antineoplastic drugs below cell-killing levels.

For example, the antibiotic rifampicin has been found to induce MDR1 expression. Experiments in different drug resistant cell lines and patient DNA revealed gene rearrangements which had initiated the activation or overexpression of MDR1. A C3435T polymorphism in exon 226 of MDR1 has also been strongly correlated with p-glycoprotein activities.

MDR1 is activated through NF-κB, a protein complex which acts as a transcription factor. In the rat, an NF-κB binding site is adjacent to the mdr1b gene, NF-κB can be active in tumour cells because its mutated NF-κB gene or its inhibitory IκB gene mutated under chemotherapy. In colorectal cancer cells, inhibition of NF-κB or MDR1 caused increased apoptosis in response to a chemotherapeutic agent.

Enhanced DNA repair plays an important role in the ability for cancer cells to overcome drug-induced DNA damages.

Platinum-based chemotherapies, such as cisplatin, target tumor cells by cross-linking their DNA strands, causing mutation and damage. Such damage will trigger programmed cell death (e.g., apoptosis) in cancer cells. Cisplatin resistance occurs when cancer cells develop an enhanced ability to reverse such damage by removing the cisplatin from DNA and repairing any damage done. The cisplatin-resistant cells upregulate expression of the excision repair cross-complementing (ERCC1) gene and protein.

Some chemotherapies are alkylating agents meaning they attach an alkyl group to DNA to stop it from being read. 06-methylguanine DNA methyltransferase (MGMT) is a DNA repair enzyme which removes alkyl groups from DNA. MGMT expression is upregulated in many cancer cells, which protects them from alkylating agents. Increased MGMT expression has been found in colon cancer, lung cancer, non-Hodgkin's lymphoma, breast cancer, gliomas, myeloma and pancreatic cancer.

TP53 is a tumor suppressor gene encoding the p53 protein, which responds to DNA damage either by DNA repair, cell cycle arrest, or apoptosis. Losing TP53 via gene deletion can allow cells to continuously replicate despite DNA damage. The tolerance of DNA damage can grant cancer cells a method of resistance to those drugs which normally induce apoptosis through DNA damage.

Other genes involved in the apoptotic pathway related drug resistance include h-ras and bcl-2/bax. Oncogenic h-ras has been found to increase expression of ERCC1, resulting in enhanced DNA repair (see above). Inhibition of h-ras was found to increase cisplatin sensitivity in glioblastoma cells. Upregulated expression of Bcl-2 in leukemic cells (non-Hodgkin's lymphoma) resulted in decreased levels of apoptosis in response to chemotherapeutic agents, as Bcl-2 is a pro-survival oncogene.

During targeted therapy, oftentimes the target has modified itself and decreased its expression to the point that therapy is no longer effective. One example of this is the loss of estrogen receptor (ER) and progesterone receptor (PR) upon anti-estrogen treatment of breast cancer. Tumors with loss of ER and PR no longer respond to tamoxifen or other anti-estrogen treatments, and while cancer cells remain somewhat responsive to estrogen synthesis inhibitors, they eventually become unresponsive to endocrine manipulation and no longer dependent on estrogen for growth.

Another line of therapeutics used for treating breast cancer is targeting of kinases like human epidermal growth factor receptor 2 (HER2) from the EGFR family. Mutations often occur in the HER2 gene upon treatment with an inhibitor, with about 50% of patients with lung cancer found to have an EGFR-T790M gatekeeper mutation.

Treatment of chronic myeloid leukemia (CML) involves a tyrosine kinase inhibitor that targets the BCR/ABL fusion gene called imatinib. In some people resistant to Imatinib, the BCR/ABL gene is reactivated or amplified, or a single point mutation has occurred on the gene. These point mutations enhance autophosphorylation of the BCR-ABL protein, resulting in the stabilization of the ATP-binding site into its active form, which cannot be bound by imatinib for proper drug activation.

Topoisomerase is a lucrative target for cancer therapy due to its critical role as an enzyme in DNA replication, and many topoisomerase inhibitors have been made. Resistance can occur when topoisomerase levels are decreased, or when different isoforms of topoisomerase are differentially distributed within the cell. Mutant enzymes have also been reported in patient leukemic cells, as well as mutations in other cancers that confer resistance to topoisomerase inhibitors.

One of the mechanisms of antineoplastic resistance is over-expression of drug-metabolizing enzymes or carrier molecules. By increasing expression of metabolic enzymes, drugs are more rapidly converted to drug conjugates or inactive forms that can then be excreted. For example, increased expression of glutathione promotes drug resistance, as the electrophilic properties of glutathione allow it to react with cytotoxic agents, inactivating them. In some cases, decreased expression or loss of expression of drug-metabolizing enzymes confers resistance, as the enzymes are needed to process a drug from an inactive form to an active form. Arabinoside, a commonly used chemotherapy for leukemia and lymphomas, is converted into cytosine arabinoside triphosphate by deoxycytidine kinase. Mutation of deoxycytidine kinase or loss of expression results in resistance to arabinoside. This is a form of enzymatic deactivation.

Growth factor expression levels can also promote resistance to antineoplastic therapies. In breast cancer, drug resistant cells were found to express high levels of IL-6, while sensitive cells did not express significant levels of the growth factor. IL-6 activates the CCAAT enhancer-binding protein transcription factors which activate MDR1 gene expression.

Another type of antineoplastic resistance is resistance to checkpoint inhibitors. Primary resistance to immune checkpoint blockade occurs in approximately 40% to 65% of patients with melanoma treated with anti-PD-1 based therapy. This clinical problem occurs when there is failure to induce an effective antitumor immune response at any of the three stages of the cancer immune cycle. To date, the factors that have been associated with primary resistance include elevated levels of baseline serum LDH, increased baseline tumor burden, lack of PD-L1 expression in baseline melanoma tissue samples, lack of T-cell infiltration, the absence of PD-1 T cells and PD-L1 macrophages in melanoma biopsies taken early during treatment, insufficient neoantigens and low mutational burden, the presence of an innate anti-PD-1 resistance signature (IPRES) transcriptional signature, or absence of an interferon signature.

Acquired resistance to immunotherapy can develop when there is a selection of subpopulations of tumor cells with genetic and epigenetic traits that allow them to evade the immune system. An example is the loss of B2M expression was reported in melanoma cell lines from patients who had been treated with immunotherapy and cytokine-gene therapy. This resulted in a loss of MHC class I expression and, therefore, a subsequent decrease in recognition by CD8• T cells. JAK1/2 mutations have also recently been identified as genetic markers of acquired resistance to immunotherapy in melanoma. These mutations in tumor cells lead to decreased sensitivity to IFN-γ, ultimately preventing IFN-γ-induced cell growth arrest. Loss-of-function mutations in the genes encoding JAK1 or JAK2 were found in relapsed tumors following whole-exome sequencing of baseline and progression biopsies; all patients had an objective response to treatment with pembrolizumab and then progressed. In addition, acquired resistance can also occur on the level of the individual cells, where tumor cells alter their gene expression in response to immune molecules within the tumor microenvironment. For example, PD-L1 can be upregulated by tumor cells in response to immune cytokines, such as IFN-γ released by T cells, hence limiting T-cell function, and can occur in both primary and acquired resistance.

III. PHARMACEUTICAL FORMULATIONS AND ROUTES OF ADMINISTRATION

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render drugs stable and allow for uptake by target cells. Aqueous compositions of the present disclosure comprise an effective amount of the drug dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the agents of the compositions.

The active compositions of the present disclosure may include classic pharmaceutical preparations. Administration of these compositions according to the present disclosure may be via any common route so long as the target tissue is available via that route, but generally including systemic administration. This includes oral, nasal, or buccal. Alternatively, administration may be by intradermal, subcutaneous, intramuscular, intraperitoneal or intravenous injection, or intratumoral or regional to a tumor, such as in the tumor vasculature. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present disclosure generally may be formulated in a neutral or salt form. Pharmaceutically acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IV. COMBINED THERAPY

In the context of the present disclosure, it also is contemplated 6-thio-dG/anti PD-L1 such as atezolizumab or 6-thio-dG/anti PD-1 such as Libtayo® or anti CTAL-4 could be used in conjunction with chemo- or radiotherapeutic intervention, or other treatments. It also may prove effective, in particular, to combine 6-thio-dGanti PD-L1, anti PD-1 or anti CTLA-4 with other therapies that target different aspects of cancer cell function.

To kill cells, inhibit cell growth, inhibit metastasis, inhibit angiogenesis or otherwise reverse or reduce the malignant phenotype of tumor cells, using the methods and compositions of the present disclosure, one would generally contact a "target" cell with 6-thio-dG and at least one other agent. These compositions would be provided in a sequential or combined amount effective to kill or inhibit proliferation of the cell. This process may involve contacting the cells with 6-thio-dG/anti PD-L1, anti PD-1 or anti CTLA-4 and the other agent(s) or factor(s) at the same time. This may be achieved by contacting the cell with a single composition or pharmacological formulation that includes both agents, or by contacting the cell with two distinct compositions or formulations, at the same time, wherein one composition includes the interferon prodrugs according to the present disclosure and the other includes the other agent.

Alternatively, the 6-thio-dG/anti PD-L1, anti PD-1 or anti CTLA-4 therapy may precede or follow the other agent treatment by intervals ranging from minutes to weeks. In embodiments where the other agent and the interferon prodrugs are applied separately to the cell, one would generally ensure that a significant period of time did not expire between each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either interferon prodrugs or the other agent will be desired. Various combinations may be employed, where 6-thio-dG/anti PD-L1, anti PD-1 or anti CTLA-4 therapy is "A" and the other therapy is "B", as exemplified below:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are contemplated. Again, to achieve cell killing, both agents are delivered to a cell in a combined amount effective to kill the cell.

Agents or factors suitable for cancer therapy include any chemical compound or treatment method that induces DNA damage when applied to a cell. Such agents and factors include radiation and waves that induce DNA damage such as, irradiation, microwaves, electronic emissions, and the like. A variety of chemical compounds, also described as "chemotherapeutic" or "genotoxic agents," may be used. This may be achieved by irradiating the localized tumor site; alternatively, the tumor cells may be contacted with the agent by administering to the subject a therapeutically effective amount of a pharmaceutical composition.

Various classes of chemotherapeutic agents are contemplated for use with the present disclosure. Imetelstat is discussed below. Other chemotherapeutics include selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene. The agents camptothecin, actinomycin-D, and mitomycin C are commonly used chemotherapeutic drugs. The disclosure also encompasses the use of a combination of one or more DNA damaging agents, whether radiation-based or actual compounds, such as the use of X-rays with cisplatin or the use of cisplatin with etoposide. The agent may be prepared and used as a combined therapeutic composition.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21-day intervals for doxorubicin, to 35-50 mg/m$^2$ for etoposide intravenously or double the intravenous dose orally. Microtubule inhibitors, such as taxanes, also are contemplated. These molecules are diterpenes produced by the plants of the genus Taxus and include paclitaxel and docetaxel.

Epidermal growth factor receptor inhibitors, such as Iressa, mTOR, the mammalian target of rapamycin (also known as FK506-binding protein 12-rapamycin associated protein 1 (FRAP1)), is a serine/threonine protein kinase that regulates cell growth, cell proliferation, cell motility, cell survival, protein synthesis, and transcription. Rapamycin and analogs thereof ("rapalogs") are therefore contemplated for use in cancer therapy in accordance with the present disclosure. Another EGFR inhibitor of particular utility here is Gefitinib.

Another possible therapy is TNF-αc (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In addition, it also is contemplated that a distinct immunotherapy, a hormone therapy, a toxin therapy and/or surgery can be used.

The skilled artisan is directed to "Remington's Pharmaceutical Sciences" 15th Edition, Chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. EXAMPLES

The following Examples section provides further details regarding examples of various embodiments. It should be appreciated by those of skill in the art that the techniques disclosed in the examples that follow represent techniques and/or compositions discovered by the inventors to function well. However, those of skill in the art should, in light of the present disclosure, appreciate that many changes can be made in the specific embodiments which are disclosed and still obtain a like or similar result without departing from the spirit and scope of the disclosure. These examples are illustrations of the methods and systems described herein and are not intended to limit the scope of the disclosure. Non-limiting examples of such include but are not limited to those presented below.

Example 1—Materials and Methods

Mice. Female C57BL/6J, BALB/c, Myd88−/−, Tmem173−/−, Batf3−/− and OT-1 CD8+ T cell receptor transgenic mice in the C57BL/6J background and NSG-SMG3 mice were purchased from The Jackson Laboratory. Rag1−/− mice and IFN reporter mice (Ifng$^{tm3.1Lky}$/J) on C57BL/6 background were purchased from UT southwestern mice breeding core. Ifnar1−/− mice were provided by Dr. Anita Chong from the University of Chicago. All mice were maintained under specific pathogen-free conditions. Animal care and experiments were carried out under institutional and National Institutes of Health protocol and guidelines. This study has been approved by the Institutional Animal Care and Use Committee of the University of Texas Southwestern Medical Center.

Cell lines and reagents. MC38, CT26, LLC A375 and HCT116 cells were purchased from ATCC. MC38-OVA cells were made by lenti-viral transduction of OVA gene. All cell lines were routinely tested using mycoplasma contamination kit (R&D) and cultured in Dulbecco's modified Eagle's medium supplemented with 10% heat-inactivated fetal bovine serum, 100 U/ml penicillin, and 100 U/ml streptomycin under 5% $CO_2$ at 37° C.

Anti-CD4 (GK1.5), anti-NK1.1 (PK136), anti-CD8 (53-5.8) and anti-CSF1R (AFS98) mAbs were purchased from BioXCell. Anti-PD-L1 (Atezolizumab) and anti-CTLA-4 (Ipilimumab) were kindly provided by UT Southwestern Simmons Cancer Center Pharmacy. 6-thio-dG was purchased from Metkinen Oy. For in vitro studies, 6-thio-dG was dissolved in DMSO/water (1:1) to prepare 10 mM stock solutions. For in vivo studies, 3 mg/kg 6-thio-dG was prepared in 5% DMSO (in 1×PBS) for intraperitoneal injection. Drugs were kept frozen at −20° C. until use.

Cell viability assay. For determination of $IC_{50}$ with cell proliferation assays, murine and human cancer cell lines were screened with 6-thio-dG with a 2-fold dilution series in 8 different points in 96-well plates. Cells were plated 24 hrs prior to the addition of drug, incubated for 4-5 days, and assayed using CellTiter 96® Aqueous One Solution Cell Proliferation Assay according to the manufacturer's instructions (Promega). Cell number per well ranged from 1,000 to 10,000 cells per well inversely proportional to doubling times. Dose response curves were generated and $IC_{50}$s calculated using Graphpad Prism. All samples were analyzed in triplicate and standard deviations are from 2-3 independent experiments.

Colony formation assay. MC38 cells were seeded in three different concentrations on six well plates (1000-4000 cells/well) and treated with various drug concentrations every 3-4 days. Following 13 days treatment, cells were fixed and stained with 6% glutaraldehyde (Fisher Scientific) plus 0.5% crystal violet (Sigma) solution. After washing with tap water, cells were air-dried and images captured using a G-BOX (Syngene, model: G-BOX F3).

Telomere dysfunction Induced Foci (TIF) and micronuclei assays. The TIF assay is based on the co-localization detection of DNA damage by an antibody against DNA damage response factors such as gamma-H2AX, 53BP1, and antibody against telomeric proteins or telomeres using telomere sequence-specific peptide nucleic acid (PNA) probe (Mender and Shay, 2015). Briefly, cells were seeded into 4-well chamber slides. Next day, cells were treated with 1 μM 6-thio-dG for 24 hrs (for TIF assay) or 1-3 μM 6-thio-dG for 48 hrs (for micronuclei assay). Slides were then rinsed twice with PBS and fixed in 4% formaldehyde (Thermo Fisher) in PBS for 10 mins. Then, cells were washed twice with PBS and permeabilized in 0.5% Triton X-100 in PBS for 10 min. Following permeabilization, cells were washed three times with PBS. Cells were blocked with 10% goat serum in 0.1% PBST (TritonX-100) for 1 hr. Gamma-H2AX (TIF assay, mouse, 1:1000) (Millipore) or lamin A/C (micronuclei assay, mouse, 1:500) (Santa Cruz) was diluted in blocking solution and incubated on cells for 2 hrs. Following three washes with PBST (1×PBS in 0.1% Triton) and 3 washes with PBS, cells were incubated with Alexaflour 568 conjugated goat anti-mouse (1:500) (Invitrogen) for 40 mins, then washed five times with 0.1% PBST. Cells were fixed in 4% formaldehyde in PBS for 20 mins at RT. The slides were sequentially dehydrated with 70%, 90%, 100% ethanol followed by denaturation with hybridization buffer containing FAM-conjugated telomere sequence (C-rich)-specific PNA probe, 70% formamide, 30% 2×SSC, 10% (w/v) $MgCl_2 \cdot 6H_2O$ (Fisher Sci), 0.25% (w/v) blocking reagent for nucleic acid hybridization and detection (Roche) for 7 mins at 80° C. on a heat block, followed by overnight incubation at RT. Slides were washed sequentially with 70% formamide (Ambion)/0.6×SSC (Invitrogen) (2×1 hr), 2×SSC (1×15 mins), PBS (1×5 mins) and sequentially dehydrated with 70%, 90%, 100% ethanol, then mounted with Vectashield mounting medium with DAPI (Vector Laboratories). Images were captured with a fluorescein microscope using the 100× objective. TIFs were quantified using Image J.

Detection of DNA in Bone Marrow Derived Dendritic Cells. Cells were labeled with EdU as described previously (Min et al., 2019). Briefly, 100,000 MC38 cells were seeded to 6-well plate and labeled with 25 μM EdU. Two days later, cells were washed out and treated with 1 μM 6-thio-dG for 24 hrs. Cells were washed out again and co-cultured with BMDCs for overnight. Next day, DCs were sorted out with magnetic beads, washed, fixed and cytospun. Slides were then stained with 6-carboxytetramethlyrhodamine fluorescent azide (Invitrogen) in fresh homemade EdU-staining solution (PBS containing 1 mM $CuSO_4$, 2 mM ascorbic acid) for 30 min. Slides were then washed vigorously with PBS for at least 1 hr, and then telomere FISH steps using a FAM-TelG probe were followed as described in "Telomere dysfunction Induced Foci (TIF) and micronuclei assays" method parts. Images were captured at 63× magnification with an Axio Imager Z2 equipped with an automatic metaphase capture system (Coolcubel camera) and analyzed with ISIS software (Metasystems).

ImmunoFISH. Briefly, 5 μM tissue sections were deparaffinized with xylene (2×5 mins), 100% ethanol (2×2 mins), 95% ethanol (1×2 mins), 75% ethanol (1×2 mins), and 50% ethanol (1×2 mins) and then washed with tap water (2×3 mins). Deparaffinized tissue sections were incubated in sodium citrate buffer (10 mM Na-citrate, 0.05% Tween 20, pH=6.0) at microwave for 20 mins to retrieve antigens. After tissue sections cooled down, they were rinsed with 1×PBS for 5 mins and then dehydrated in 95% ethanol for 3 mins. Denaturation was conducted with hybridization buffer (70% formamide, 30% 2×SSC, 10% (w/v) $MgCl_2·6H_2O$ (Fisher Sci), 0.25% (w/v) blocking reagent (Roche)) containing FITC-conjugated telomere sequence $(TTAGGG)_3$-specific PNA probe for 7 mins at 80° C. on a heat block. Slides were washed sequentially with 70% formamide/0.6×SSC (3×15 mins), 2×SSC (1×15 mins), PBS (1×5 mins), PBST (PBS+0.1% Tween 20; 1×5 mins) and incubated with blocking buffer (4% BSA in PBST) for 30 mins. Sections were incubated with phospho-histone H2AX antibody (1:500) (Cell Signaling) in blocking buffer at RT for 1 hr. Following 2×5 mins washes with PBST, tissue sections incubated with Alexaflour 568 conjugated goat anti-Rabbit in blocking buffer at RT for 1 hr. Sections were washed sequentially with PBST (3×5 mins) and PBS (1×5 mins). The slides were mounted with Vectashield mounting medium with DAPI. Images were captured with a fluorescein microscope using a 100× objective. TIFs were quantified using Image J.

Tumor growth and treatment. A total of $5×10^5$ MC38, $5×10^5$ CT26 or $1×10^6$ LLC cells were inoculated subcutaneously into right dorsal flanks of the mice in 100 μL phosphate buffered saline (PBS). Tumor-bearing mice were randomly grouped into treatment groups when tumors grew to around 100 $mm^3$. For 6-thio-dG single treatment, 3 mg/kg 6-thio-dG was intraperitoneally given on days 7, 8 and 9 in MC38 tumor and LLC tumor and on days 5, 6, 7 for CT26 tumor. For CSF1R, NKL.1, CD4+ and CD8+ T cell depletion, 200 μg of antibodies were intraperitoneally injected 1 day before treatment initiation and then twice a week for 2 weeks. For PD-L1 blockade combination therapy in MC38 model, 6-thio-dG was given on day 10 and day 11, 50 μg PD-L1 was intraperitoneally injected on day 13 and 17. For PD-L1 blockade combination therapy in LLC model, 6-thio-dG was given on day 4, 5, 6, 10 and 11, 200 μg PD-L1 was intraperitoneally injected on day 8 and 13. Tumor volumes were measured by the length (a), width (b) and height (h) and calculated as tumor volume=abh/2.

Humanized mouse tumor models. Humanized mouse reconstitution was previously described (Qiao et al., 2019). Briefly, four-week-old NSG-SGM3 female mice were irradiated with 100 cGy (X-ray irradiation with X-RAD 320 irradiator) one day prior to human CD34+ cells transfer. Cord blood was obtained from UT Southwestern Parkland Hospital. Human CD34+ cells were purified from cord blood by density gradient centrifugation (Ficoll® Paque Plus, GE healthcare) followed by positive immunomagnetic selection with anti-human CD34 microbeads (Stemcell). $1×10^5$ CD34+ cells were intravenously injected into each recipient mouse. 12 weeks after engraftment, humanized mice with over 50% human CD45+ cells reconstitution and age and sex matched non-humanized mice were inoculated with $1×10^6$ HCT116 tumor cells subcutaneously on the right flank. 3 mg/kg 6-thio-dG was intraperitoneally given on days 7, 8 and 9. Tumor volumes were measured twice a week. Experiments were performed in compliance with UTSW Human Investigation Committee protocol and UTSW Institutional Animal Care and Use Committee.

Tmem173 and Mb21d1 knockout MC38 cell line. Tmem173 and Mb21d1 genes in MC38 cells were knocked out by CRISPR/Cas9 technology. The guide sequence 5'-CACCTAGCCTCGCACGAACT-3' (SEQ ID NO: 1) for Tmem173 and 5'-CGCAAAGGGGGGCTCGATCG-3' (SEQ ID NO: 2) for Mb21d1 were cloned into px458 plasmids (non-integrating plasmid with GFP selecting marker), and then were transiently transfected into tumor cells using lipofectamine 2000 (Thermo Fisher). 24 hrs later, GFP positive cells were sorted and cultured for another one week. Then sorted cells were seeded into 96-well plates. Another week later, GFP negative clones were passed into 12-well plate, and western blot was performed to identify the knock-out clones. Finally, all knock-out clones were pooled together for experiments.

IFN-γ enzyme-linked immunosorbent spot assay (ELISPOT). MC38 tumors were injected subcutaneously on the right flank of C57BL/6. For 6-thio-dG single treatment, 3 mg/kg 6-thio-dG was intraperitoneally given on days 7, 8 and 9; for PD-L1 blockade combination therapy in MC38 model, 3 mg/kg 6-thio-dG was given on day 10 and day 11, 50 μg PD-L1 was intraperitoneally injected on day 11. 7 days after last treatment, tumor draining lymphoid and spleen from tumor-bearing mice were collected and single-cell suspension was prepared. Irradiated MC38 tumor cells and control LLC tumor cells were used to re-stimulate the tumor-specific T cells. $1.5×10^5$ draining lymph nodes cells or splenocytes and $7.5×10^4$ irradiated tumor cells were co-cultured for 48 hrs, and ELISPOT assay was performed using the IFN-γ ELISPOT kit (BD Bioscience) according to the manufacturer's instructions. IFN-γ spots were enumerated with the CTL-ImmunoSpot® S6 Analyzer (Cellular Technology Limited).

In vitro co-culture of bone marrow dendritic cells (BMDC) and T cells. Single-cell suspensions of bone marrow (BM) cells were collected from tibias and femurs of C57BL/6 mice. The BM cells were placed in 10 cm dish and cultured with complete RPMI 1640 medium containing 20 ng/mL recombinant mouse GM-CSF (BioLegend). Fresh medium with was added into the culture on day 3 and day 6. The BMDCs were harvested Day 7. CD8+ T cells were isolated from lymph nodes and spleens of OT-1 transgenic mice with a negative CD8+ T cell isolation kit (Stemcell). MC38-OVA cells pretreated with 200 nM 6-thio-dG for 4 hrs. Then the drug was washed out, tumor cells were continued to culture for 72 hrs and were harvested on the same day as BMDC harvest. Then MC38-OVA cells were co-cultured with BMDC for overnight. Supernatant was collected for IFN-β ELISA test (PBL). BMDCs were sorted with CD11c+ positive selection kit (Stemcell) and co-cultured with OT-1 CD8+ T cells for 48 hrs. Supernatants were collected and IFN-γ was measured by cytometric bead array assay (BD Biosciences).

Cytosolic DNA extraction and quantitative real-time PCR. HCT 116 cells were pretreated with 500 nM 6-thio-dG for 4 hrs. Then drug was washed out, tumor cells were continued to culture for 72 hrs and harvest on the same day as BMDC harvest. Then HCT116 cells were mixed 1:1 with $1 \times 10^6$ BMDC for 4 hrs. BMDC was purified and divided into two equal aliquots.

One aliquot was extracted for total genomic DNA with Purelink Genomic DNA kit (Invitrogen) and served as normalization control. The other aliquot was resuspended in 100 μL cytosolic extract buffer containing 150 mM NaCl, 50 mM HEPES and 25 mg/mL digitonin (Sigma) and incubated for 10 mins at RT for plasma membrane permeabilization (West et al., 2015). Then cells were centrifuged to pellet intact cells. The cytosolic supernatants were collected and centrifuged at 12000 g for 10 mins to pellet the remaining cellular debris. Then cytosolic DNA was extracted with Purelink Genomic DNA kit (Invitrogen). Quantitative PCR was performed on both whole-cell extracts and cytosolic fractions using human DNA primers and mouse DNA primers (Xu et al., 2017).

Tumor digestion. Tumor tissues were excised and digested with 1 mg/mL Collagenase I (Sigma) and 0.5 mg/mL DNase I (Roche) in the 37° C. for 30 mins, tumor was then passed through a 70 μm cell strainer to remove large pieces of undigested tumor. Tumor infiltrating cells were washed twice with PBS containing 2 mM EDTA.

Flow cytometry analysis. Single cell suspensions of cells were incubated with anti-FcγIII/II receptor (clone 2.4G2) for 15 minutes to block the non-specific binding before staining with the conjugated antibodies, and then incubated with indicated antibody for 30 mins at 4° C. in the dark. Fixable viability Dye eFlour 506 or eFlour780 (eBioscience) was used to exclude the dead cells. Foxp3 and Ki67 were stained intracellularly by using True-Nuclear transcription factor buffer set (BioLegend) following the manufacturer's instructions. Data were collected on CytoFLEX flow cytometer (Beckman Coulter, Inc) and analyzed by using FlowJo (Tree Star Inc., Ashland, OR) software.

Quantitative real-time PCR. Real-time PCR was performed with SsoAdvanced™ Universal SYBR® Green Supermix (Bio-Rad) according to the manufacturer's instructions with different primer sets (human MT-CO1, forward primer 5'-CGCCACACTCCACGGAAGCA-3' (SEQ ID NO: 3), reverse primer 5'-CGGGGCATTCCG GATAGGCC-3' (SEQ ID NO: 4); human18s rRNA, forward primer 5'-ACCGATTGGATGGTTTAGTGAG-3' (SEQ ID NO: 5), reverse primer 5'-CCTACGGAAACCTTGT-TACGAC-3' (SEQ ID NO: 6); mouse IFN-β, forward primer 5'-ATGAGTGGTGGTTGCAGGC-3' (SEQ ID NO: 7), reverse primer 5'-TGACCTTTCAAATGCAGTAGATTCA-3' (SEQ ID NO: 8); mouse GAPDH, forward primer 5'-CAT-CAAGAA GGTGGTGAAGC-3' (SEQ ID NO: 9), reverse primer 5'-CCTGTTGCTGTAGCCGTATT-3') (SEQ ID NO: 10) mouse GAPDH was used as the internal control. $2^{-\Delta\Delta Ct}$ method was used to calculate relative expression changes.

Immunoblotting. BMDC and MC38 treatment were same as "In vitro co-culture of bone marrow dendritic cells". 6 hrs after co-culture, DC was isolated with CD11c+ positive selection kit (Stemcell). Protein sample preparation and immunoblot procedures were performed as previously described (Liu et al., 2019). Proteins were detected with rabbit monoclonal antibodies for pSTING (Cell signaling, 72971), STING (Cell signaling, 50494), pTBK1 (Cell signaling, 5483), TBK1 (Cell signaling, 3504). Protein loading was determined with antibodies against with Cyclophilin A (Cell signaling, 2175). Anti-rabbit (1:2000 in 5% BSA) was used for secondary antibody (Cell signaling, 7074). X-ray film (GeneMate, F-9024-8X10) was used to develop the membranes. Clarity Max Western ECL Substrate (Biorad, 1705062) or Supersignal West PicoPlus Chemiluminescent Substrate (Thermoscientific, 34577) was used for chemiluminescent western blot.

Quantification and Statistical Analysis. All the data analyses were performed with GraphPad Prism statistical software and shown as mean±SEM. P value determined by two-way ANOVA for tumor growth or Log-rank test for survival or unpaired two-tailed t-tests for other analysis. A value of p<0.05 was considered statistically significant.

Example 2—Results

Figure 1A:
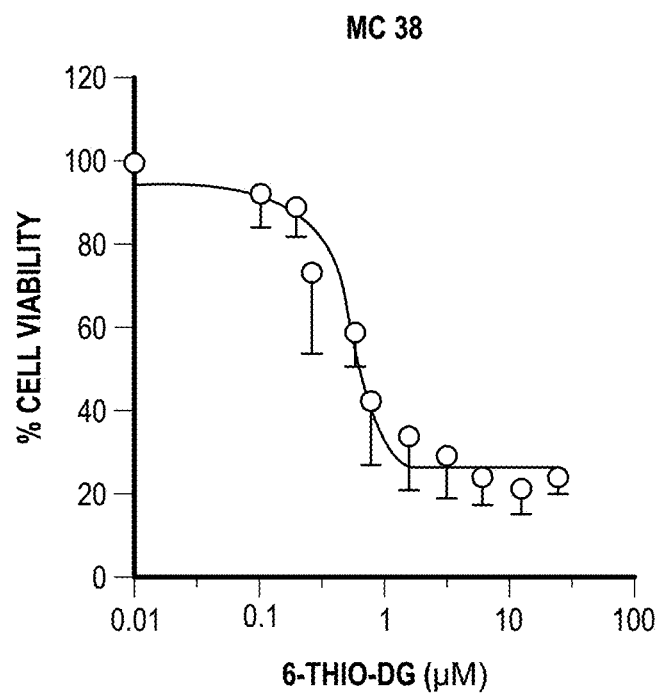
FIGS. 1A-G. The therapeutic effect of 6-thio-dG depends on CD8+ T cells.
Figure 1B:
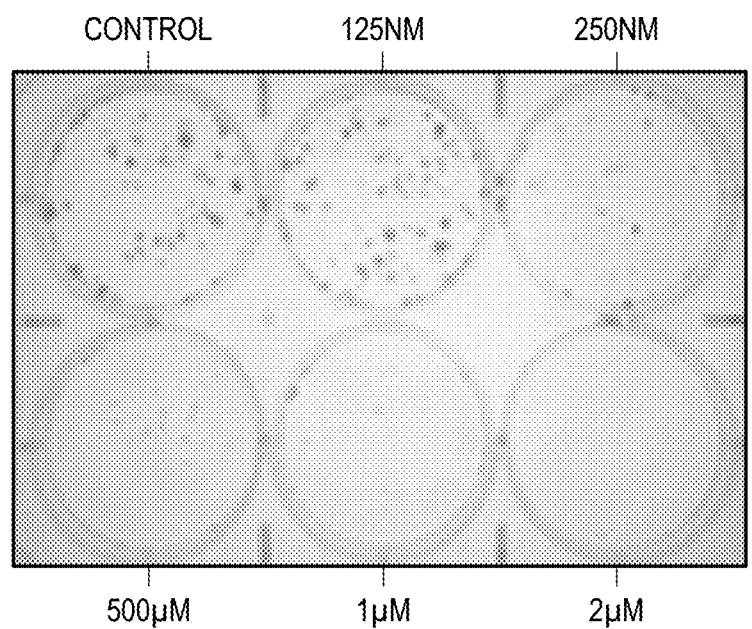
Figure 1C:
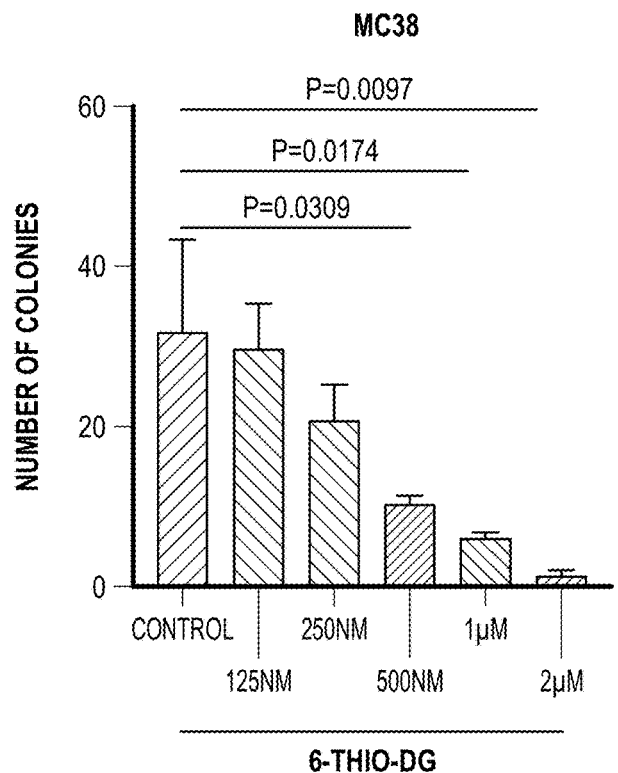
Figure 1D:
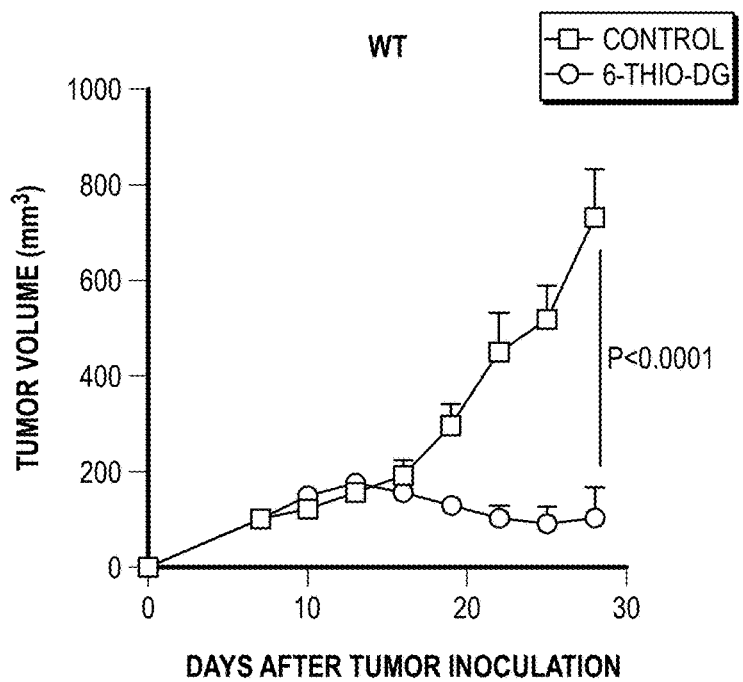

The therapeutic effect of 6-thio-dG depends on CD8+ T cells. All previous studies with xenograft models showed that intensive daily treatment with 6-thio-dG over 10 days could partially control tumor growth in many tumor models (Mender et al., 2015a; Mender et al., 2018; Zhang et al., 2018). However, the potential role of this drug on interaction between tumors and the adaptive immune system is unknown. In order to explore whether 6-thio-dG induces telomere-based DNA sensing for T cell responses, the inventors first determined the inhibition of cell viability by 6-thio-dG on telomerase-positive murine colon cancer cells (MC38) in immunocompetent host. MC38 tumor cells are sensitive to 6-thio-dG with an $IC_{50}$ concentration of 370 nM (FIG. 1A). They also confirmed 6-thio-dG sensitivity in MC38 cells by a separate colony formation assay. MC38 cells treated with 6-thio-dG every three days for 13 days, resulted in less than 50% of the cells forming colonies with 0.5 μM 6-thio-dG treatment (FIGS. 1B and 1C). To evaluate whether 6-thio-dG reduces tumor burden in syngeneic mouse models in vivo, the inventors subcutaneously inoculated MC38 cell into immunocompetent wild-type (WT) C57BL/6 mice. Seven days after tumor inoculation (when the tumor volume was ~100 mm³), 3 mg/kg 6-thio-dG was administered daily for only three days and tumor growth was significantly reduced (FIG. 1D) compared to the control tumor. This was not a unique response to MC38 tumor model as the inventors also observed cell viability inhibition in vitro and significant tumor growth delay in vivo in telomerase-positive LLC (Lewis lung murine carcinoma derived from the C57BL/6 mouse) and CT26 (Colon murine carcinoma derived from the BALB/C mouse) tumor models with only three days treatment (FIGS. 9A-D).

Figure 1E:
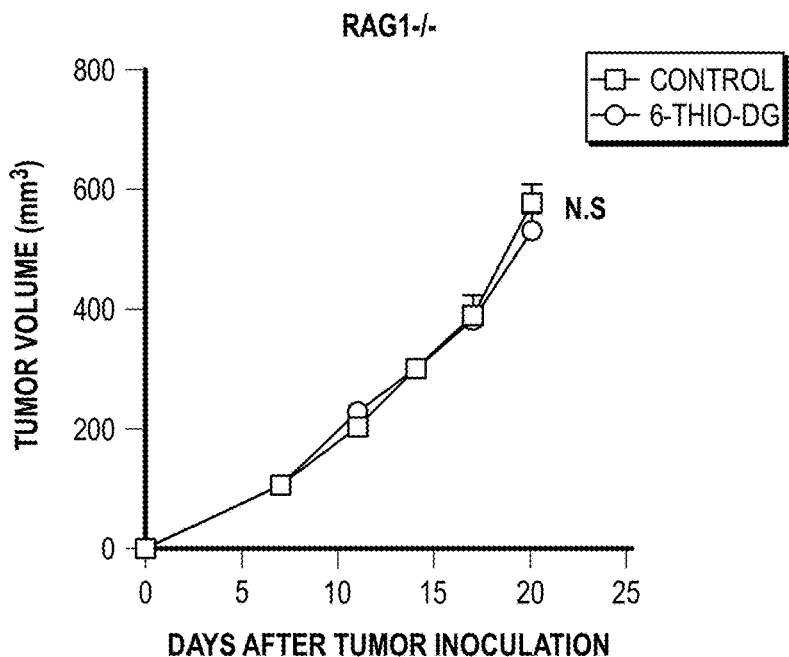
Figure 1F:
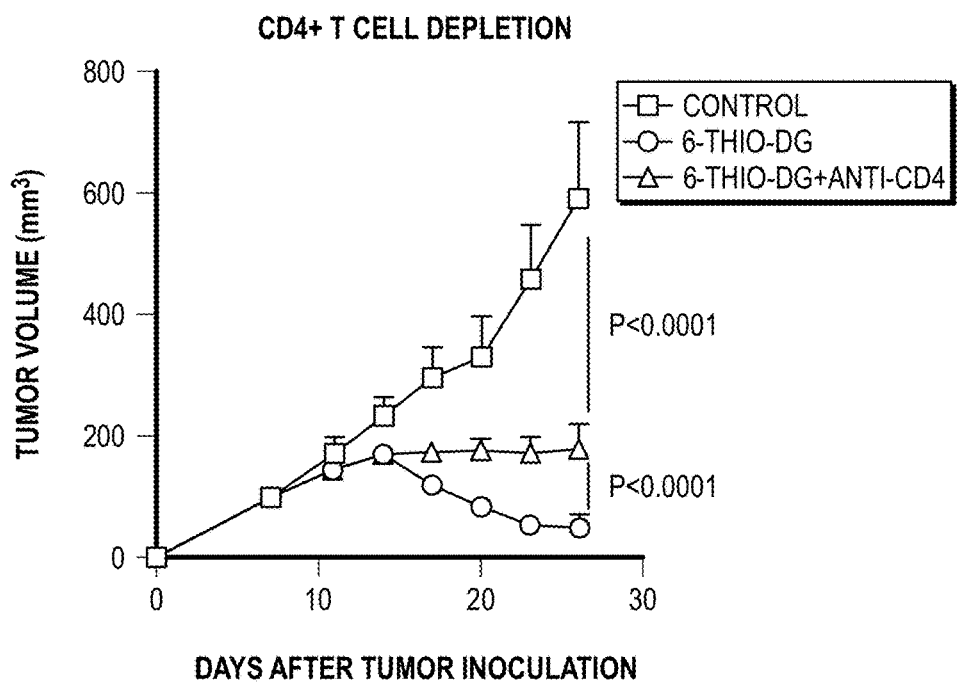
Figure 1G:
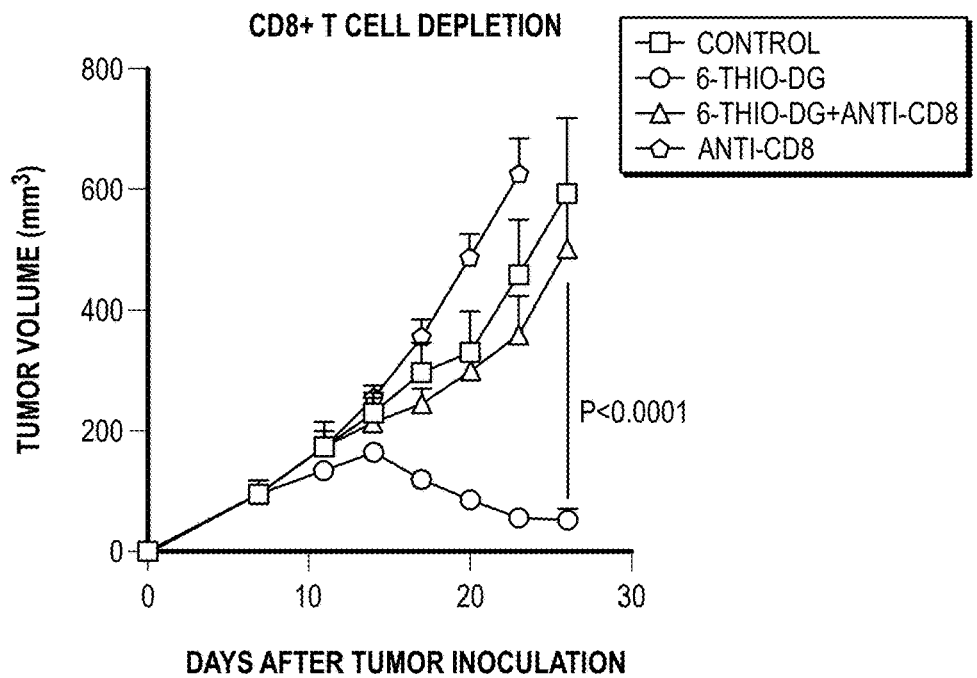
Figure 2A:
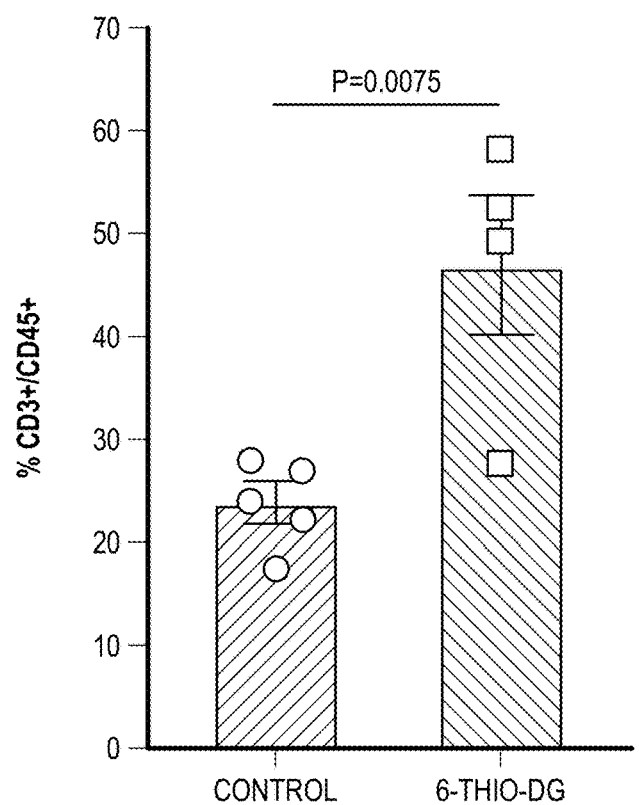
FIGS. 2A-F. 6-thio-dG treatment increases tumor-specific T cell response.
Figure 2B:
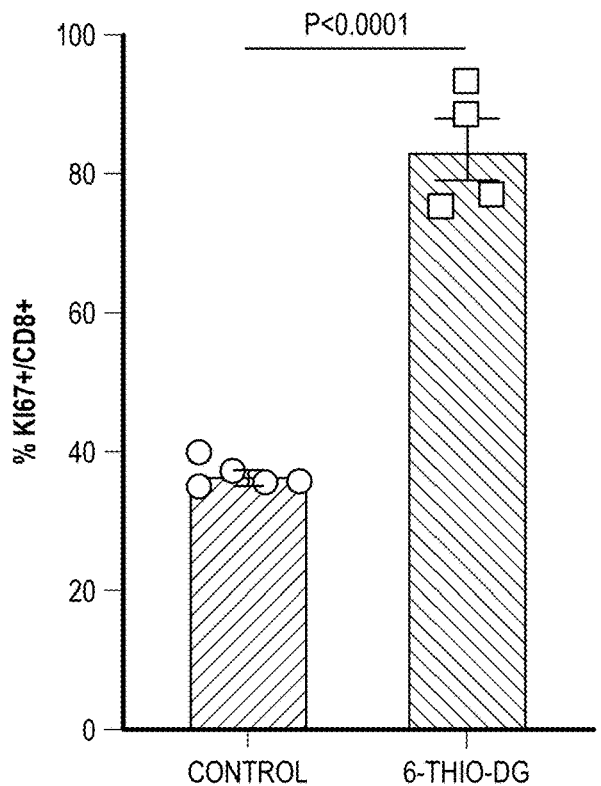
Figure 10A:
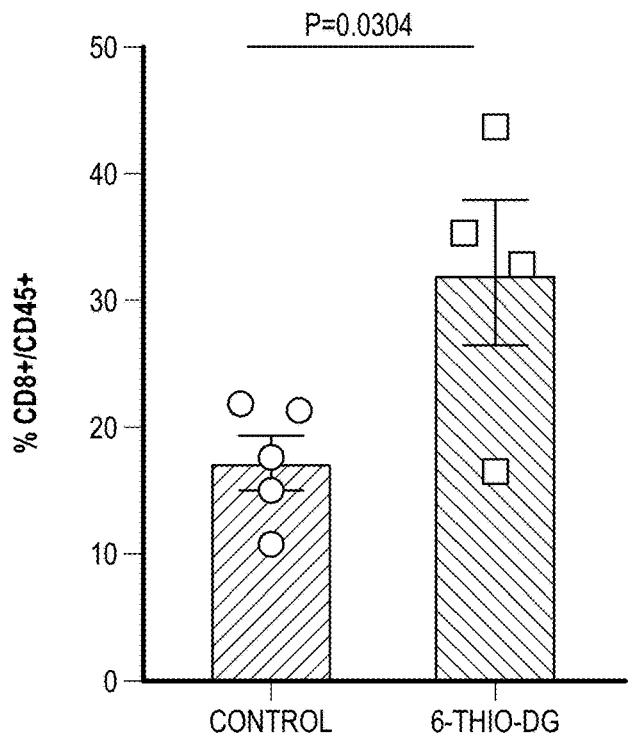
FIGS. 10A-F (related to FIGS. 2A-G).
Figure 10B:
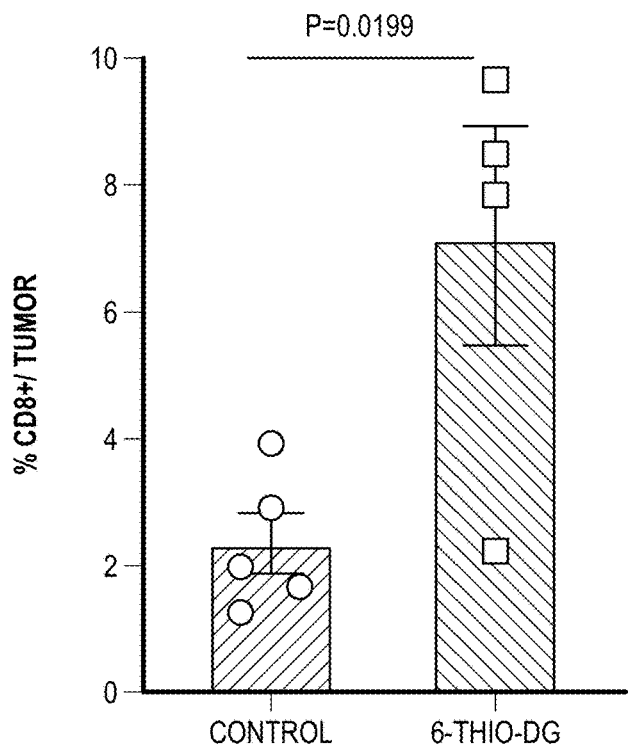
Figure 10C:
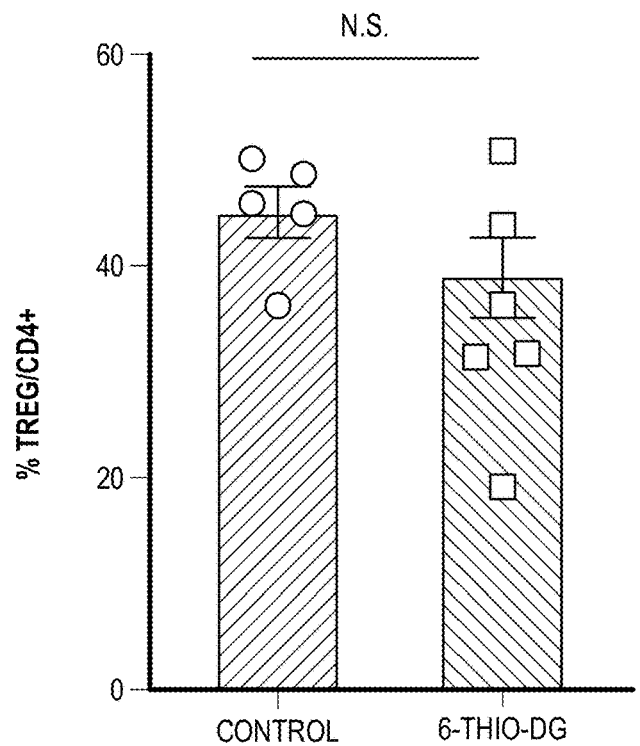
Figure 10D:
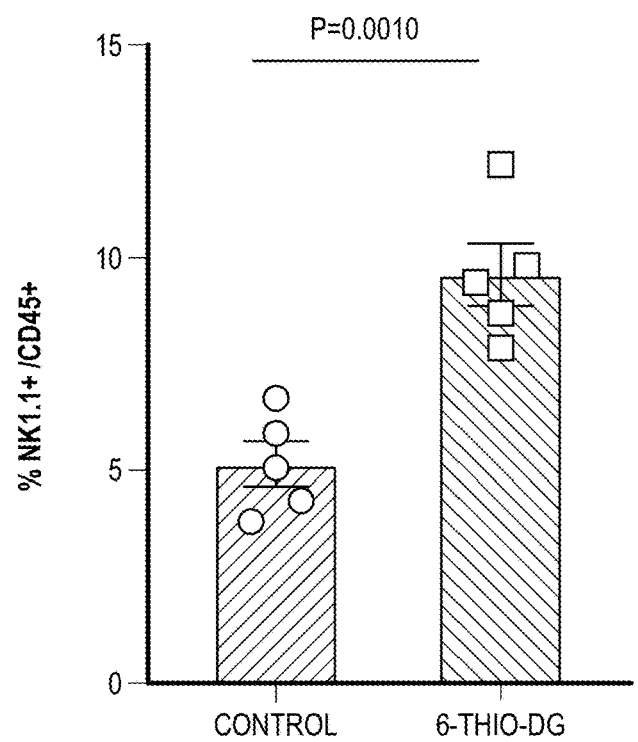
Figure 10E:
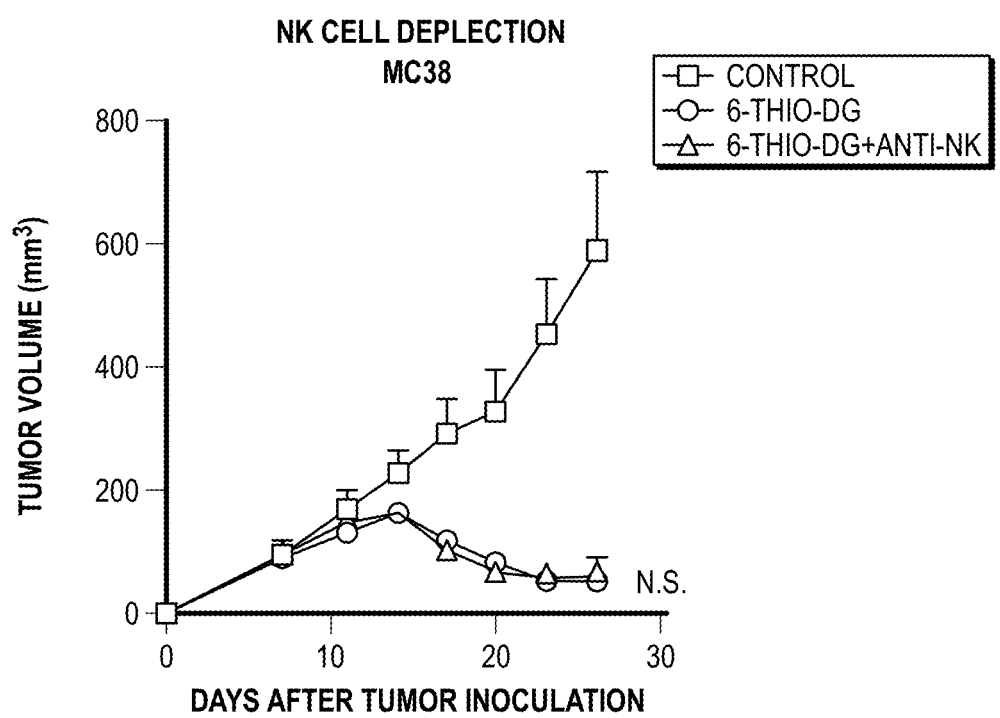

Because the inventors gave such a short duration of treatments with 6-thio-dG compared to the intensive dosing strategy in xenograft models (5 mg/kg, daily for two weeks) and achieved better anti-tumor effect in the syngeneic mouse models, they speculated that 6-thio-dG might have an immune stimulatory role in vivo. Therefore, they inoculated tumors on Rag1 knock out mice that cannot generate mature T and B cells. Indeed, the therapeutic effect of 6-thio-dG was completely diminished (FIG. 1E), indicating adaptive immune cells are largely required for tumor control in vivo. To find out which subset of T cells contributes to the 6-thio-dG-mediated anti-tumor effect, the inventors depleted CD4+ or CD8+ T cells while giving 6-thio-dG treatment and observed a marginal influence of CD4+ T cell depletion (FIG. 1F). However, depletion of CD8+ T cells completely abolished the therapeutic effect of 6-thio-dG (FIG. 1G). Together the data can be interpreted to suggest an essential role of CD8+ T cells in 6-thio-dG treatment. 6-thio-dG treatment increases tumor-specific T cell response. As the therapeutic effect of 6-thio-dG depends on T cells, the inventors reasoned that 6-thio-dG treatment might change immune cell expansion in the tumor microenvironment. To test this, they analyzed the number of tumor infiltrating lymphocytes (TILs) 6 days after the last of three daily doses of 6-thio-dG treatment. The inventors found an increase in the frequency of CD3+ T cells and CD8+ T cells in TILs after 6-thio-dG treatment (FIGS. 2A, 10A and 10B). They also observed a significant upregulation of CD8+ T cell proliferation indicated by elevated Ki67 expression (FIG. 2B), but no significant changes of Treg cells (FIG. 10C). Although tumor infiltrating NK cells were also increased, the inventors did not see an impact of NK cell depletion on the therapeutic effect of 6-thio-dG (FIGS. 10D and 10E). Together with the CD8 depletion experiments, this suggests that NK cells are not essential but CD8+ T cell responses are required in 6-thio-dG mediated anti-tumor effects.

Figure 2C:
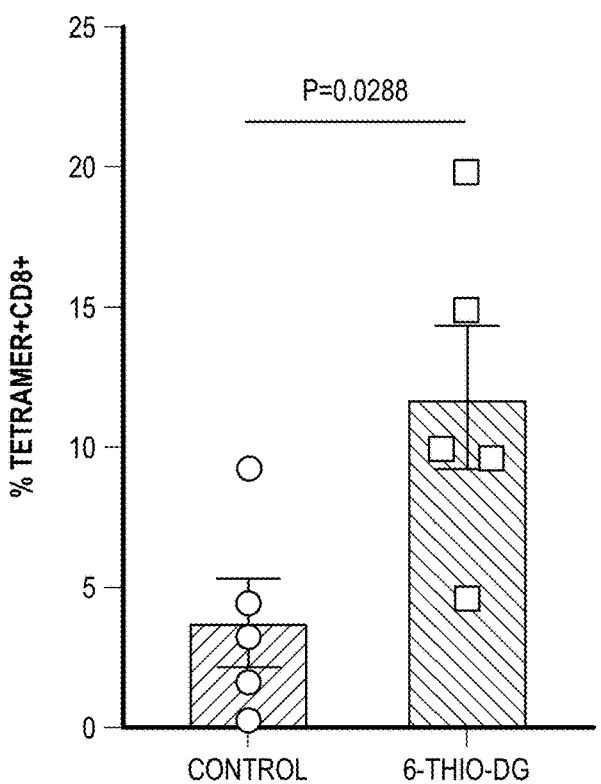
Figure 2D:
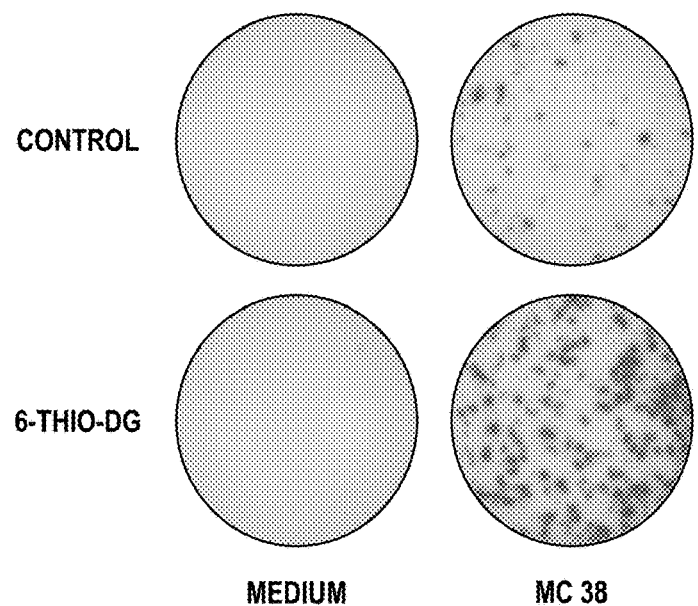
Figure 2E:
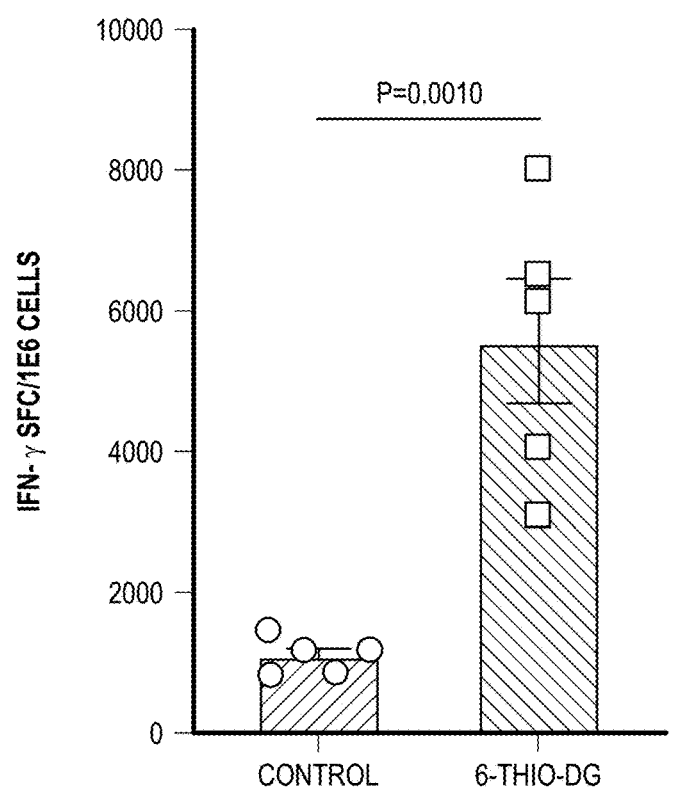
Figure 2F:
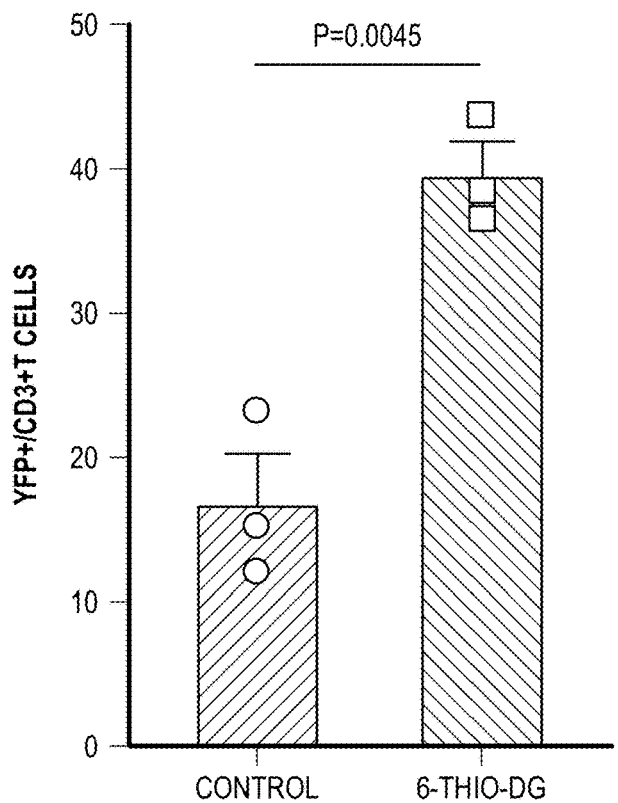
Figure 10F:
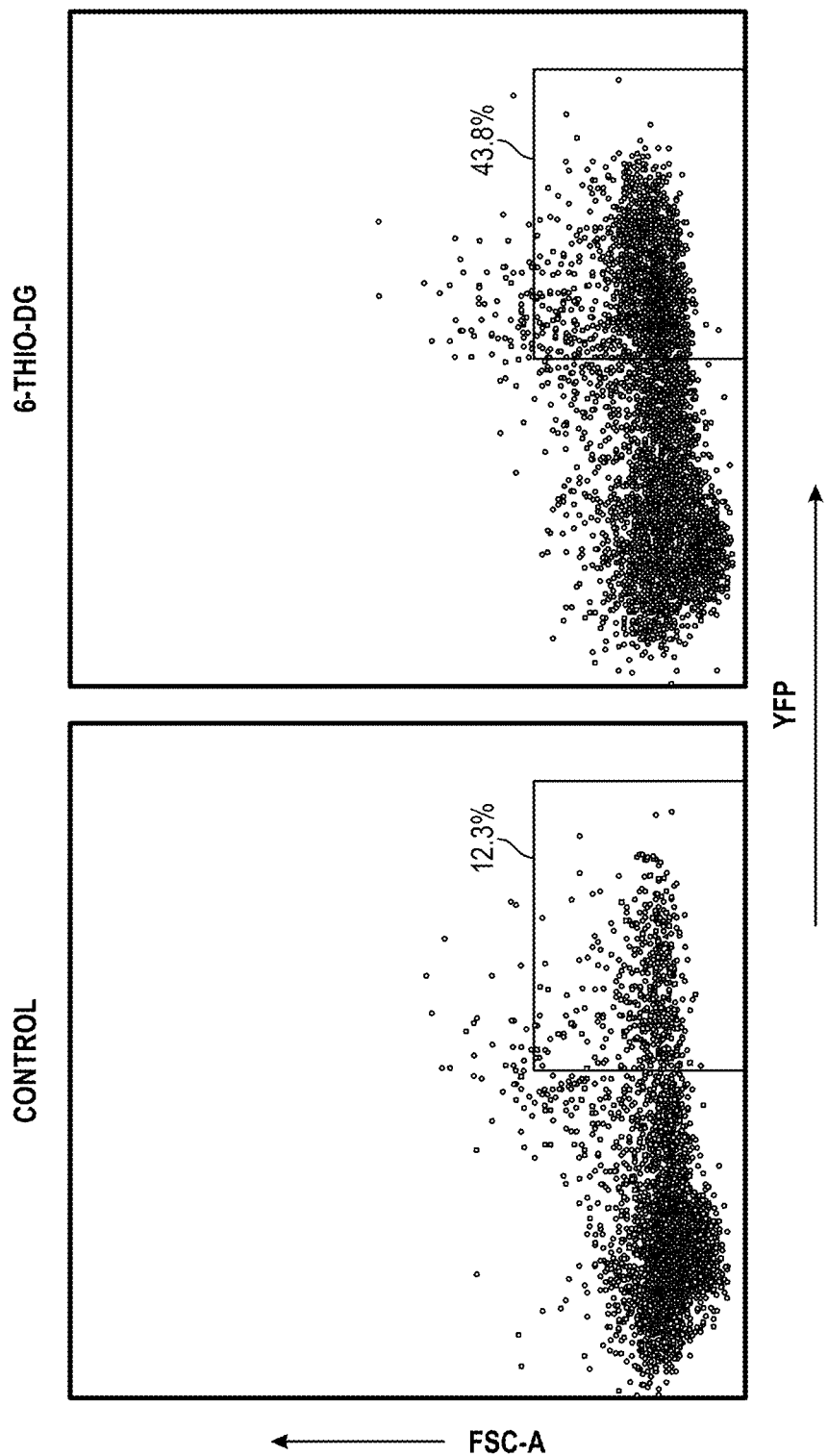

The inventors further tested the antigen-specific T cell response after 6-thio-dG treatment by using the MC38-OVA tumor model, which allows tracking of antigen specific T cells in the tumor tissue. Indeed, they observed increased tumor-specific CD8+ T cells in tumors 6 days after 6-thio-dG treatment (FIG. 2C). They also observed enhanced tumor-specific cytotoxic T cell responses in the MC38 tumor model by measuring IFN-γ producing T cells after 6-thio-dG treatment (FIGS. 2D and 2E). To directly assess the capacity of T cells to produce IFN-γ in vivo, the inventors utilized IFN-γ YFP reporter mice that allow tracking of IFN-γ producing T cells with YFP expression (Reinhardt et al., 2009). 6-thio-dG treatment significantly increased YFP+ T cells in the tumor, suggesting enhanced IFN-γ production ability of T cells (FIGS. 2F and 10F). The hallmark of an adaptive immune response is the formation of memory that initiates a rapid recall response when the same antigen appears. To determine if 6-thio-dG treatment induces a memory response, mice with completely regressed tumors after 6-thio-dG treatment were rested for 5 weeks and re-challenged with the same MC38 tumor but with 10 times more tumor cells on the opposite flank (left flank), and LLC tumor cells were inoculated as control on the right flank. When naïve mice (never exposed to MC38 cells or 6-thio-dG) were injected with the same number of MC38 cells, the tumors grew aggressively. Remarkably, all cured mice by 6-thio-dG treatment spontaneously rejected re-challenged MC38 tumors.

Figure 3A:
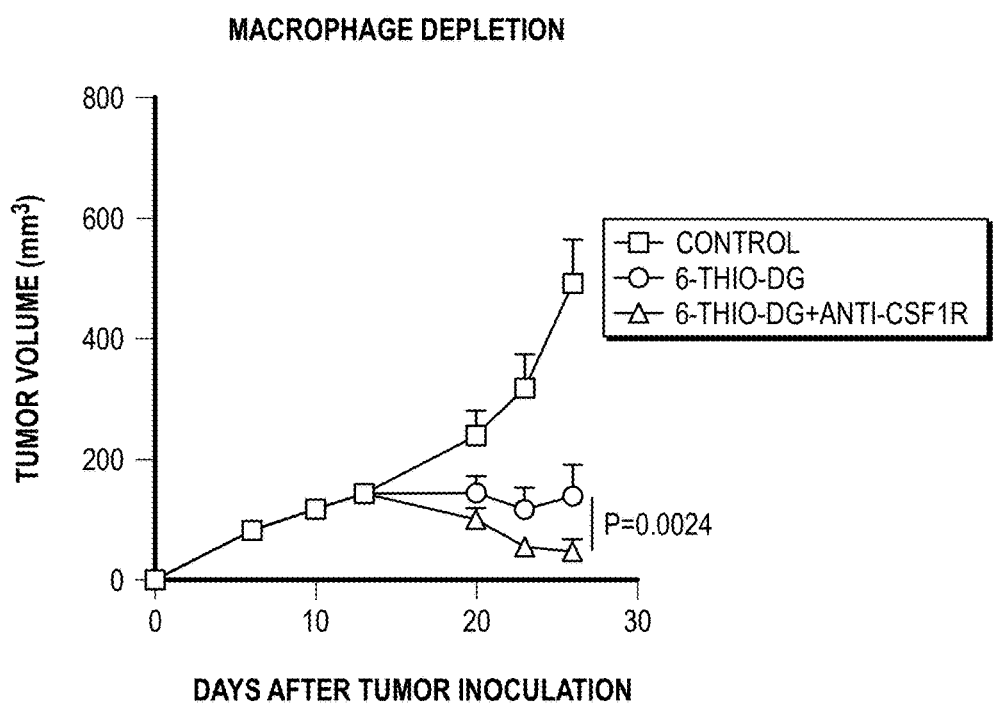
FIGS. 3A-F. 6-thio-dG treatment enhances the cross-priming capacity of dendritic cells.
Figure 3B:
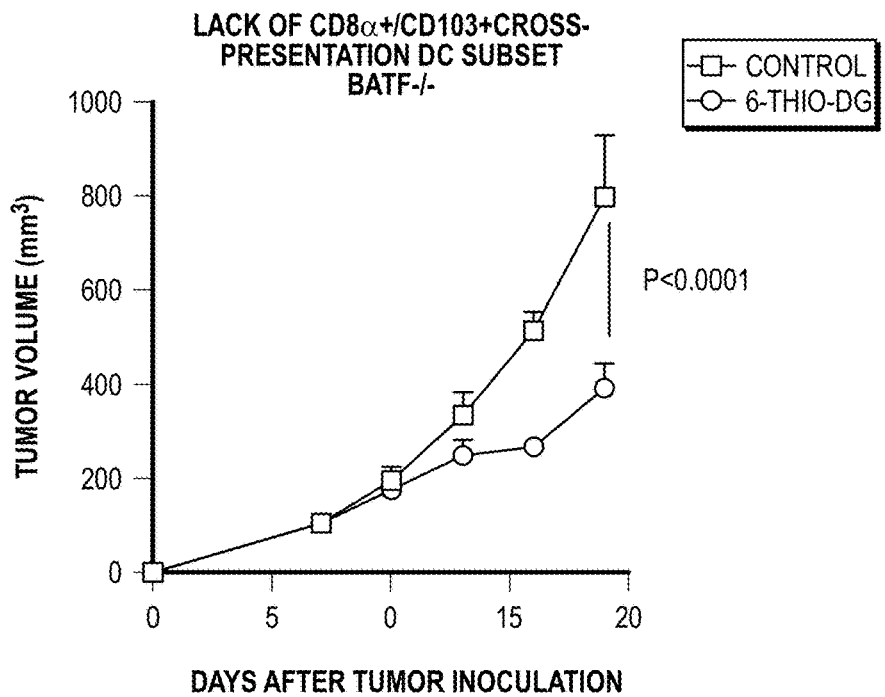
Figure 3C:
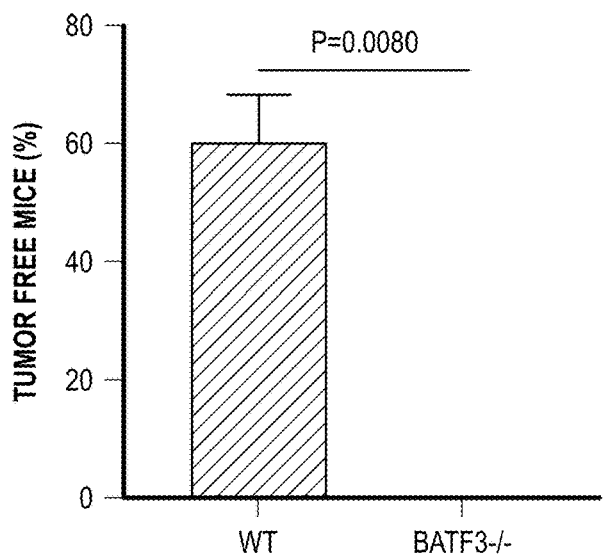

6-thio-dG treatment enhances the cross-priming capacity of dendritic cells. Antigen cross-presentation by antigen presenting cells (APCs) such as DCs or macrophages accounts for the tumor-specific CD8+ T cell activation. To explore which APC subset contributes to 6-thio-dG induced T cell activation, the inventors first used anti-CSF1R antibody to deplete macrophages. They found that 6-thio-dG worked even better in macrophage depleted group (FIG. 3A), which can be explained by the additive effect of the removal of immune suppressive tumor associated macrophages. BATF3 (basic leucine zipper ATF-like transcription factor 3)-dependent DCs are critical for the priming of antigen-specific CD8+ T cells (Broz et al., 2014; Edelson et al., 2010). 6-thio-dG treatment in Batf3 deficient mice partially delayed tumor growth but was significantly less effective compared with WT mice (FIG. 3B). Noticeably, 60% of WT mice were completely tumor free but none of mice were tumor free in Batf3−/− mice (FIG. 3C), suggesting an important role of BATF3-dependent DCs in the therapeutic effect of 6-thio-dG.

Figure 3D:
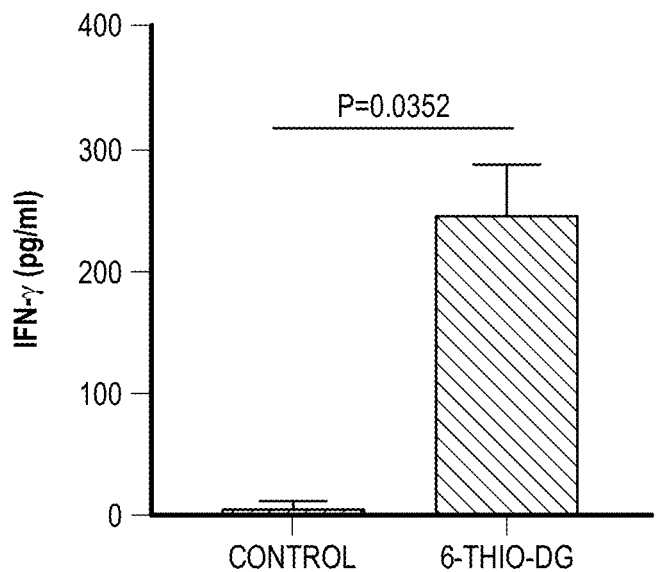
Figure 3E:
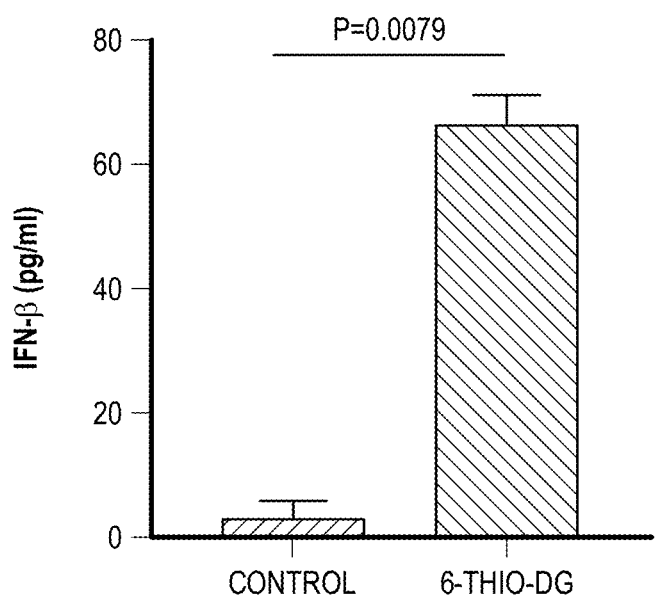
Figure 3F:
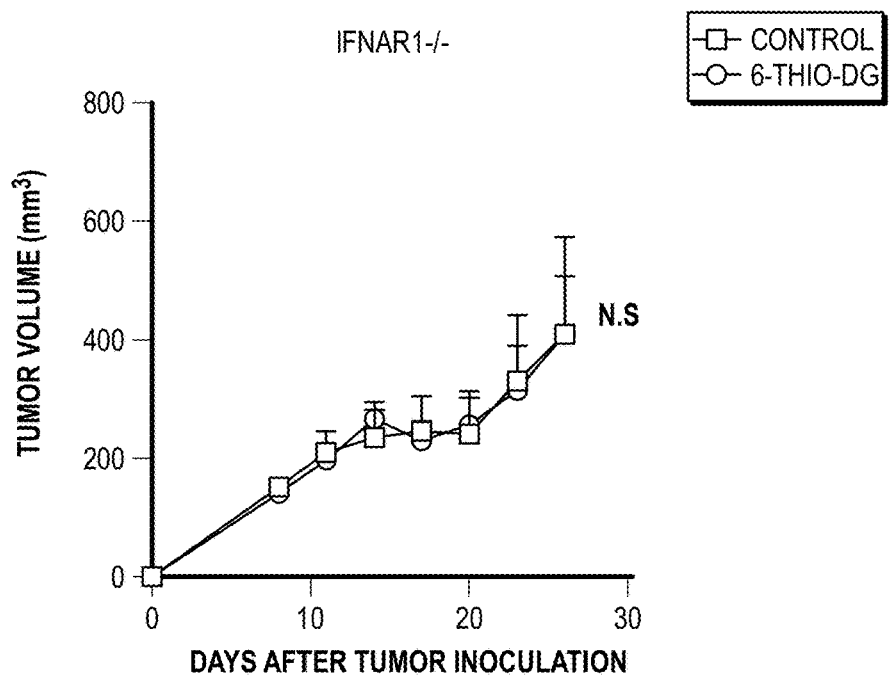

To directly demonstrate that 6-thio-dG treatment enhances cross-priming capacity of DCs, the inventors co-cultured 6-thio-dG pretreated MC38-OVA tumor cells with bone marrow derived DCs (BMDCs) overnight. Then the DCs were purified and co-cultured with naïve OT-1 transgenic CD8+ T cells that express the TCR with the specificity to recognize the $OVA_{257-264}$ epitope. They observed a significant increase of IFN-γ production by CD8+ T cells in the 6-thio-dG treatment group (FIG. 3D), which indicates an increased cross-priming capacity of DCs after 6-thio-dG treatment. Because IFN-I signaling promotes the cross-priming capacity of DCs (Diamond et al., 2011; Le Bon et al., 2003; Sanchez-Paulete et al., 2017), the inventors tested the production of IFN-β by DCs after co-culturing them with 6-thio-dG treated tumor cells. Indeed, IFN-β production significantly increased in the 6-thio-dG treatment group, indicating increased innate sensing of DCs (FIG. 3E). They further investigated whether the IFN-I pathway is essential for 6-thio-dG-mediated anti-tumor effect. Using Ifnar1−/− mice, the inventors showed that the loss of IFN-I signaling in the host abolished the anti-tumor effect of 6-thio-dG (FIG. 3F), indicating the indispensable role of IFN-I signaling in 6-thio-dG treatment.

Figure 4A:
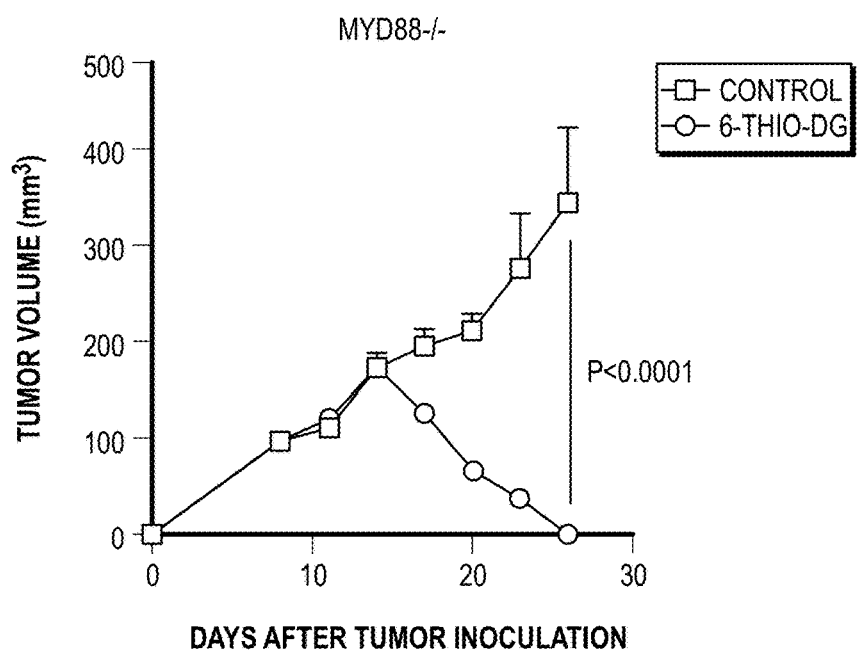
FIGS. 4A-G. STING signaling in host is required for 6-thio-dG induced innate sensing.
Figure 4B:
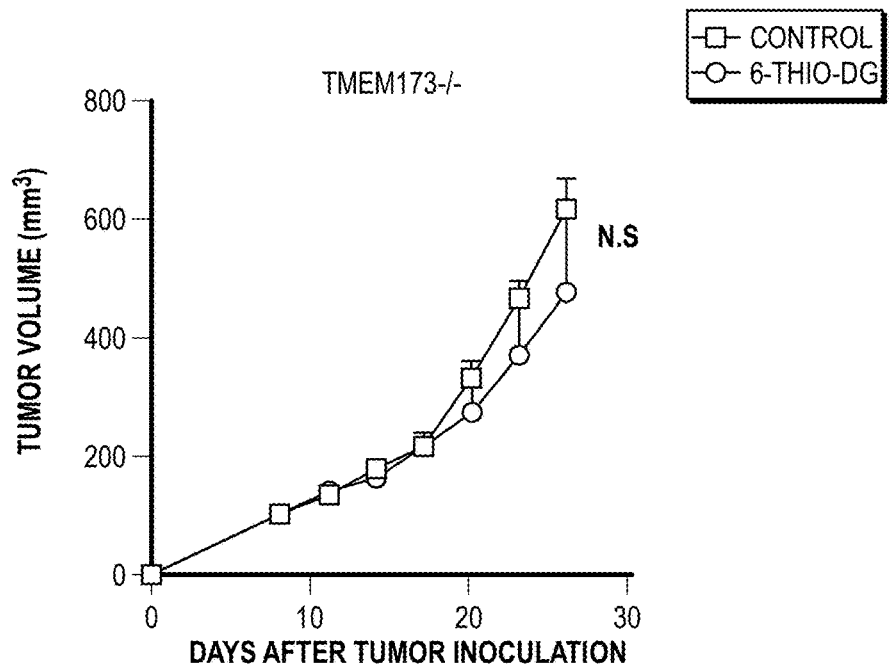
Figure 4C:
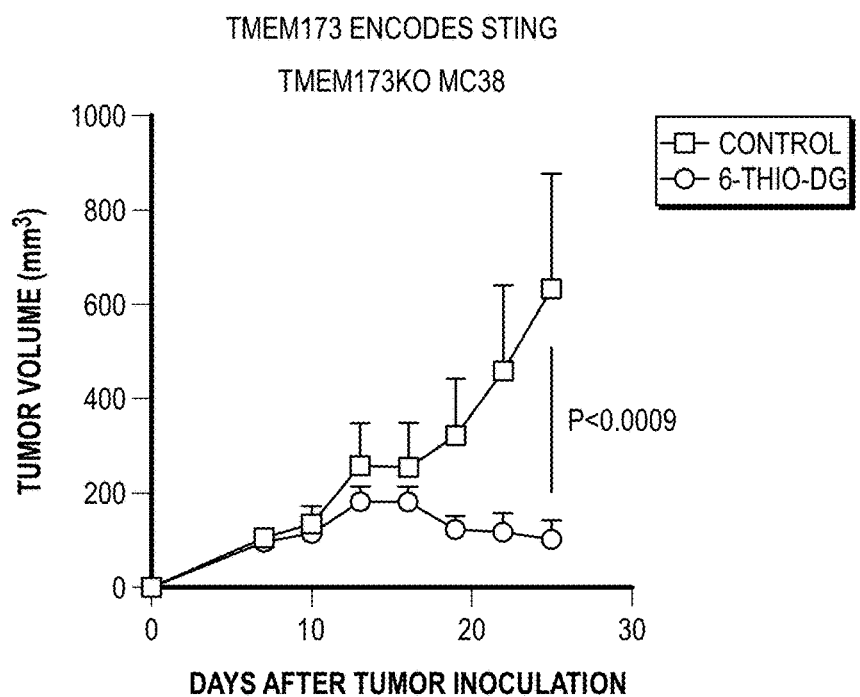
Figure 4D:
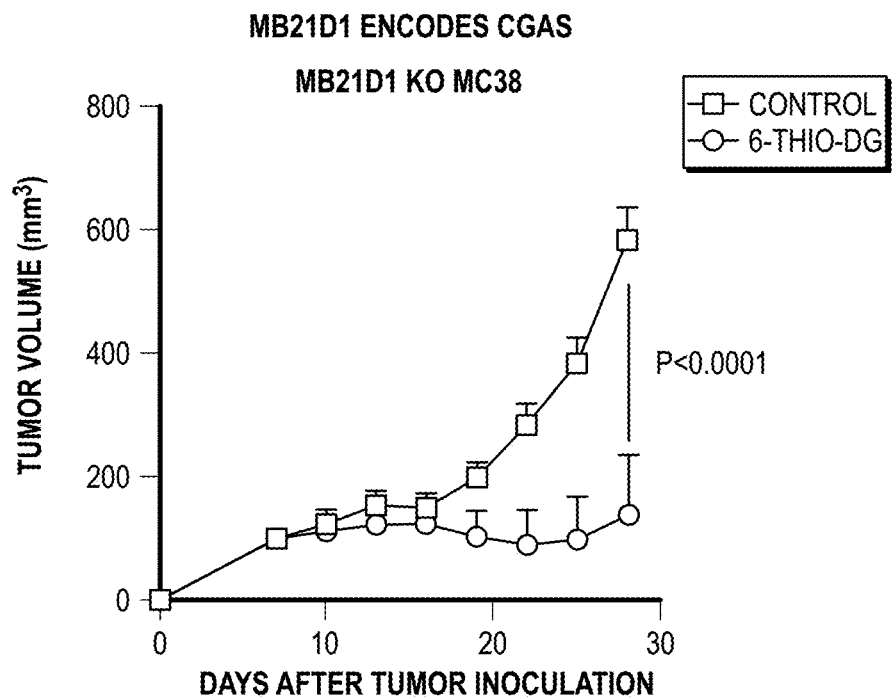
Figure 11A:
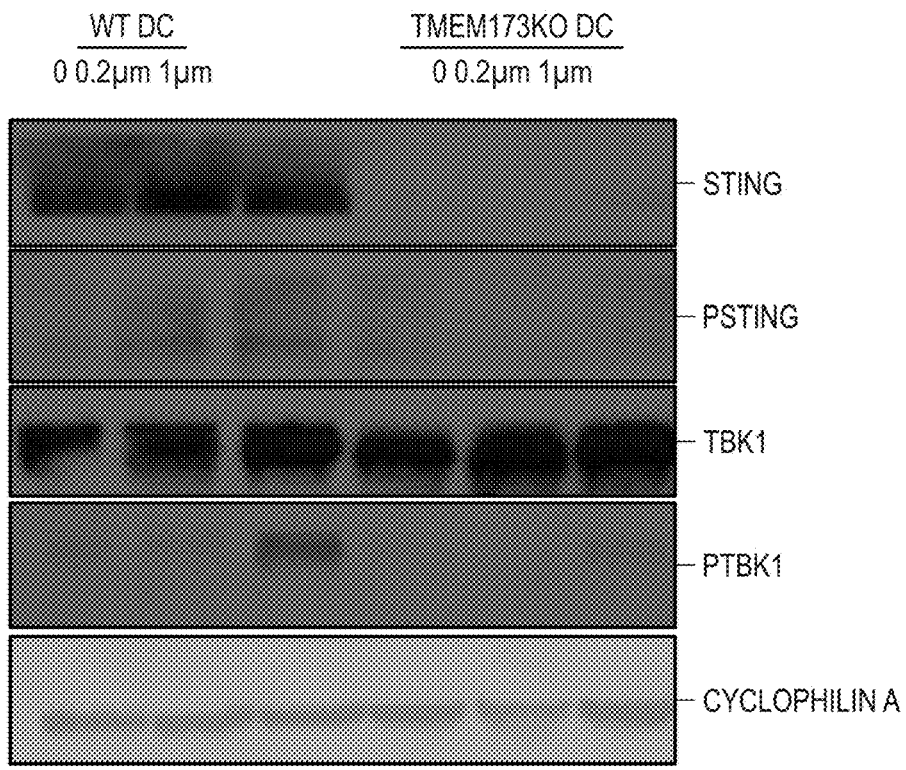
FIGS. 11A-H (related to FIGS. 4A-G).
Figure 11B:
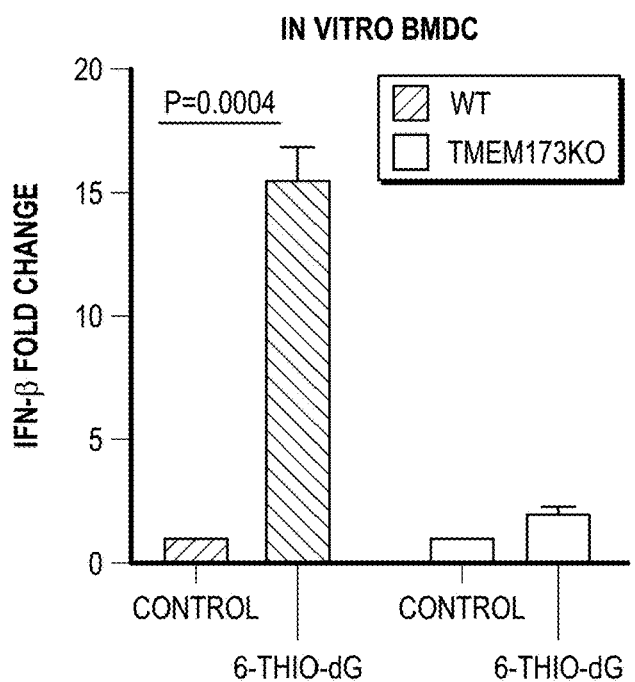

STING signaling in the host is required for 6-thio-dG induced innate sensing. Tumor cells under stress might release danger-associated molecular patterns (DAMPs) to engage TLR/Myd88 pathways in APCs and initiate IFN-I signaling. Tumor-derived DNAs can also trigger the cytosolic DNA sensing cGAS/STING pathway and activate IFN-I pathways (Deng et al., 2014; Li et al., 2019). To further delineate which upstream pathway is essential in 6-thio-dG triggered IFN-I signaling activation in host cells, the inventors inoculated MC38 tumors into Myd88−/− and Tmem173−/− (Tmem173 encodes STING) mice. 6-thio-dG treatment-controlled tumor growth well in Myd88−/− mice but completely lost efficacy in Tmem173−/− mice (FIGS. 4A and 4B), suggesting an essential role of host STING signaling in 6-thio-dG triggered innate sensing. They further investigated whether 6-thio-dG treatment activates the host STING/IFN-I pathway. They observed an increase of TBK1 phosphorylation in DCs after co-culture with 6-thio-dG pre-treated tumor cells and the phosphorylation was completely diminished in Tmem173 DCs (FIG. 11A). 6-thio-dG treatment induced IFN-β production in DCs in a STING-dependent manner (FIG. 11B). As previous studies reported that tumor-intrinsic STING signaling is critical in innate-sensing inducing cancer therapies (Sen et al., 2019; Vanpouille-Box et al., 2017), the inventors tested whether tumor-intrinsic STING signaling also contributes to 6-thio-dG treatment efficacy. They used CRISPR/Cas9 to knock out Tmem173 and Mb21d1 (Mb21d1 encodes cGAS) in MC38 tumor cells. In contrast to other studies, tumor-intrinsic STING signaling played a non-essential role, as 6-thio-dG treatment still controlled tumor growth in mice bearing Tmem173KO and Mb21d1KO tumor cells (FIGS. 4C and 4D).

Figure 4E:
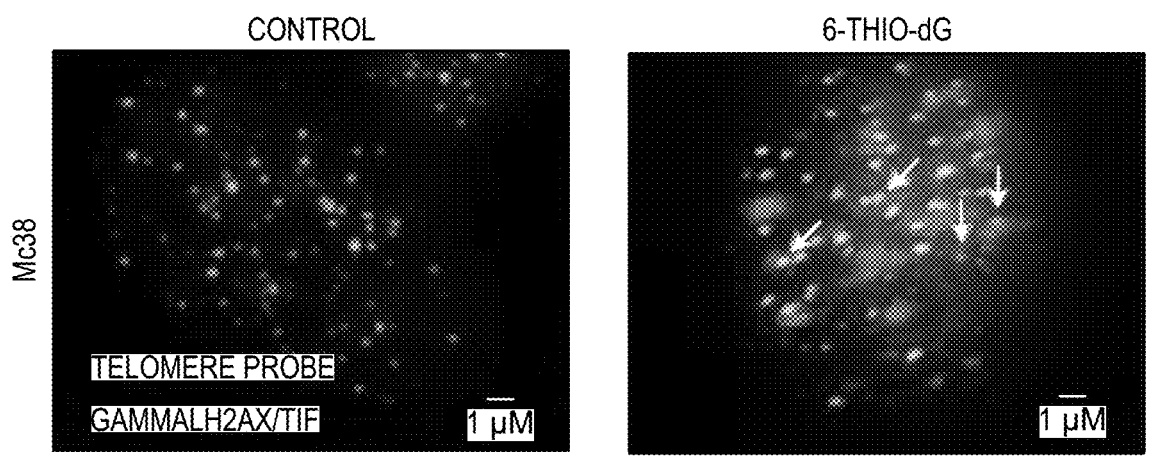
Figure 4F:
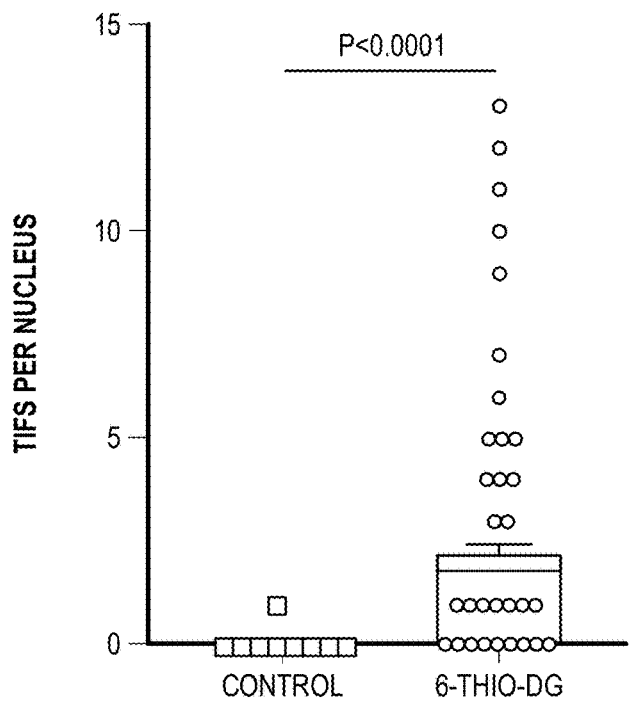
Figure 11C:
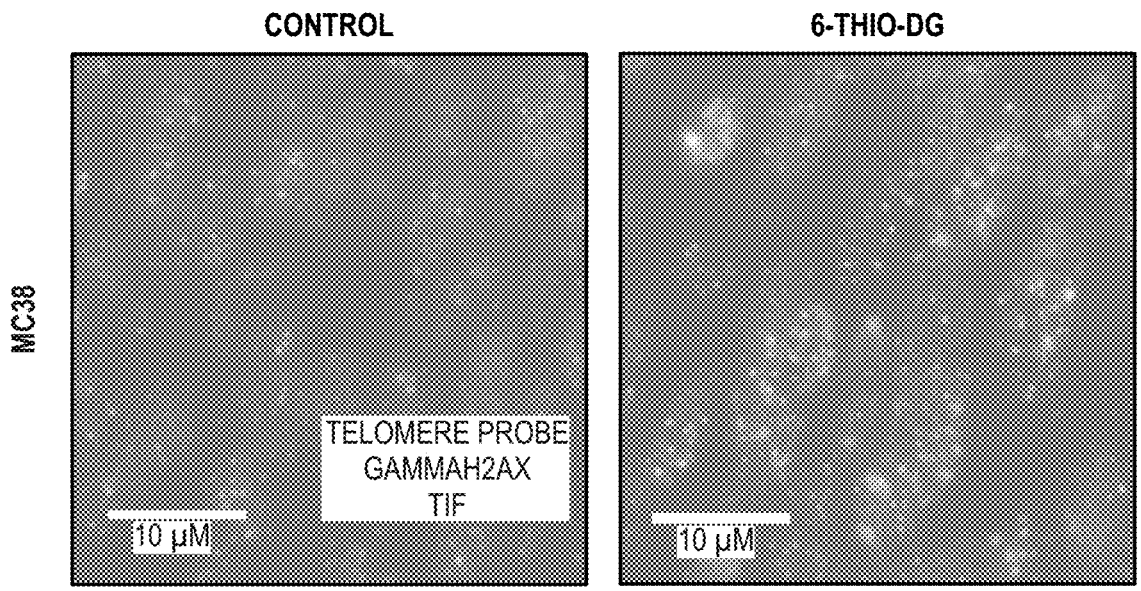
Figure 11D:
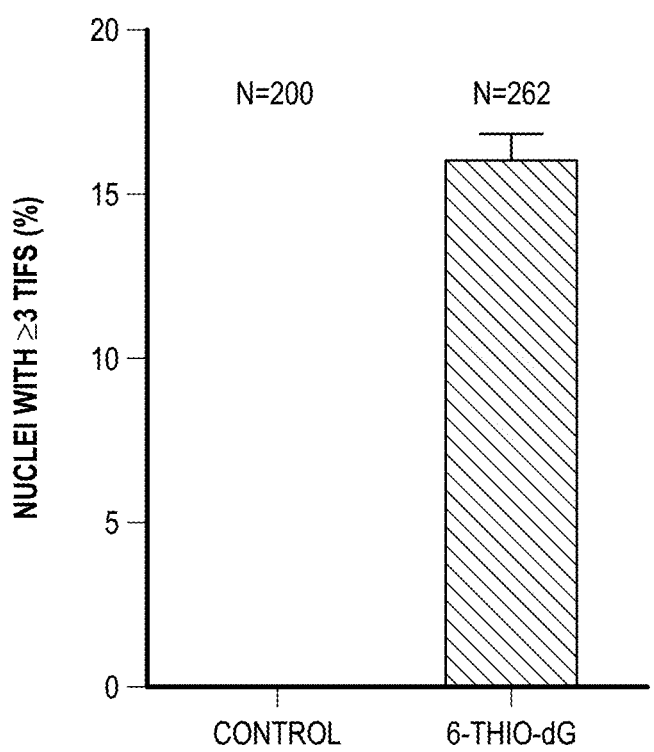
Figure 11E:
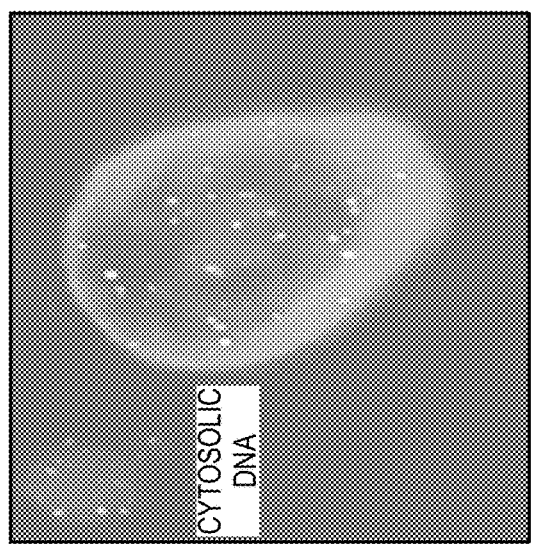
Figure 11E:
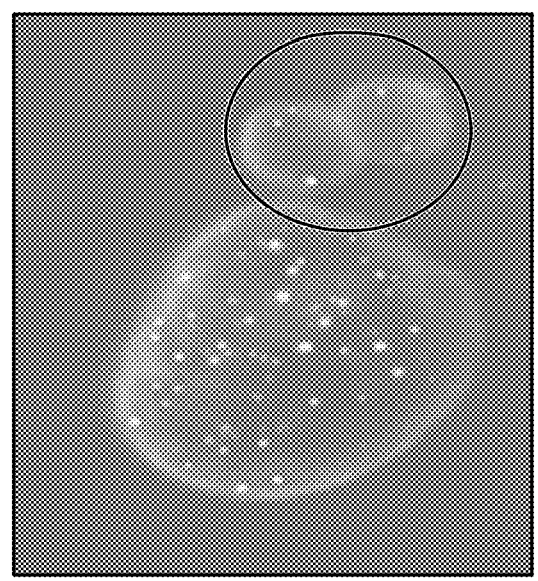
Figure 11E:
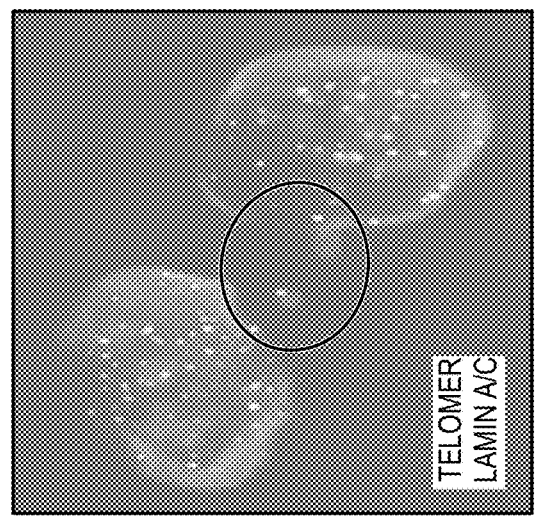
Figure 11F:
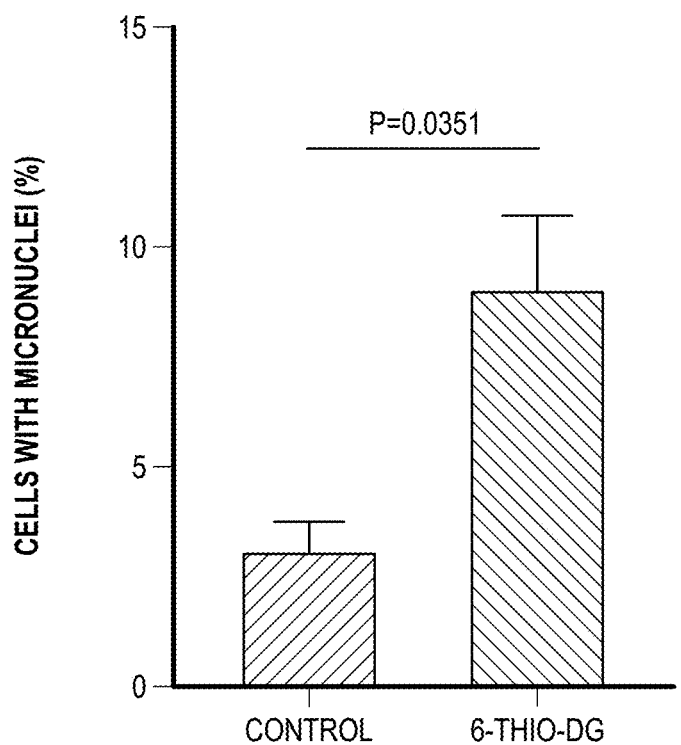

The inventors then sought to determine how 6-thio-dG treated tumor cells trigger innate sensing in DCs. Since 6-thio-dG is a telomere-targeting drug, 6-thio-dG induced telomere stress might contribute to innate sensing of DCs by releasing DNAs. Therefore, the inventors first analyzed telomere stress by the TIF (Telomere dysfunction Induced Foci) assay and showed that 6-thio-dG induced telomere damages in MC38 cells (FIGS. 4E and 4F). Since telomeres are only a small fraction of genomic DNA (~1/6000) any co-localization of telomeres with DNA damage is significant. They also observed similar increases of TIFs in 6-thio-dG treated tumor tissues from MC38-tumor bearing mice (FIGS. 11C and 11D). 6-thio-dG also induced interphase bridges between the two daughter cells during telophase and since many contained telomere sequences, this may explain why many micronuclei containing telomere signals when cells re-entered interphase after mitosis (FIG. 11E). These cytosolic fragments formed micronuclei with fragile nuclear envelopes (FIGS. 1E and 11F), which can be eventually recognized as a danger signal. These DNA fragments are released from the cells and can be taken up by DCs.

Figure 4G:
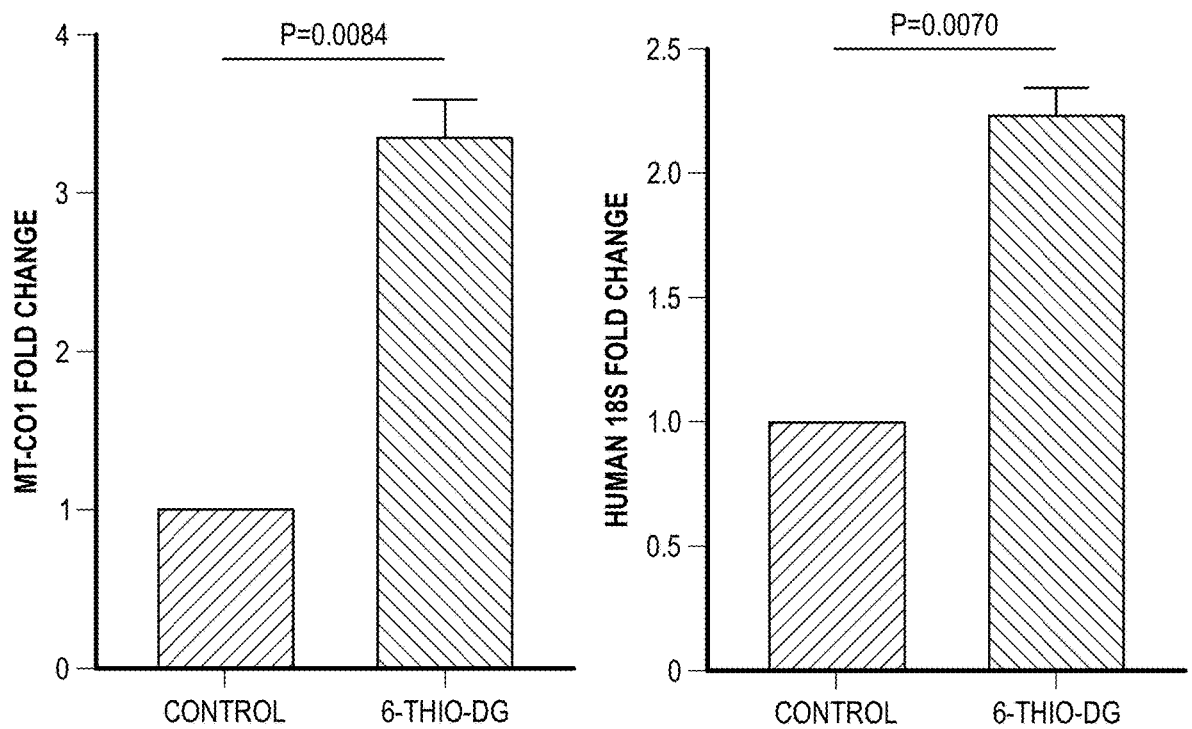
Figure 11G:
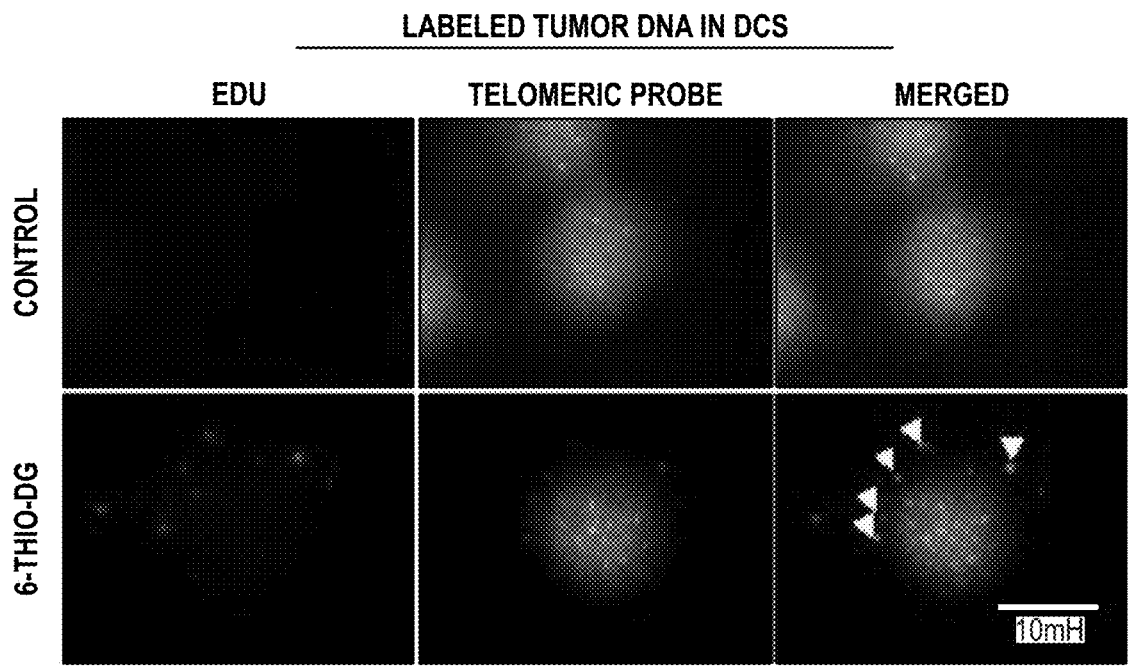
Figure 11H:
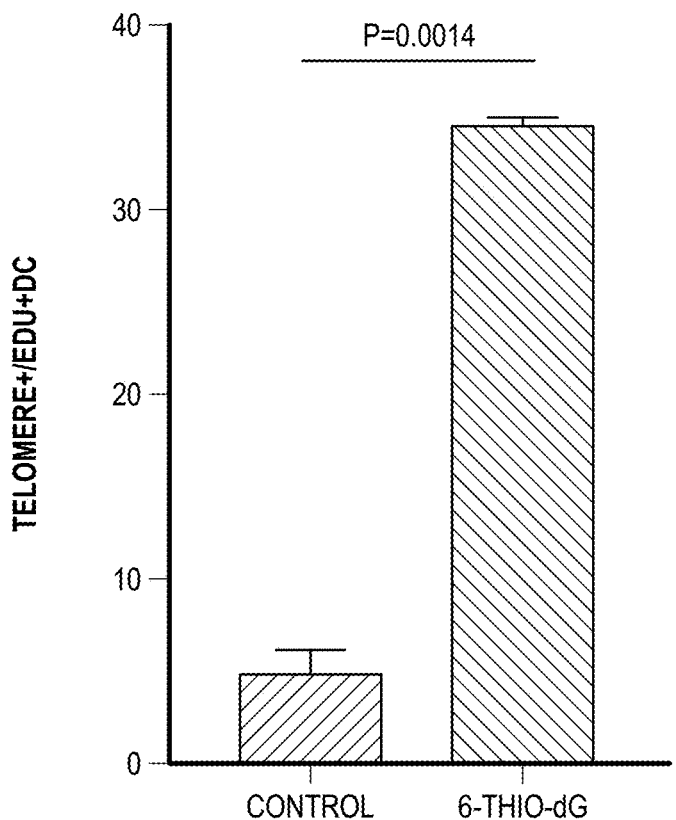

To substantiate this hypothesis, the inventors treated HCT116, a human colon cancer cell line, with 6-thio-dG and co-cultured them with mouse BMDC for 4 hrs, and then they isolated DCs and extracted cytosolic DNA. The short-time co-culture of a human tumor cell line with mouse BMDCs allowed us to distinguish DNAs from different origins. They found an increase of human DNAs (MT-CO1 and human 18S) in the cytosol of mouse DCs after 6-thio-dG treatment, which suggests that DNAs from the tumors enter the host DCs (FIG. 4G). To determine if 6-thio-dG treatment increases the uptake of unique telomeric DNAs by DCs, the inventors labeled tumor cells with EdU, then washed the cells. Next, they treated with 6-thio-dG, then washed cells again. Finally, they co-cultured tumor cells with DCs and then isolated the DC for analysis. Among DCs had the uptake of tumor DNAs (EdU$^+$DC) in the cytosol, the inventors observed an increase of telomere co-localization with EdU after 6-thio-dG treatment, suggesting a significant uptake of tumor derived telomeric DNAs (FIGS. 11G and 11H). Together, the inventors demonstrated that 6-thio-dG triggers innate sensing through the activation of the host cytosolic DNA sensing STING/IFN-I pathway.

Figure 5A:
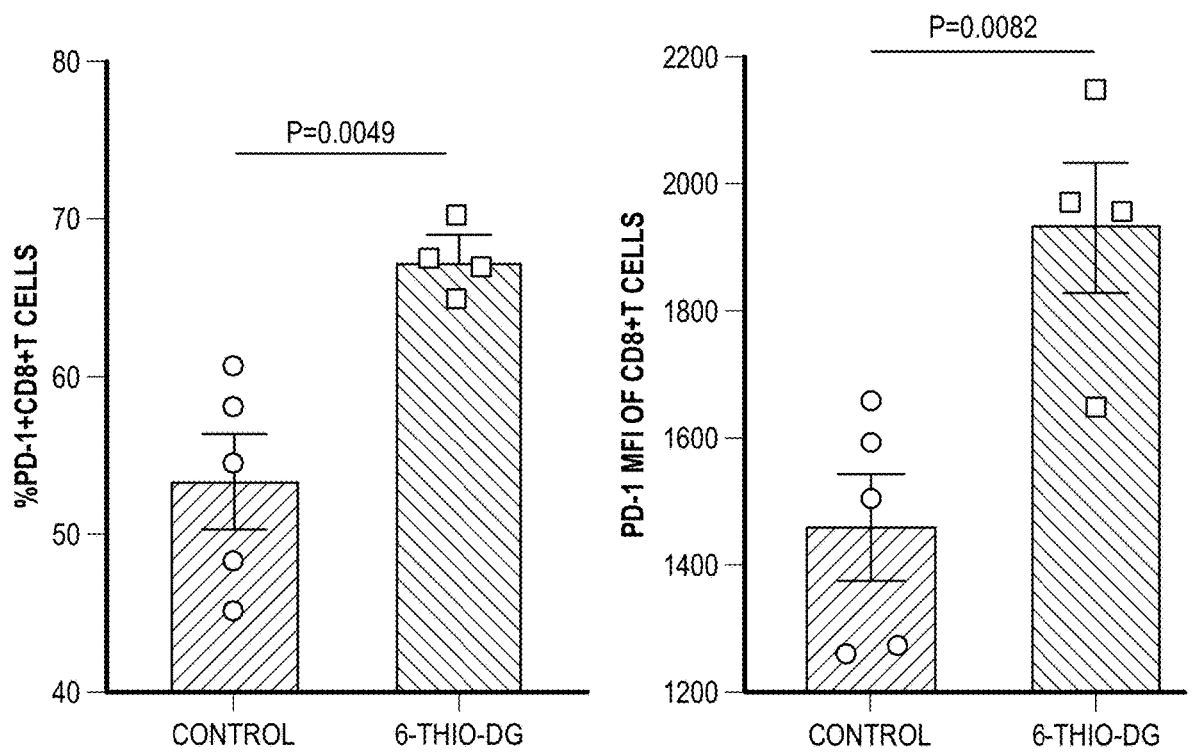
FIGS. 5A-F. 6-thio-dG overcomes PD-L1 blockade resistance in advanced tumor models.
Figure 5B:
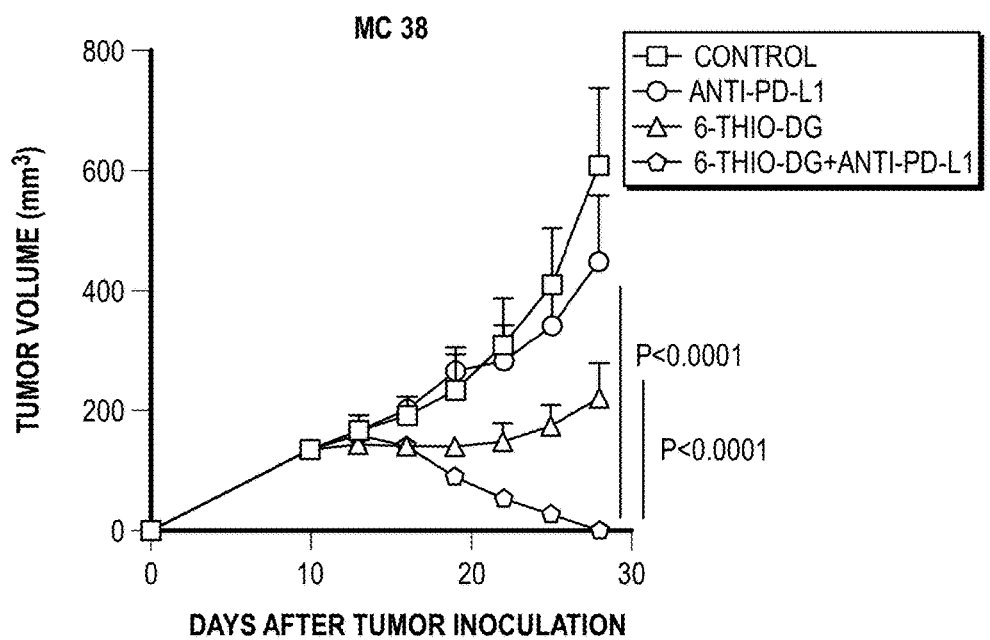
Figure 5C:
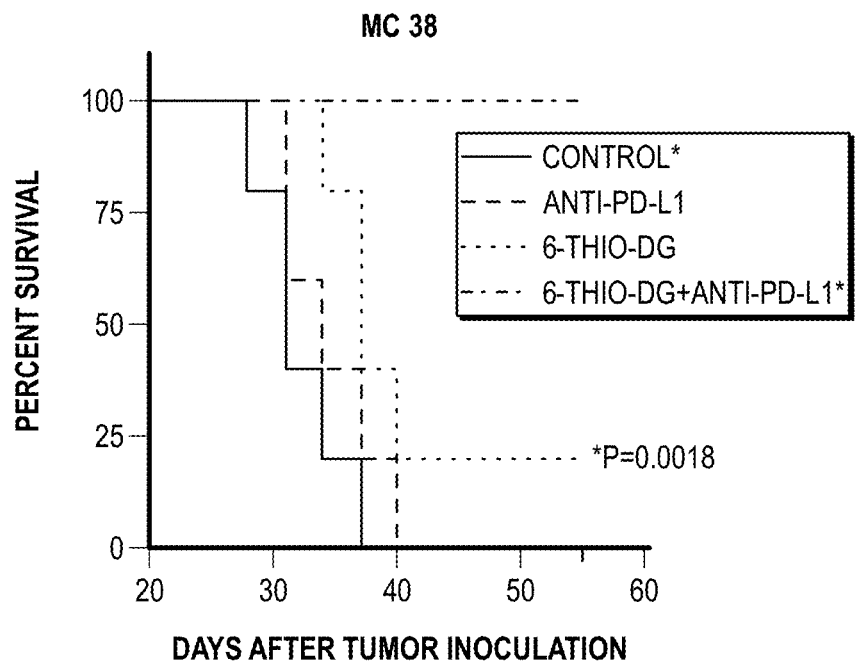
Figure 5D:
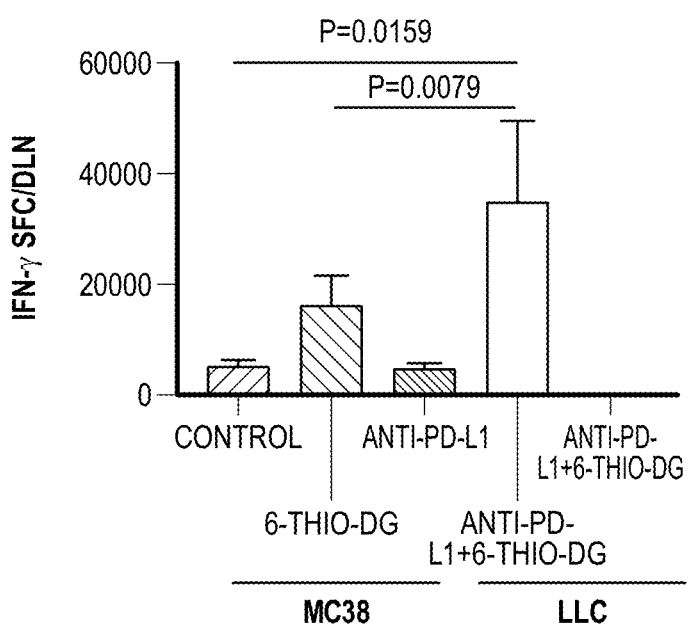
Figure 12:
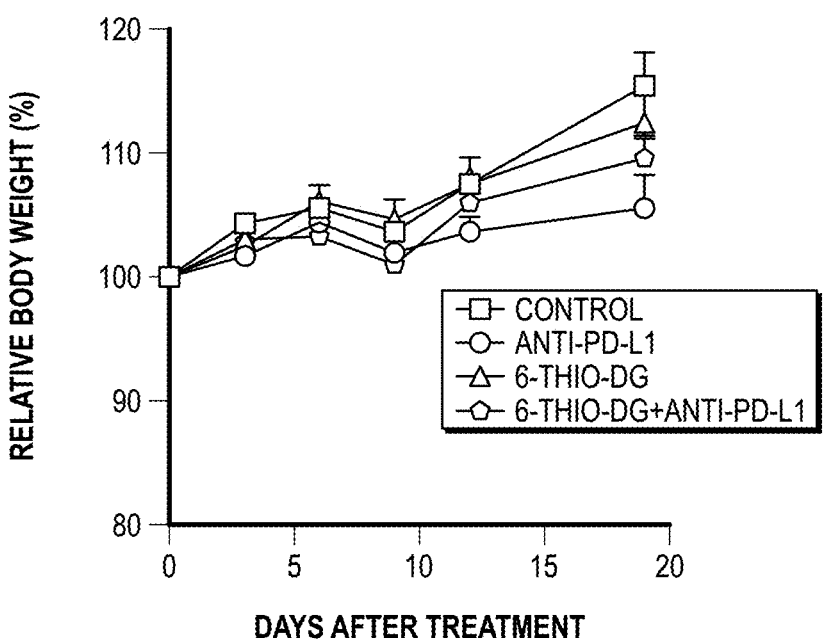
FIG. 12 (related to FIGS. 5A-G). C57BL/6 mice (n=5) were inoculated with $5\times10^5$ MC38 tumor cells and treated with 6-thio-dG (3 mg/kg, days 10, 11). 50 µg anti-PD-L1 antibody was administrated on day 13 and day 17. Mice body weight were measured. Data were shown as mean±SEM.

6-thio-dG overcomes PD-L1 blockade resistance in advanced tumors. While 6-thio-dG treatment activated CD8+ T cells, it also upregulated PD-1 expression in the frequency of total CD8+ T cells and on per cell basis (FIG. 5A). PD-1 is a co-inhibitory molecule that limits T cell activation. The elevated PD-1 expression might eventually inhibit the cytotoxic CD8+ T cell function after 6-thio-dG treatment. Therefore, the inventors reasoned that combination of 6-thio-dG with PD-1/PD-L1 blockade might augment the overall anti-tumor immune response, especially in the advanced tumor setting which harbors a more immune suppressive microenvironment containing multiple resistance mechanisms that limit single treatment efficacy. Since 6-thio-dG single treatment was only effective in relatively small tumor sizes ~100 mm$^3$, for advanced tumor treatment the inventors let the tumor sizes reach to 150-200 mm$^3$ and then treated with 6-thio-dG and/or anti-PD-L1 treatment. In such advanced cancers, tumor volume is difficult to control with two daily treatments with 6-thio-dG or by two treatments with anti-PD-L1 (FIG. 5B). However, sequential administration of 6-thio-dG and anti-PD-L1 completely inhibited the tumor growth (FIG. 5B). Remarkably, only mice in the combination treatment group achieved a 100% survival rate (FIG. 5C), showing a synergistic effect of 6-thio-dG treatment with PD-L1 blockade. In addition, the inventors did not observe any body weight loss of mice in the combination treatment group (FIG. 12). They further analyzed the tumor-specific T cell response in draining lymph nodes (dLNs) and found that the anti-PD-L1 treatment had little effect on T cell activation in advanced tumors. In contrast, combination therapy significantly increased IFN-γ production compared to other groups. The immune response was MC38 tumor specific as there were almost no IFN-γ spots in the control LLC tumor stimulation group (FIG. 5D).

Figure 5E:
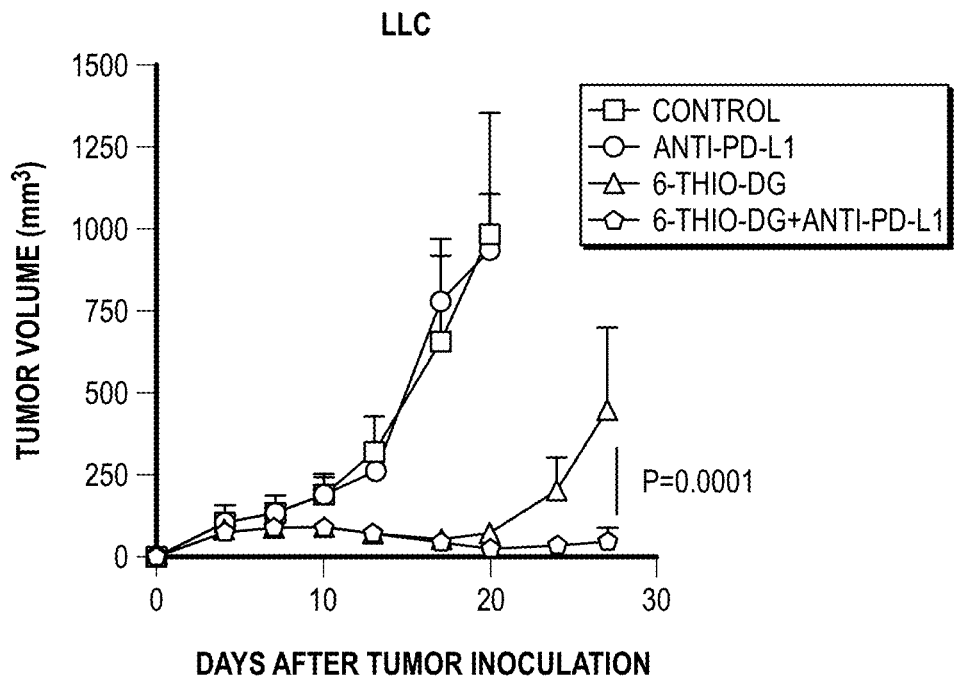
Figure 5F:
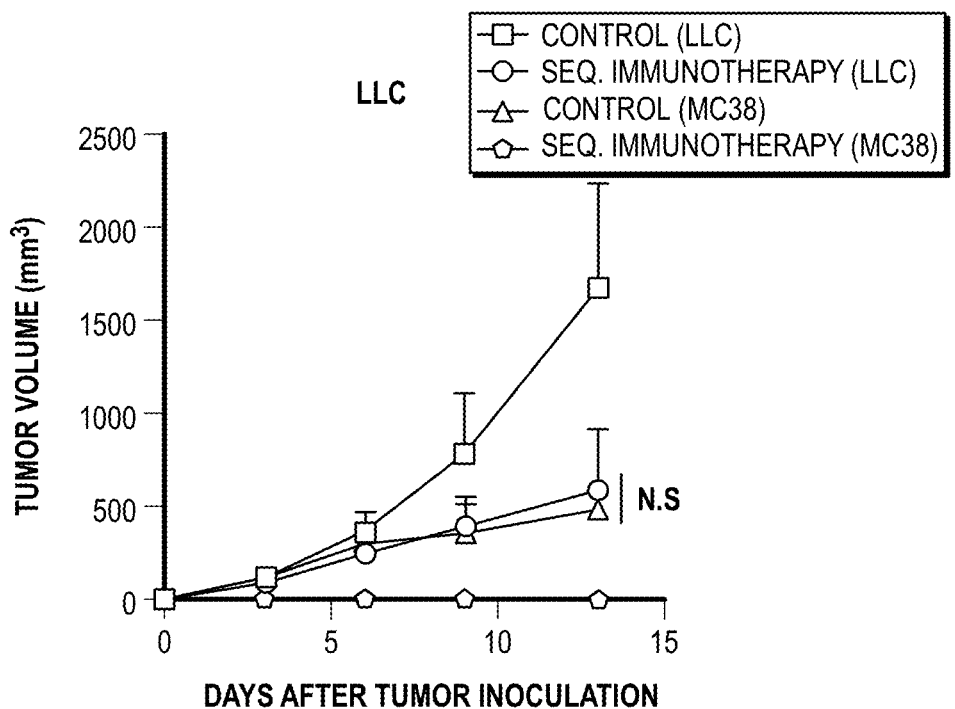

MC38 is known to be an immunogenic tumor model. To test if the combination therapy can also overcome PD-L1 blockade resistance in less immunogenic tumor models, the inventors employed the mouse LLC tumor model that has been reported to be resistant to PD-L1 blockade (Bullock et al., 2019; Li et al., 2017). Consistent with previous reports, single treatment with anti-PD-L1 had no therapeutic effect (FIG. 5E). Notably, combination of 6-thio-dG with anti-PD-L1 significantly reduced mouse tumor burden and 40% of mice eventually completely rejected tumors (FIG. 5E). The inventors re-challenged tumor-free mice 6 weeks after tumor regression to check the memory response. All combination treated mice spontaneously rejected LLC tumors but not MC38 tumors, suggesting a long-lasting tumor-specific immune memory (FIG. 5F). Based on these results, 6-thio-dG treatment overcomes PD-L1 blockade resistance in advanced tumors. This will potentially benefit PD-1/PD-L1 blockade resistant patients in the clinic.

Figure 6A:
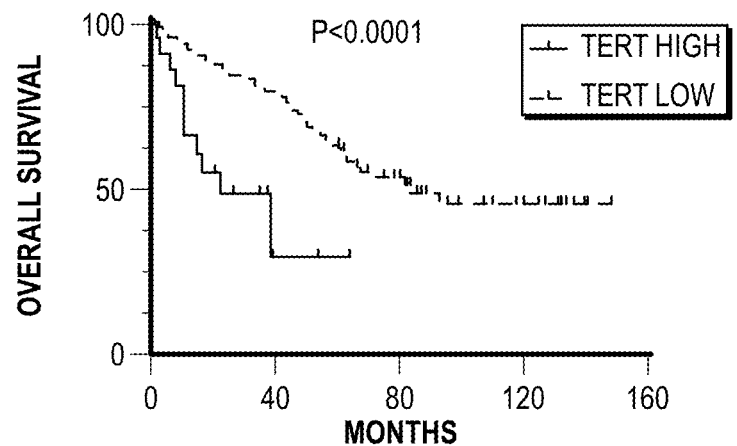
FIGS. 6A-E. 6-thio-dG reduces human colon cancer burden in a humanized mouse model.
Figure 6B:
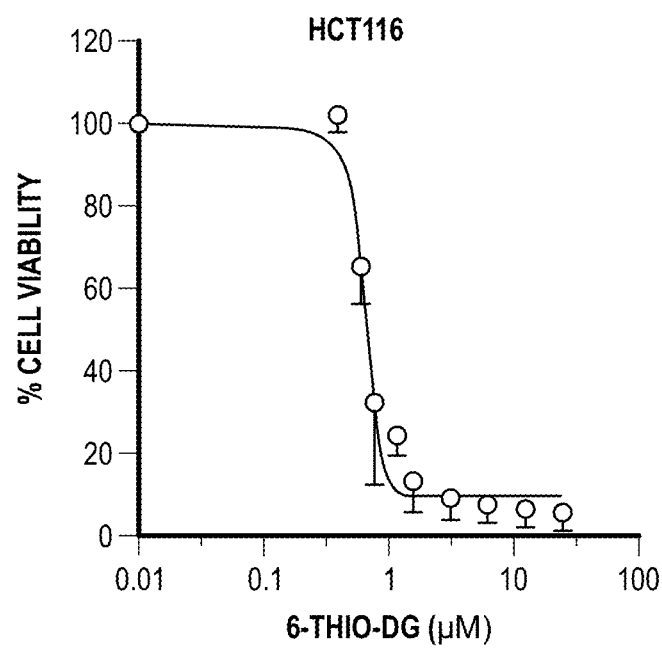
Figure 6C:
Figure 6D:
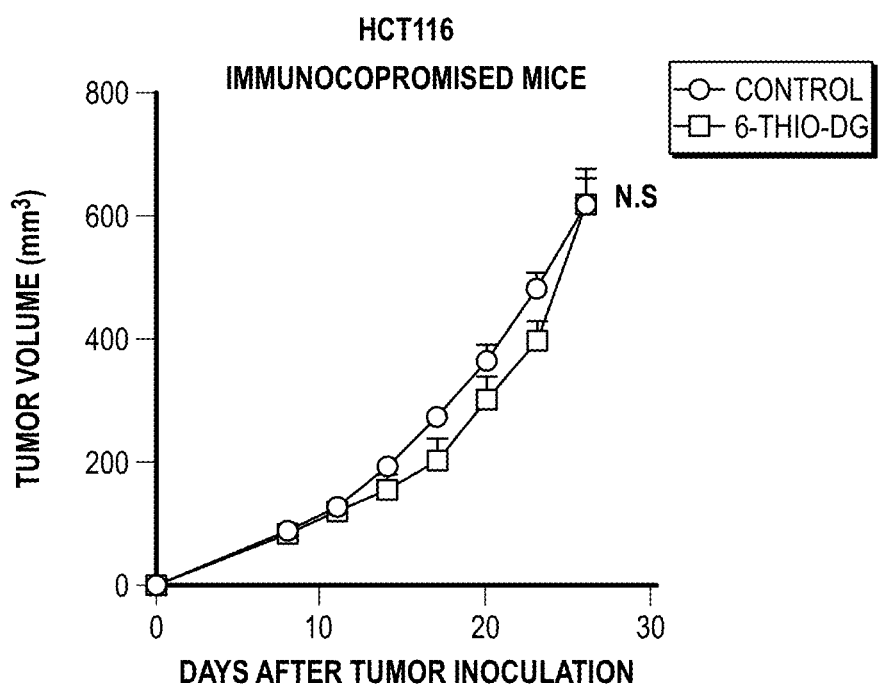
Figure 6E:
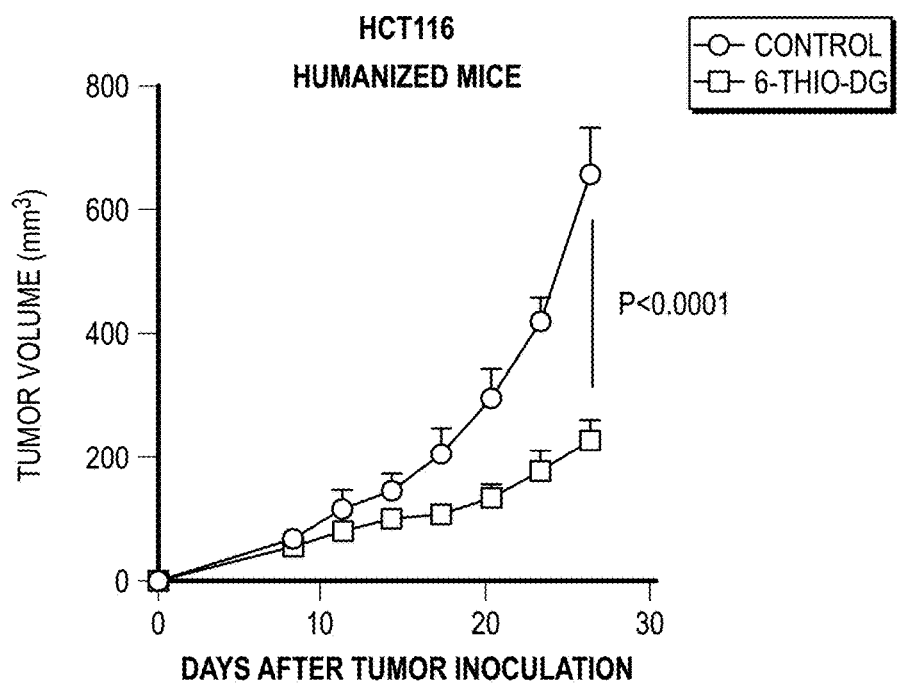
Figure 7:
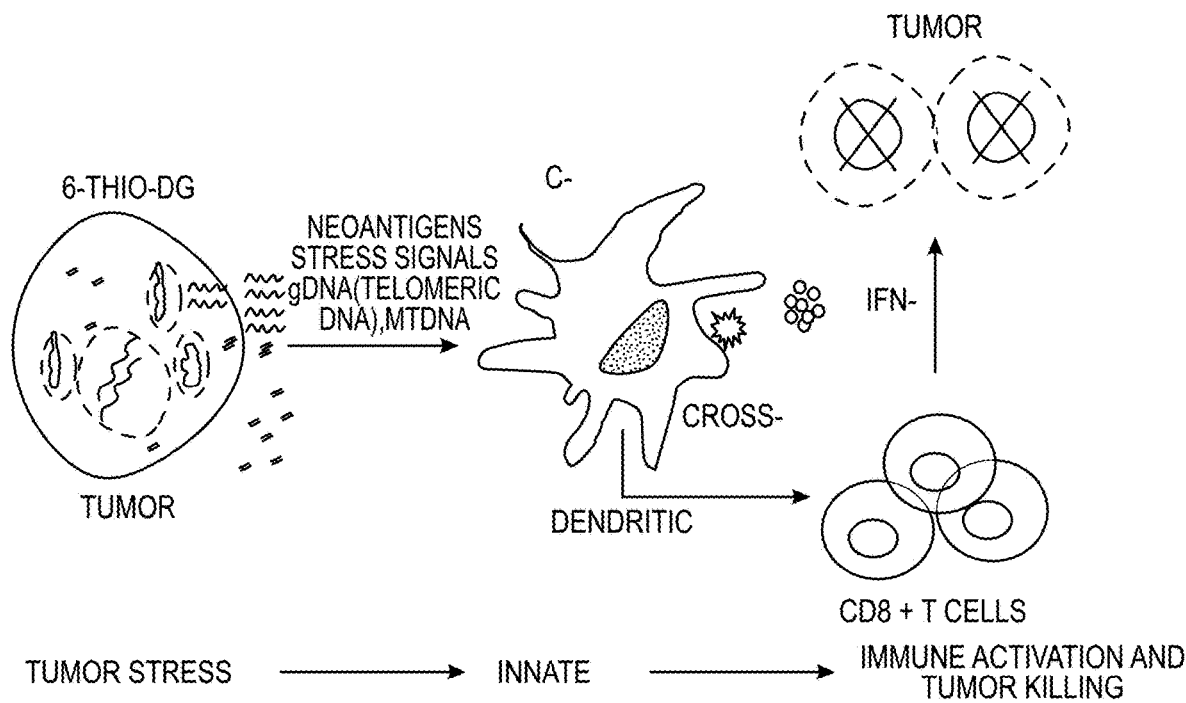
FIG. 7. Schematic of 6-thio-dG induction of c-GAS/STING/IFN.
Figure 13A:
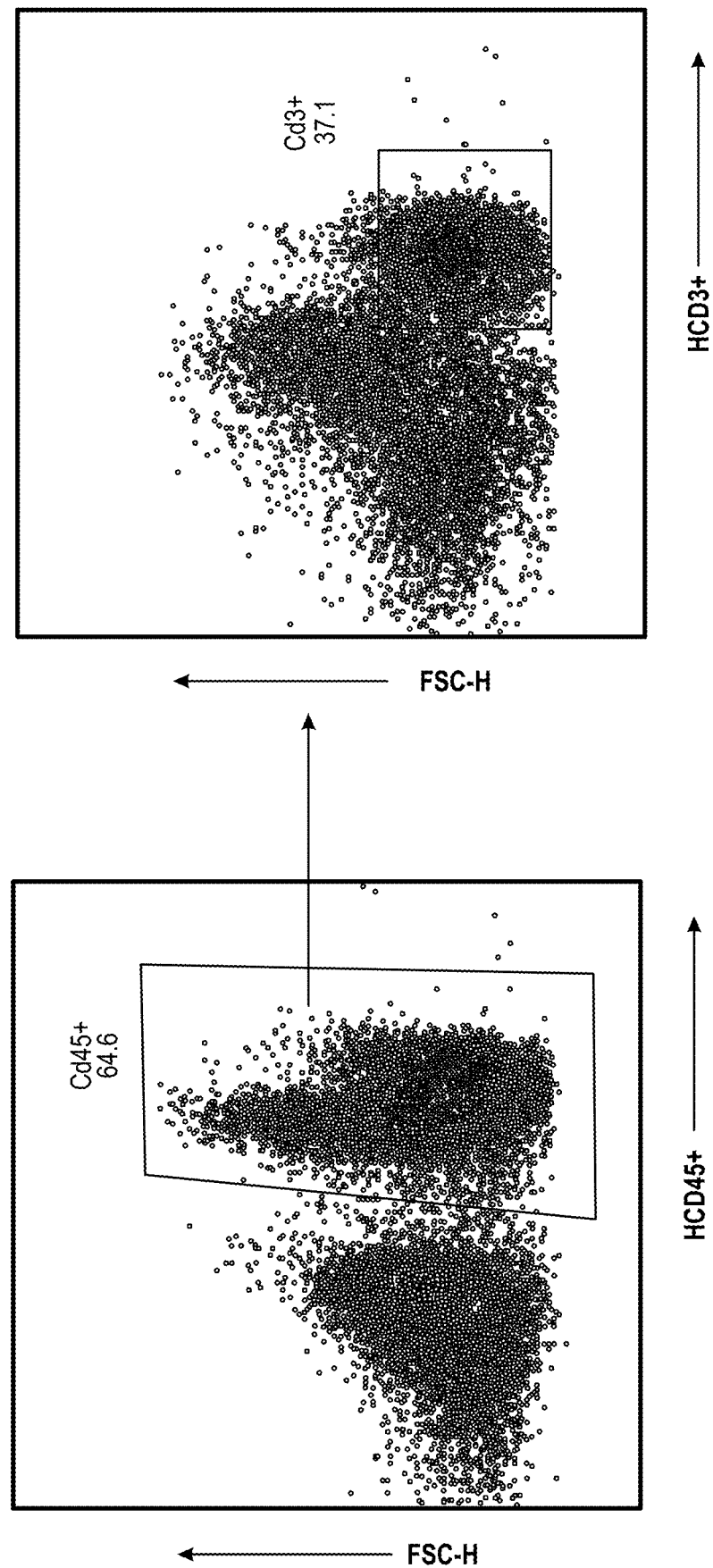
FIGS. 13A-F (related to FIGS. 6A-E).
Figure 13B:
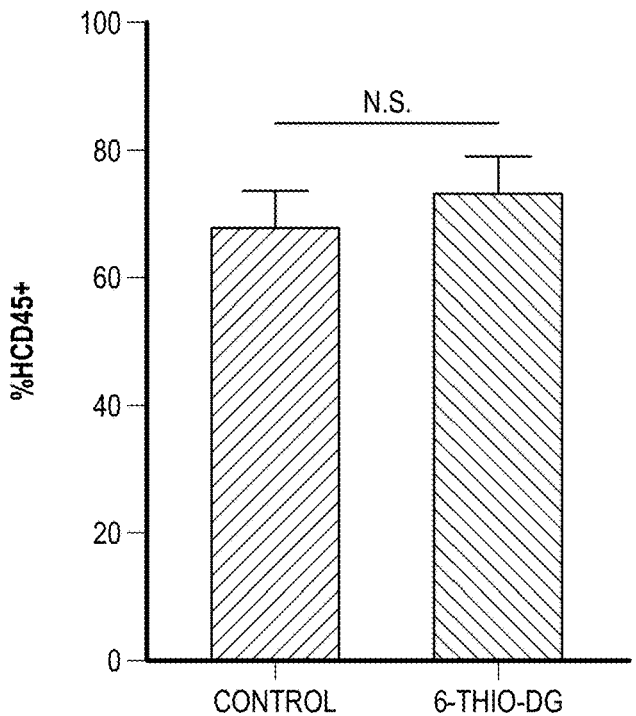
Figure 13C:
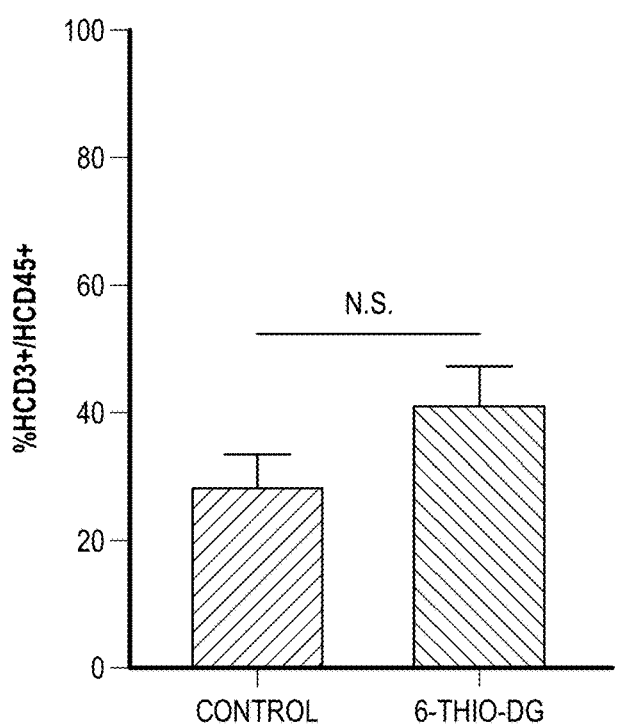
Figure 13D:
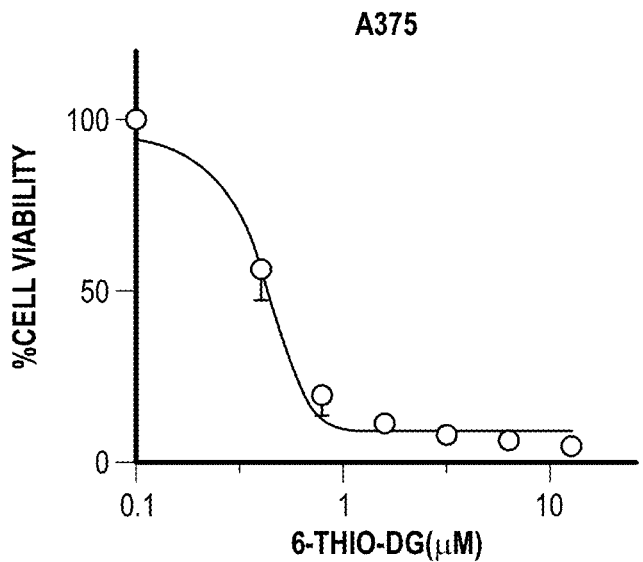
Figure 13E:
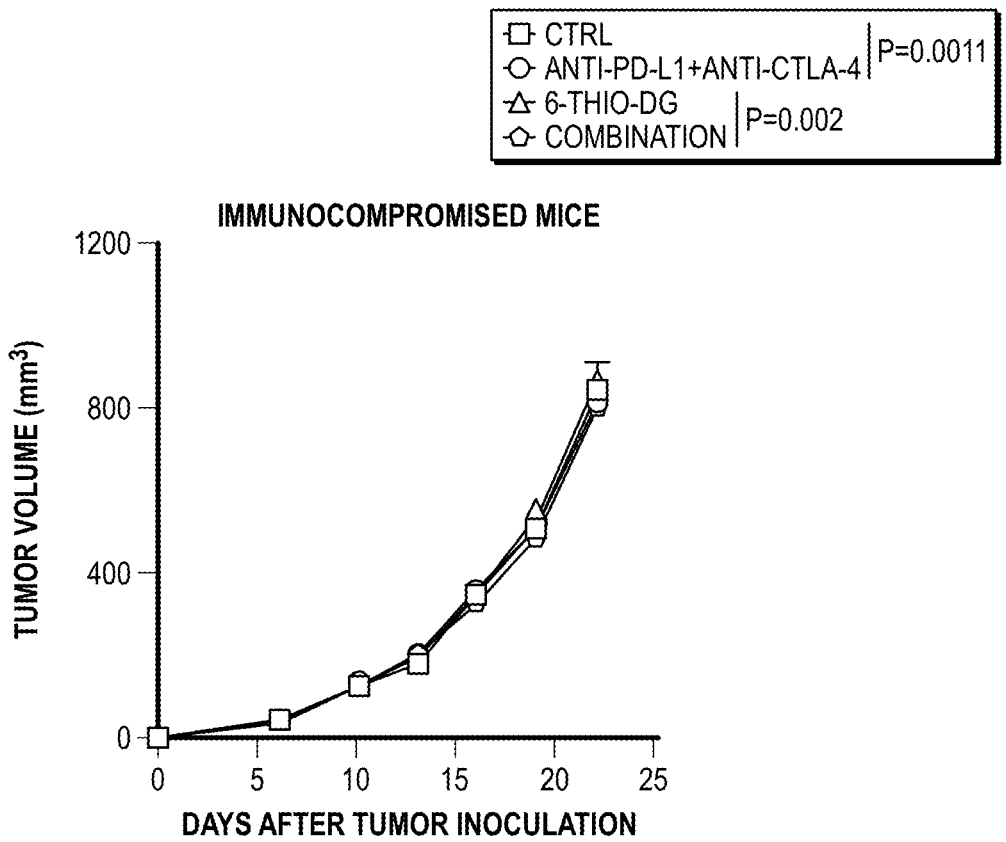
Figure 13F:
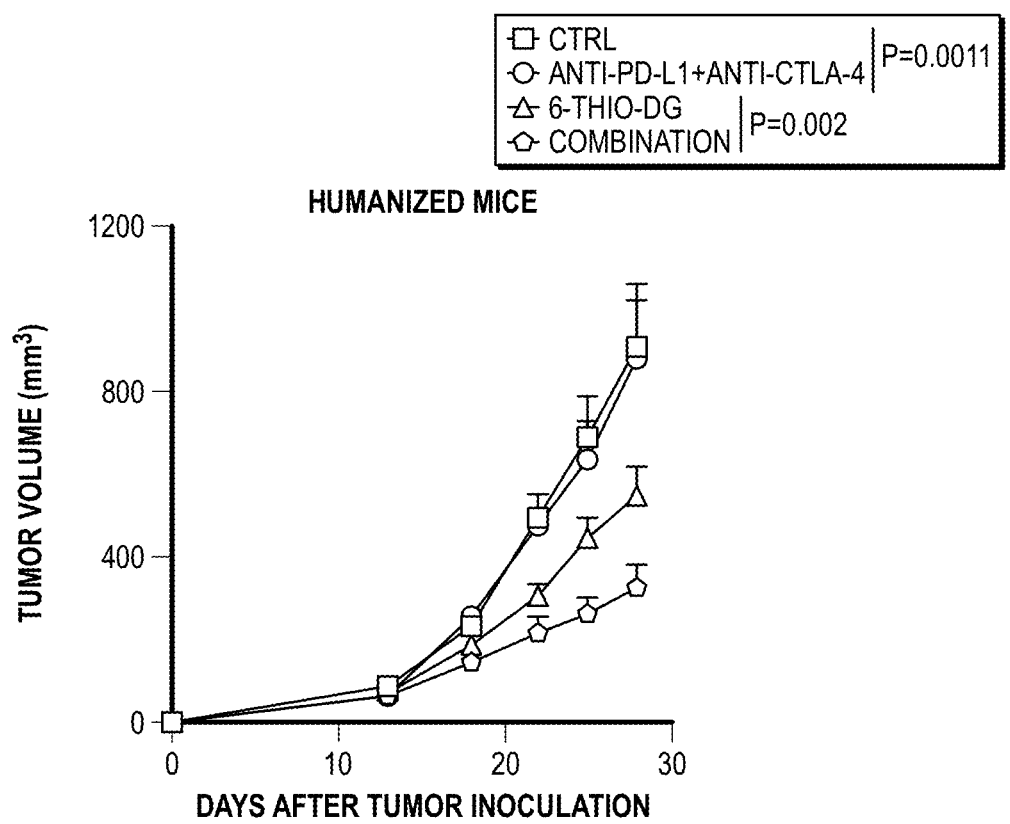
Figure 14:
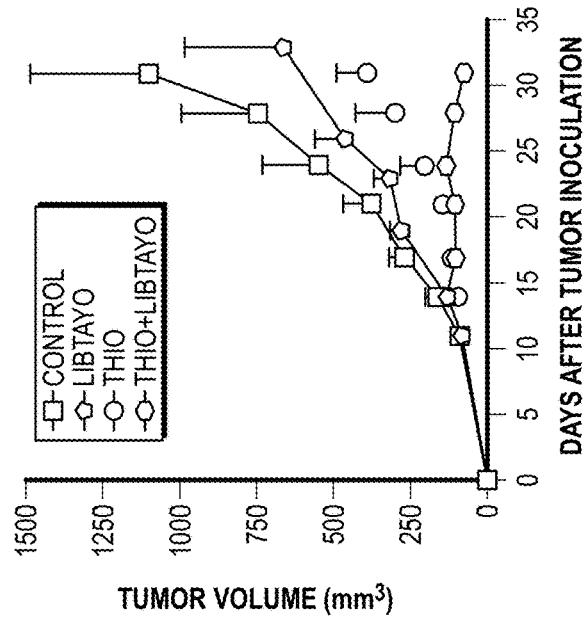
FIG. 14 shows the effects of 6-thio-dG with anti-PD-1 agent cemiplimab (Libtayo®) on tumor volume in mice carrying LLC cells-derived tumors (NSCLC). Dosing was 6-thio-dG 3 mg/kg (i.p) and cemiplimab-10 mg/kg (i.p). The different groups were dosed as shown in the table below. Day 1 (12/31/2020): 1000K LLC cells were inoculated to 35 B6 mice. Day 11-13: Experiment started. 3 mg/kg 6-thio-dG and 10 mg/kg Libtayo were used in this study.

6-thio-dG reduces human colon cancer burden in a humanized mouse model. Previous studies showed high TERT (the catalytic subunit of the telomerase) expression patients have poor clinical outcomes in various cancers such as non-small cell lung cancer and B cell chronic lymphocytic leukemia (Terrin et al., 2007; Wang et al., 2002). The inventors thus analyzed colorectal adenocarcinoma patients from the TCGA database and found patients with abnormal high expression of TERT had significantly worse overall survival rates compared to the colon cancer patients with low TERT expression (FIG. 6A). To directly demonstrate whether 6-thio-dG induced telomere stress can benefit cancer patients in a more clinically relevant model, the inventors developed a humanized mouse model with NSG-SGM3 mouse which has human SCF-1, GM-CSF and IL-3 transgenic expression that support the better development of human myeloid cells. They reconstituted the human immune system in NSG-SGM3 mice with human CD34+ hematopoietic stem cells (HSCs). 12 weeks after HSCs transfer, the humanized mice had an average of over 60% human CD45+ cells and over 20% human T cells among human CD45+ cells in circulation (FIGS. 13A-13C). Then the inventors inoculated HCT116, a human colon cancer cell line that is sensitive to 6-thio-dG treatment with an IC$_{50}$ of 0.73 μM (FIG. 6B), into NSG-SGM3 control mice and humanized NSG-SGM3 mice. The control group of humanized mice had similar constitution of human immune cells with 6-thio-dG treated group before treatment started (FIGS. 13B and 13C). After three doses of 6-thio-dG treatment, immunocompromised mice did not have significant difference compared to control group (FIG. 6D). Remarkably, the humanized mice significantly delayed tumor growth with 6-thio-dG treatment (FIGS. 6C and 6E). The inventors then tested a human melanoma cell line A375 that is sensitive to 6-thio-dG in vitro (FIG. 13D). They did not observe any effect in immunocompromised NSG-SGM3 mice since they provided a relatively short-time 6-thio-dG treatment (FIG. 13E). Notably, they found a treatment with two doses of 6-thio-dG partially delayed tumor growth in humanized mice. In addition, combination with checkpoint blockades further reduced tumor burden, suggesting pretreatment with 6-thio-dG sensitizes human tumors to checkpoint blockades (FIG. 13F). Given that humanized mice only partially restore human immunity due to missing some immune cells and limited number of human T cells, it is not surprising that the inventors did not observe complete tumor regression.

Figure 8A:
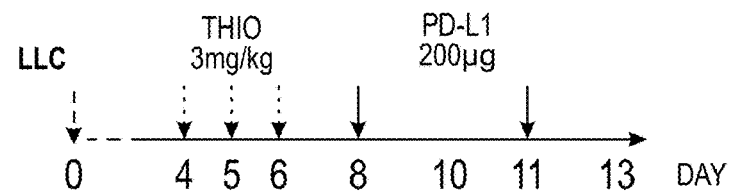
FIGS. 8A-B. Evidence for 6-thio-dG followed by PD-L1 results in complete tumor remission and immunogenic memory.
Figure 8A:
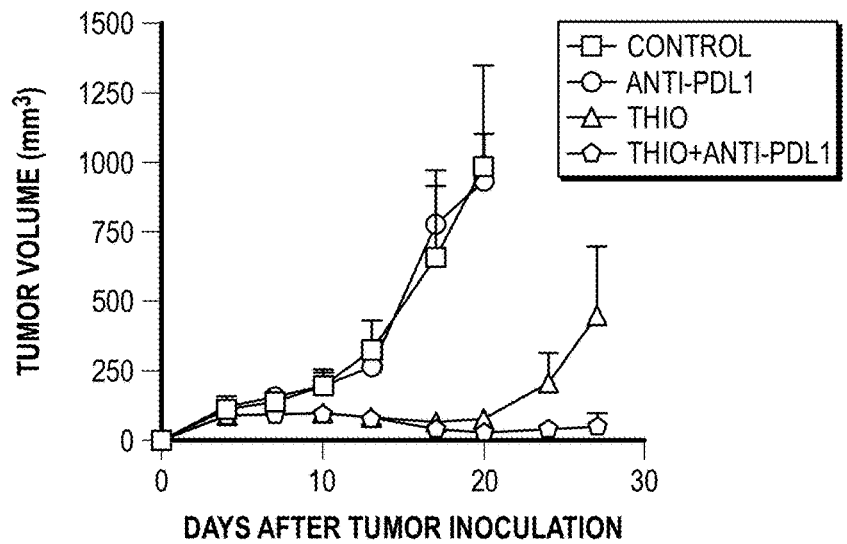
Figure 8B:
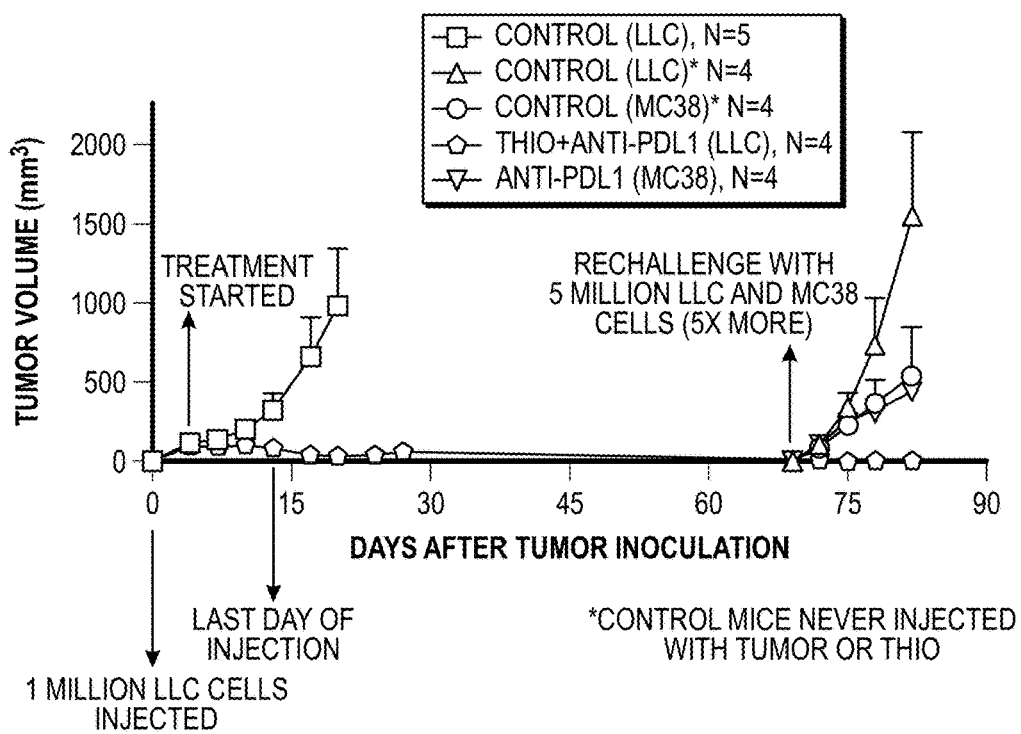
Figure 9A:
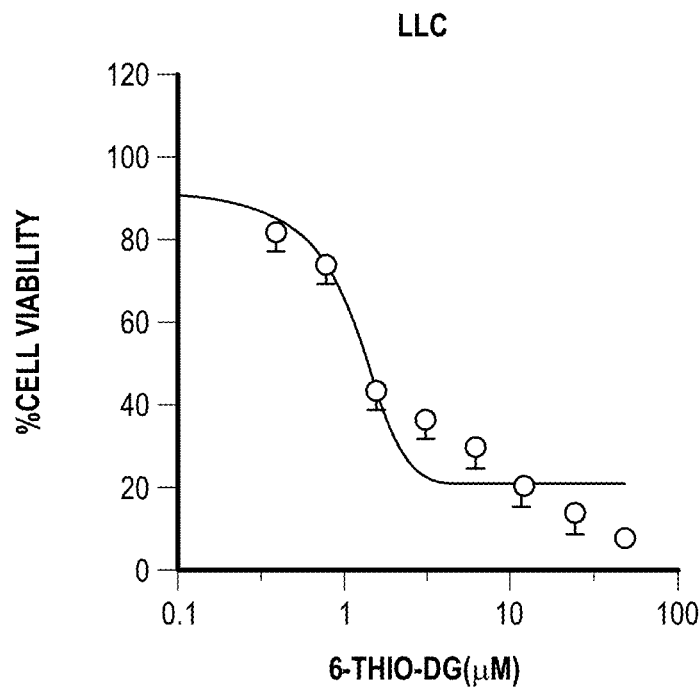
FIGS. 9A-D (related to FIGS. 1A-G).
Figure 9B:
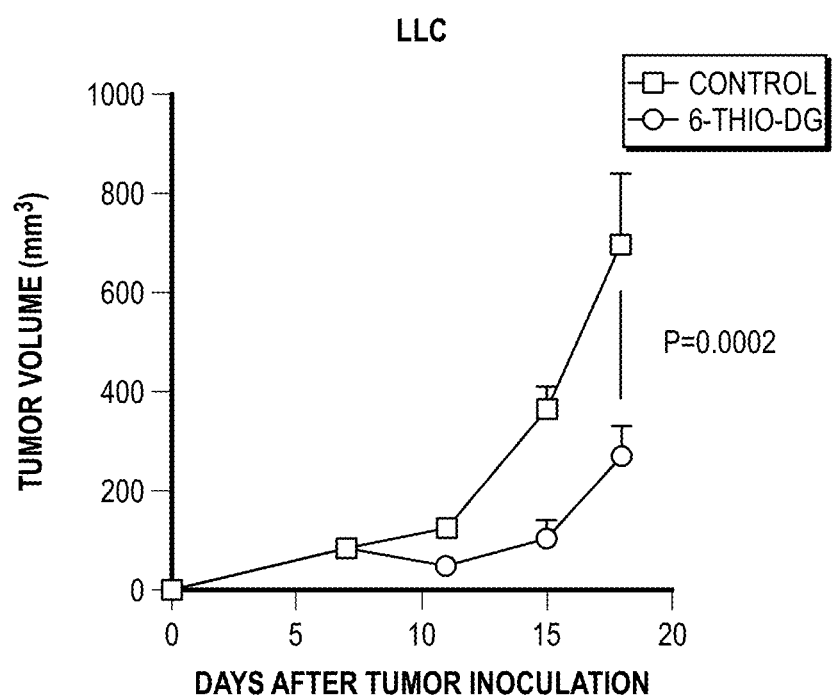
Figure 9C:
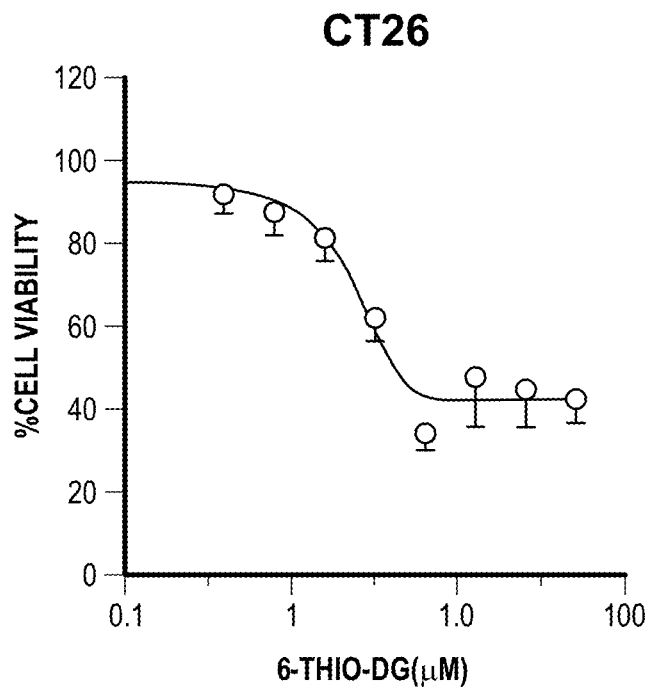
Figure 9D:
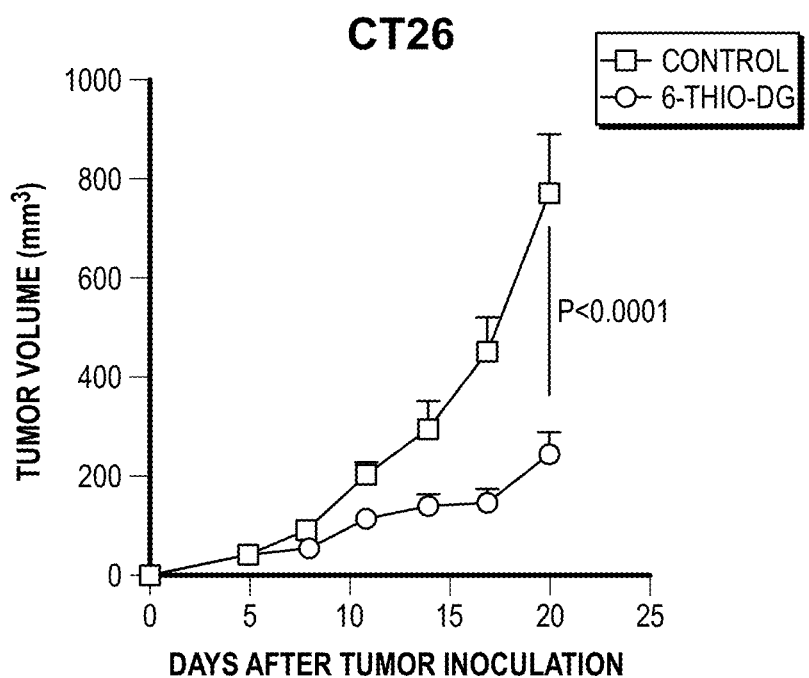

The inventors have demonstrated (FIGS. 8A-B) that three days treatment with 6-thio-dG followed two days later with anti-PD-L1 results in complete tumor remissions in the lewis lung carcinoma. This is a very aggressive tumor type as is illustrated in FIG. 8A. Within 20 day the tumor injected subcutaneously reached to over 1000 m$^3$. They observed the same rapid tumor growth with just treating with anti-PD-L1. However, just three treatments with 6-thio-dG (THIO) results in significant tumor control for 20 days. Surprisingly, treatment with THIO followed by anti-PDL-L1 (Atezolizumab) resulted in complete tumor regression. The inventors maintained the cured mice for 5 additional weeks and rechallenged the same mice with five time more LLC tumor and no tumor growth was observed. However, if they injected the LLC cured mice with MC38 the tumors grew and anti-PD-L1 had no affect (FIG. 8B). In control mice that were never treated with THIO, control LLC tumors grew similarly to MC38. This suggests tumor specific immune memory.

Overall, these data can be interpreted to support that 6-thio-dG induces telomerase-dependent DNA damage and increases tumor DNAs taken up by DCs. The increased cytosolic DNAs trigger the DC-intrinsic STING/IFN-I pathway, resulting in enhanced cross-priming capacity of DCs and subsequent tumor-specific T cell activation. Moreover, 6-thio-dG overcomes PD-L1 blockade resistance in advanced tumors. This study identifies 6-thio-dG as a novel immune stimulatory drug that will potentially benefit a wide population of cancer patients in the clinic.

Example 3—Discussion

High telomerase expression in tumor cells is recognized as a poor prognostic factor for cancer development (Zhang et al., 2018). Here, the inventors report a previously undefined role of a telomerase dependent telomere targeting therapy (6-thio-dG) in inducing anti-tumor immune responses in syngeneic colon and lung mouse models and humanized mouse cancer models. This effect is mediated through triggering the cytosolic DNA sensing STING/IFN-I pathway in DCs, which ultimately enhances the cross-priming capacity of DCs and subsequent tumor specific T cell activation. This is a remarkable finding since telomerase is a universal tumor marker and it can potentially be applied to many other telomerase positive cancers. Moreover, sequential administration of 6-thio-dG and anti-PD-L1 overcomes PD-L1 resistance in PD-L1 blockade resistant tumors, suggesting the combination therapy can benefit PD-L1 resistant patients in the clinic.

Current dogma is that 6-thio-dG treatment kill tumor cells mainly by impairing telomeres and inducing DNA damage. This study demonstrates that this drug also controls tumors largely depending on DNA sensing and T cell responses. Most previous studies use xenograft models without an intact immune system. In these models, they can only study tumor intrinsic effects or part of the innate immune responses. Even though these might be important factors, T cells are essential for long-term tumor control. In addition, most previous studies tend to use high dose or intensive dosing strategies that directly kill tumor cells more efficiently but actually dampen immune responses, either due to the toxicity to immune cells or the non-immunogenic death of tumor cells (Galluzzi et al., 2017; Kroemer et al., 2013). Also, these intensive dosing strategies often lead to the emergence of tumor resistance mechanisms. In the present study, the inventors took advantage of syngeneic mouse models with intact immune systems and humanized mouse model with more clinical relevance to fully evaluate the impact of lower doses and shorter treatment regimens with 6-thio-dG on host immune responses in tumor bearing mice. This discovery that 6-thio-dG is an immune stimulatory drug might allow the design of better combinational treatments including immunotherapy to amplify initial immunity.

Accumulating studies show that tumor DNA mediated innate sensing is critical for the induction of anti-tumor immune responses and the STING/IFN I pathway is primarily involved in initiation of anti-tumor immune response, but whether host or tumor autonomous STING is more essential depends on different treatment regimens (Deng et al., 2014; Li et al., 2019; Qiao et al., 2017; Sen et al., 2019; Vanpouille-Box et al., 2017; Woo et al., 2014). This discrepancy is likely to be explained by the relative STING activation strength of hosts versus tumor cells, for example, tumor cells might have STING pathway suppression or low activity (Xia et al., 2016). The inventors demonstrated that the 6-thio-dG treatment triggered innate sensing is host STING signaling dependent as 6-thio-dG completely lost its efficacy in Tmem173 deficient mice but not in Tmem173 deficient tumors. Since STING signaling in MC38 tumors is active, one explanation is after 6-thio-dG treatment, tumor intrinsic STING was activated but most tumor cells died, so little type I IFN can be produced. Another possibility is that there might be an intrinsic mechanism that limits STING activation in tumor cells, which still remains poorly defined. Recent reports showed STING signaling can also be involved in autophagy activation, which is less likely to contribute to the therapeutic effect of 6-thio-dG (Gui et al., 2019; Nassour et al., 2019) since the inventors did not see activation of autophagy in tumor cells after 6-thio-dG treatment (data not shown). Also, 6-thio-dG lost efficacy in Ifnar1 deficient mice, suggesting the involvement of IFN I signaling. However, STING activation of autophagy is IFN I signaling independent.

Compared to the general DNA damage induction approaches, for example, radiation therapy or chemotherapy that non-selectively induce DNA damage in all proliferating cells, one unique feature of 6-thio-dG is the specific induction of telomere-associated DNA damage in telomerase expressing cells, primarily tumor cells, but not affecting immune cells and other telomerase-silent somatic cells. Importantly, 6-thio-dG can be preferentially incorporated into de novo-synthesized telomeres and causes rapid tumor shrinkage. However, direct telomerase inhibitors function through the inhibition of telomerase activity and rely on the progressive shortening of telomeres. In contrast, 6-thio-dG takes effect rapidly regardless of the initial telomere length. This is critical in reducing toxicity compared with a direct telomerase inhibitor (Gryaznov et al., 2007; Mender et al., 2015b). The inventors show that 6-thio-dG induced DNA damage is significantly co-localized with telomeres, indicating the formation of telomere dysfunction induced foci (TIF). Telomeres are only ~1/6000th of genomic DNA so any TIF is highly significant. Moreover, some TIFs are taken up by DCs and further trigger STING-dependent IFN I signaling.

Despite the overwhelming success of checkpoint blockade, especially PD-1/PD-L1 blockade, in the clinic, only a minority of patients respond well. Both primary and adaptive resistances limit clinical benefit of PD-1/PD-L1 therapy (Chen and Han, 2015; Gide et al., 2018; Zaretsky et al., 2016; Zou et al., 2016). The inventors believe that lack of proper innate sensing might limit T cell activation inside the tumor microenvironment, therefore combination therapy of targeting both innate and adaptive immune cells is urgently needed. PD-L1 blockade reinvigorates adaptive immune responses by "releasing the brake", while 6-thio-dG induced innate sensing by "adding fuel". The inventors hypothesized combination of 6-thio-dG with PD-L1 blockade should augment overall anti-tumor immunity responses. Indeed, this study showed sequential administration of 6-thio-dG and anti-PD-L1 have synergistic effect in advanced tumors and in PD-L1 blockade resistant tumors. Further studies should be carried out regarding optimal combination regimens.

Overall, these results reveal a previously undefined role of 6-thio-dG, a telomerase-dependent telomere targeting small molecule drug, in potentiating anti-tumor immune responses. Mechanistically, 6-thio-dG induces telomere dysfunction and increases cytosolic DNA release. Importantly, these telomeric DNA fragments are taken up by DCs and activate the DC intrinsic STING/IFN pathway, resulting in enhanced cross-priming capacity of DCs and subsequent tumor specific T cell activation. Moreover, this study showing the remarkable efficacy of sequential administration of 6-thio-dG and anti-PD-L1 in advanced tumors and PD-L1 blockade resistant tumors provides a strong scientific rationale for propelling combination therapy into clinical trials. The inventors expect that these findings will be translated in the near future and benefit more patients in the clinic.

All of the methods disclosed and claimed herein can be made and executed without undue experimentation in light of the present disclosure. While the compositions and methods of this disclosure have been described in terms of particular embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims

VI. REFERENCES

The following references, to the extent that they provide exemplary procedural or other details supplementary to those set forth herein, are specifically incorporated herein by reference.

Ablasser, A., Goldeck, M., Cavlar, T., Deimling, T., Witte, G., Rohl, I., Hopfner, K. P., Ludwig, J., and Hornung, V. (2013). cGAS produces a 2'-5'-linked cyclic dinucleotide second messenger that activates STING. Nature 498, 380-384.

Blackburn, E. H. (1991). Structure and function of telomeres. Nature 350, 569-573.

Brahmer, J. R., Tykodi, S. S., Chow, L. Q., Hwu, W. J., Topalian, S. L., Hwu, P., Drake, C. G., Camacho, L. H., Kauh, J., Odunsi, K., et al. (2012). Safety and activity of anti-PD-L1 antibody in patients with advanced cancer. N Engl J Med 366, 2455-2465.

Broz, M. L., Binnewies, M., Boldajipour, B., Nelson, A. E., Pollack, J. L., Erle, D. J., Barczak, A., Rosenblum, M. D., Daud, A., Barber, D. L., et al. (2014). Dissecting the Tumor Myeloid Compartment Reveals Rare Activating Antigen-Presenting Cells Critical for T Cell Immunity. Cancer Cell 26, 938.

Bullock, B. L., Kimball, A. K., Poczobutt, J. M., Neuwelt, A. J., Li, H. Y., Johnson, A. M., Kwak, J. W., Kleczko, E. K., Kaspar, R. E., Wagner, E. K., et al. (2019). Tumor-intrinsic response to IFNgamma shapes the tumor microenvironment and anti-PD-1 response in NSCLC. Life Sci Alliance 2.

Chen, L., and Han, X. (2015). Anti-PD-1/PD-L1 therapy of human cancer: past, present, and future. J Clin Invest 125, 3384-3391.

Deng, L., Liang, H., Xu, M., Yang, X., Burnette, B., Arina, A., Li, X. D., Mauceri, H., Beckett, M., Darga, T., et al. (2014). STING-Dependent Cytosolic DNA Sensing Promotes Radiation-Induced Type I Interferon-Dependent Antitumor Immunity in Immunogenic Tumors. Immunity 41, 843-852.

Diamond, M. S., Kinder, M., Matsushita, H., Mashayekhi, M., Dunn, G. P., Archambault, J. M., Lee, H., Arthur, C. D., White, J. M., Kalinke, U., et al. (2011). Type I interferon is selectively required by dendritic cells for immune rejection of tumors. J Exp Med 208, 1989-2003.

Diner, E. J., Burdette, D. L., Wilson, S. C., Monroe, K. M., Kellenberger, C. A., Hyodo, M., Hayakawa, Y., Hammond, M. C., and Vance, R. E. (2013). The innate immune DNA sensor cGAS produces a noncanonical cyclic dinucleotide that activates human STING. Cell reports 3, 1355-1361.

Edelson, B. T., Kc, W., Juang, R., Kohyama, M., Benoit, L. A., Klekotka, P. A., Moon, C., Albring, J. C., Ise, W., Michael, D. G., et al. (2010). Peripheral CD103+ dendritic cells form a unified subset developmentally related to CD8alpha+ conventional dendritic cells. J Exp Med 207, 823-836.

Fenech, M., Kirsch-Volders, M., Natarajan, A. T., Surralles, J., Crott, J. W., Parry, J., Norppa, H., Eastmond, D. A., Tucker, J. D., and Thomas, P. (2011). Molecular mechanisms of micronucleus, nucleoplasmic bridge and nuclear bud formation in mammalian and human cells. Mutagenesis 26, 125-132.

Galluzzi, L., Buque, A., Kepp, O., Zitvogel, L., and Kroemer, G. (2017). Immunogenic cell death in cancer and infectious disease. Nat Rev Immunol 17, 97-111.

Gao, P., Ascano, M., Wu, Y., Barchet, W., Gaffney, B. L., Zillinger, T., Serganov, A. A., Liu, Y., Jones, R. A., Hartmann, G., et al. (2013). Cyclic [G (2',5')pA(3',5')p] is the metazoan second messenger produced by DNA-activated cyclic GMP-AMP synthase. Cell 153, 1094-1107.

Garon, E. B., Rizvi, N. A., Hui, R., Leighl, N., Balmanoukian, A. S., Eder, J. P., Patnaik, A., Aggarwal, C., Gubens, M., Horn, L., et al. (2015). Pembrolizumab for the treatment of non-small-cell lung cancer. N Engl J Med 372, 2018-2028.

Gide, T. N., Wilmott, J. S., Scolyer, R. A., and Long, G. V. (2018). Primary and Acquired Resistance to Immune Checkpoint Inhibitors in Metastatic Melanoma. Clin Cancer Res 24, 1260-1270.

Greider, C. W. (1996). Telomere length regulation. Annual review of biochemistry 65, 337-365.

Greider, C. W., and Blackburn, E. H. (1985). Identification of a specific telomere terminal transferase activity in Tetrahymena extracts. Cell 43, 405-413.

Gryaznov, S. M., Jackson, S., Dikmen, G., Harley, C., Herbert, B. S., Wright, W. E., and Shay, J. W. (2007). Oligonucleotide conjugate GRN163L targeting human telomerase as potential anticancer and antimetastatic agent. Nucleosides Nucleotides Nucleic Acids 26, 1577-1579.

Gui, X., Yang, H., Li, T., Tan, X., Shi, P., Li, M., Du, F., and Chen, Z. J. (2019). Autophagy induction via STING trafficking is a primordial function of the cGAS pathway. Nature 567, 262-266.

Hodi, F. S., O'Day, S. J., McDermott, D. F., Weber, R. W., Sosman, J. A., Haanen, J. B., Gonzalez, R., Robert, C., Schadendorf, D., Hassel, J. C., et al. (2010). Improved survival with ipilimumab in patients with metastatic melanoma. N Engl J Med 363, 711-723.

Kroemer, G., Galluzzi, L., Kepp, O., and Zitvogel, L. (2013). Immunogenic Cell Death in Cancer Therapy. Annual Review of Immunology 31, 51-72.

Lansdorp, P. M., Verwoerd, N. P., van de Rijke, F. M., Dragowska, V., Little, M. T., Dirks, R. W., Raap, A. K., and Tanke, H. J. (1996). Heterogeneity in telomere length of human chromosomes. Human molecular genetics 5, 685-691.

Le Bon, A., Etchart, N., Rossmann, C., Ashton, M., Hou, S., Gewert, D., Borrow, P., and Tough, D. F. (2003). Cross-priming of CD8+ T cells stimulated by virus-induced type I interferon. Nat Immunol 4, 1009-1015.

Le, D. T., Durham, J. N., Smith, K. N., Wang, H., Bartlett, B. R., Aulakh, L. K., Lu, S., Kemberling, H., Wilt, C., Luber, B. S., et al. (2017). Mismatch repair deficiency predicts response of solid tumors to PD-1 blockade. Science 357, 409-413.

Li, H. Y., McSharry, M., Bullock, B., Nguyen, T. T., Kwak, J., Poczobutt, J. M., Sippel, T. R., Heasley, L. E., Weiser-Evans, M. C., Clambey, E. T., and Nemenoff, R. A. (2017). The Tumor Microenvironment Regulates Sensitivity of Murine Lung Tumors to PD-1/PD-L1 Antibody Blockade. Cancer Immunol Res 5, 767-777.

Li, T., and Chen, Z. J. (2018). The cGAS-cGAMP-STING pathway connects DNA damage to inflammation, senescence, and cancer. The Journal of experimental medicine 215, 1287-1299.

Li, X., Liu, Z., Zhang, A., Han, C., Shen, A., Jiang, L., Boothman, D. A., Qiao, J., Wang, Y., Huang, X., and Fu, Y. X. (2019). NQO1 targeting prodrug triggers innate sensing to overcome checkpoint blockade resistance. Nat Commun 10, 3251.

Liu, S., Cai, X., Wu, J., Cong, Q., Chen, X., Li, T., Du, F., Ren, J., Wu, Y. T., Grishin, N. V., and Chen, Z. J. (2015). Phosphorylation of innate immune adaptor proteins MAVS, STING, and TRIF induces IRF3 activation. Science 347, aaa2630.

Liu, Z., Han, C., Dong, C., Shen, A., Hsu, E., Ren, Z., Lu, C., Liu, L., Zhang, A., Timmerman, C., et al. (2019). Hypofractionated EGFR tyrosine kinase inhibitor limits tumor relapse through triggering innate and adaptive immunity. Sci Immunol 4.

Mandal, R., Samstein, R. M., Lee, K. W., Havel, J. J., Wang, H., Krishna, C., Sabio, E. Y., Makarov, V., Kuo, F., Blecua, P., et al. (2019). Genetic diversity of tumors with mismatch repair deficiency influences anti-PD-1 immunotherapy response. Science 364, 485-491.

McEachern, M. J., and Blackburn, E. H. (1996). Cap-prevented recombination between terminal telomeric repeat arrays (telomere CPR) maintains telomeres in *Kluyveromyces lactis* lacking telomerase. Genes & development 10, 1822-1834.

Mender, I., Gryaznov, S., Dikmen, Z. G., Wright, W. E., and Shay, J. W. (2015a). Induction of telomere dysfunction mediated by the telomerase substrate precursor 6-thio-2'-deoxyguanosine. Cancer Discov 5, 82-95.

Mender, I., Gryaznov, S., and Shay, J. W. (2015b). A novel telomerase substrate precursor rapidly induces telomere dysfunction in telomerase positive cancer cells but not telomerase silent normal cells. Oncoscience 2, 693-695.

Mender, I., LaRanger, R., Luitel, K., Peyton, M., Girard, L., Lai, T. P., Batten, K., Cornelius, C., Dalvi, M. P., Ramirez, M., et al. (2018). Telomerase-Mediated Strategy for Overcoming Non-Small Cell Lung Cancer Targeted Therapy and Chemotherapy Resistance. Neoplasia 20, 826-837.

Mender, I., and Shay, J. W. (2015). Telomere Dysfunction Induced Foci (TIF) Analysis. Bio-protocol 5.

Min, J., Wright, W. E., and Shay, J. W. (2019). Clustered telomeres in phase-separated nuclear condensates engage mitotic DNA synthesis through BLM and RAD52. Genes Dev 33, 814-827.

Morin, G. B. (1989). The human telomere terminal transferase enzyme is a ribonucleoprotein that synthesizes TTAGGG repeats. Cell 59, 521-529.

Nakamura, T. M., Morin, G. B., Chapman, K. B., Weinrich, S. L., Andrews, W. H., Lingner, J., Harley, C. B., and Cech, T. R. (1997). Telomerase catalytic subunit homologs from fission yeast and human. Science 277, 955-959.

Nassour, J., Radford, R., Correia, A., Fuste, J. M., Schoell, B., Jauch, A., Shaw, R. J., and Karlseder, J. (2019). Autophagic cell death restricts chromosomal instability during replicative crisis. Nature 565, 659-663.

Pitt, J. M., Kroemer, G., and Zitvogel, L. (2017). Immunogenic and Non-immunogenic Cell Death in the Tumor Microenvironment. Adv Exp Med Biol 1036, 65-79.

Qiao, J., Liu, Z., Dong, C., Luan, Y., Zhang, A., Moore, C., Fu, K., Peng, J., Wang, Y., Ren, Z., et al. (2019). Targeting Tumors with IL-10 Prevents Dendritic Cell-Mediated CD8(+) T Cell Apoptosis. Cancer Cell 35, 901-915 e904.

Qiao, J., Tang, H., and Fu, Y. X. (2017). DNA sensing and immune responses in cancer therapy. Curr Opin Immunol 45, 16-20.

Reinhardt, R. L., Liang, H. E., and Locksley, R. M. (2009). Cytokine-secreting follicular T cells shape the antibody repertoire. Nat Immunol 10, 385-393.

Ribas, A., Hamid, O., Daud, A., Hodi, F. S., Wolchok, J. D., Kefford, R., Joshua, A. M., Patnaik, A., Hwu, W. J., Weber, J. S., et al. (2016). Association of Pembrolizumab With Tumor Response and Survival Among Patients With Advanced Melanoma. JAMA 315, 1600-1609.

Ribas, A., and Wolchok, J. D. (2018). Cancer immunotherapy using checkpoint blockade. Science 359, 1350-1355.

Rizvi, N. A., Hellmann, M. D., Snyder, A., Kvistborg, P., Makarov, V., Havel, J. J., Lee, W., Yuan, J., Wong, P., Ho, T. S., et al. (2015a). Cancer immunology. Mutational landscape determines sensitivity to PD-1 blockade in non-small cell lung cancer. Science 348, 124-128.

Rizvi, N. A., Mazieres, J., Planchard, D., Stinchcombe, T. E., Dy, G. K., Antonia, S. J., Horn, L., Lena, H., Minenza, E., Mennecier, B., et al. (2015b). Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol 16, 257-265.

Sanchez-Paulete, A. R., Teijeira, A., Cueto, F. J., Garasa, S., Perez-Gracia, J. L., Sanchez-Arraez, A., Sancho, D., and Melero, I. (2017). Antigen cross-presentation and T-cell cross-priming in cancer immunology and immunotherapy. Ann Oncol 28, xii44-xii55.

Sen, T., Rodriguez, B. L., Chen, L., Corte, C. M. D., Morikawa, N., Fujimoto, J., Cristea, S., Nguyen, T., Diao, L., Li, L., et al. (2019). Targeting DNA Damage Response Promotes Antitumor Immunity through STING-Mediated T-cell Activation in Small Cell Lung Cancer. Cancer Discov 9, 646-661.

Sengupta, S., Sobo, M., Lee, K., Senthil Kumar, S., White, A. R., Mender, I., Fuller, C., Chow, L. M. L., Fouladi, M., Shay, J. W., and Drissi, R. (2018). Induced Telomere Damage to Treat Telomerase Expressing Therapy-Resistant Pediatric Brain Tumors. Molecular cancer therapeutics 17, 1504-1514.

Shay, J. W., and Bacchetti, S. (1997). A survey of telomerase activity in human cancer. European journal of cancer 33, 787-791.

Singer, M. S., and Gottschling, D. E. (1994). TLC1: template RNA component of Saccharomyces cerevisiae telomerase. Science 266, 404-409.

Socinski, M. A., Jotte, R. M., Cappuzzo, F., Orlandi, F., Stroyakovskiy, D., Nogami, N., Rodriguez-Abreu, D., Moro-Sibilot, D., Thomas, C. A., Barlesi, F., et al. (2018). Atezolizumab for First-Line Treatment of Metastatic Nonsquamous NSCLC. N Engl J Med 378, 2288-2301.

Tanaka, Y., and Chen, Z. J. (2012). STING specifies IRF3 phosphorylation by TBK1 in the cytosolic DNA signaling pathway. Science signaling 5, ra20.

Terrin, L., Trentin, L., Degan, M., Corradini, I., Bertorelle, R., Carli, P., Maschio, N., Bo, M. D., Noventa, F., Gattei, V., et al. (2007). Telomerase expression in B-cell chronic lymphocytic leukemia predicts survival and delineates subgroups of patients with the same igVH mutation status and different outcome. Leukemia 21, 965-972.

Topalian, S. L., Hodi, F. S., Brahmer, J. R., Gettinger, S. N., Smith, D. C., McDermott, D. F., Powderly, J. D., Carvajal, R. D., Sosman, J. A., Atkins, M. B., et al. (2012). Safety, activity, and immune correlates of anti-PD-1 antibody in cancer. N Engl J Med 366, 2443-2454.

Vanpouille-Box, C., Alard, A., Aryankalayil, M. J., Sarfraz, Y., Diamond, J. M., Schneider, R. J., Inghirami, G., Coleman, C. N., Formenti, S. C., and Demaria, S. (2017). DNA exonuclease Trexi regulates radiotherapy-induced tumour immunogenicity. Nat Commun 8, 15618.

Wang, L., Soria, J. C., Kemp, B. L., Liu, D. D., Mao, L., and Khuri, F. R. (2002). hTERT expression is a prognostic factor of survival in patients with stage I non-small cell lung cancer. Clin Cancer Res 8, 2883-2889.

West, A. P., Khoury-Hanold, W., Staron, M., Tal, M. C., Pineda, C. M., Lang, S. M., Bestwick, M., Duguay, B. A., Raimundo, N., MacDuff, D. A., et al. (2015). Mitochondrial DNA stress primes the antiviral innate immune response. Nature 520, 553-557.

Woo, S. R., Fuertes, M. B., Corrales, L., Spranger, S., Furdyna, M. J., Leung, M. Y., Duggan, R., Wang, Y., Barber, G. N., Fitzgerald, K. A., et al. (2014). STING-dependent cytosolic DNA sensing mediates innate immune recognition of immunogenic tumors. Immunity 41, 830-842.

Wu, J., Sun, L., Chen, X., Du, F., Shi, H., Chen, C., and Chen, Z. J. (2013). Cyclic GMP-AMP is an endogenous second messenger in innate immune signaling by cytosolic DNA. Science 339, 826-830.

Xia, T., Konno, H., Ahn, J., and Barber, G. N. (2016). Deregulation of STING Signaling in Colorectal Carcinoma Constrains DNA Damage Responses and Correlates With Tumorigenesis. Cell Rep 14, 282-297.

Xu, M. M., Pu, Y., Han, D., Shi, Y., Cao, X., Liang, H., Chen, X., Li, X. D., Deng, L., Chen, Z. J., et al. (2017). Dendritic Cells but Not Macrophages Sense Tumor Mitochondrial DNA for Cross-priming through Signal Regulatory Protein alpha Signaling. Immunity 47, 363-373 e365.

Yu, G. L., Bradley, J. D., Attardi, L. D., and Blackburn, E. H. (1990). In vivo alteration of telomere sequences and senescence caused by mutated Tetrahymena telomerase RNAs. Nature 344, 126-132.

Zaretsky, J. M., Garcia-Diaz, A., Shin, D. S., Escuin-Ordinas, H., Hugo, W., Hu-Lieskovan, S., Torrejon, D. Y., Abril-Rodriguez, G., Sandoval, S., Barthly, L., et al. (2016). Mutations Associated with Acquired Resistance to PD-1 Blockade in Melanoma. N Engl J Med 375, 819-829.

Zhang, G., Wu, L. W., Mender, I., Barzily-Rokni, M., Hammond, M. R., Ope, O., Cheng, C., Vasilopoulos, T., Randell, S., Sadek, N., et al. (2018). Induction of Telomere Dysfunction Prolongs Disease Control of Therapy-Resistant Melanoma. Clin Cancer Res 24, 4771-4784.

Zhang, X., Shi, H., Wu, J., Zhang, X., Sun, L., Chen, C., and Chen, Z. J. (2013). Cyclic GMP-AMP containing mixed phosphodiester linkages is an endogenous high-affinity ligand for STING. Molecular cell 51, 226-235.

Zijlmans, J. M., Martens, U. M., Poon, S. S., Raap, A. K., Tanke, H. J., Ward, R. K., and Lansdorp, P. M. (1997). Telomeres in the mouse have large inter-chromosomal variations in the number of T2AG3 repeats. Proceedings of the National Academy of Sciences of the United States of America 94, 7423-7428.

Zou, W., Wolchok, J. D., and Chen, L. (2016). PD-L1 (B7-H1) and PD-1 pathway blockade for cancer therapy: Mechanisms, response biomarkers, and combinations. Sci Transl Med 8, 328rv324.

What is claimed is:

1. A method of treating a cancer, in a subject, wherein the cancer treated is resistant to checkpoint inhibitors alone or in combination with chemotherapy comprising administering to said subject 6-thio-2'-deoxyguanosine (6-thio-dG) followed by treatment with a checkpoint inhibitor, selected from atezolizumab (Tecentrig®) and cemiplimab (Libtavo®) wherein the cancer is selected from the group consisting of, lung, liver, and colorectal.

2. The method according to claim 1, wherein the 6-thio-dG administered is for about 1 to about 5 days per therapeutic cycle and/or the checkpoint inhibitor is administered for about 1 to about 3 days per therapeutic cycle.

3. The method according to claim 1, wherein the checkpoint inhibitor is atezolizumab.

4. The method of claim 1, wherein said checkpoint inhibitor is cemiplimab.

5. The method according to claim 1, wherein the total dosage of 6-thio-dG administered over about 1-5 days of therapy is about 20-2000 mg.

6. The method according to claim 1, wherein the cancer is chemotherapy resistant.

7. The method according to claim 1, wherein said subject was previously treated with a checkpoint inhibitor therapy.

8. The method according to claim 7, wherein the subject was previously treated with one or more of a PD-1, or PD-L1 checkpoint inhibitor therapy.

9. The method of claim 1, wherein said 6-thio-dG and the checkpoint inhibitor are administered systemically.

10. The method of claim 1, wherein said 6-thio-dG and the checkpoint inhibitor are administered locally or regionally to a tumor site.

11. The method of claim 1, wherein said 6-thio-dG is administered locally or regionally to a tumor site and the checkpoint inhibitor is administered systemically.

12. The method of claim 1, wherein administration of 6-thio-dG and the checkpoint inhibitor results in inhibition of tumor growth.

13. The method of claim 1, wherein administration of 6-thio-dG and the checkpoint inhibitor results in remission of said cancer.

14. The method of claim 1, wherein administration of 6-thio-dG and the checkpoint inhibitor results in reduction in tumor burden.

15. The method of claim 1, wherein administration of 6-thio-dG and the checkpoint inhibitor results in inhibition of cancer cell metastasis.

16. The method of claim 1, wherein administration of 6-thio-dG and the checkpoint inhibitor results in tumor eradication.

* * * * *

UNITED STATES PATENT AND TRADEMARK OFFICE
CERTIFICATE OF CORRECTION

| | | |
|---|---|---|
| PATENT NO. | : 12,097,213 B2 | Page 1 of 1 |
| APPLICATION NO. | : 17/200539 | |
| DATED | : September 24, 2024 | |
| INVENTOR(S) | : Shay et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 138 days.

Signed and Sealed this
Eighteenth Day of March, 2025

Coke Morgan Stewart
*Acting Director of the United States Patent and Trademark Office*